United States Patent [19]
Bannwarth et al.

[11] Patent Number: 5,811,548
[45] Date of Patent: Sep. 22, 1998

[54] TRI-AND TETRACYCLIC COMPOUNDS

[75] Inventors: Wilhelm Bannwarth, Upper Saddle River, N.J.; Fernand Gerber, Niffer, France; Alfred Grieder, Sissach, Switzerland; Andreas Knierzinger, Birsfelden, Switzerland; Klaus Müller, Münchenstein, Switzerland; Daniel Obrecht, Basel, Switzerland; Arnold Trzeciak, Schopfheim, Germany

[73] Assignee: Hoffmann-La Roche Inc., Nutley, N.J.

[21] Appl. No.: 669,683

[22] Filed: Jun. 24, 1996

Related U.S. Application Data

[62] Division of Ser. No. 475,473, Jun. 7, 1995, abandoned, which is a continuation of Ser. No. 106,508, Aug. 13, 1993, abandoned.

[30] Foreign Application Priority Data

Aug. 31, 1992 [CH] Switzerland ............... 2725/92

[51] Int. Cl.$^6$ ............ C07D 221/06; C07D 265/38; C07D 279/18
[52] U.S. Cl. ............ 544/32; 544/35; 544/101; 544/102; 549/79; 514/224.8; 514/226.2; 514/290
[58] Field of Search ............ 544/98, 102, 103, 544/104, 35, 32, 101; 546/79; 514/228.2, 232.8, 224.8, 226.2, 290

[56] References Cited

U.S. PATENT DOCUMENTS

| | | | |
|---|---|---|---|
| 3,294,790 | 12/1966 | Harfenist | 260/243 |
| 4,707,473 | 11/1987 | Muchowski et al. | 514/63 |
| 4,845,083 | 7/1989 | Fortin et al. | 514/80 |
| 4,931,429 | 6/1990 | Hanson et al. | 514/63 |
| 4,952,587 | 8/1990 | Baker et al. | 514/305 |

FOREIGN PATENT DOCUMENTS

| | | |
|---|---|---|
| 319 506 | 6/1989 | European Pat. Off. |
| 425 212 | 5/1991 | European Pat. Off. |
| 452 257 | 10/1991 | European Pat. Off. |
| 91/01331 | 2/1991 | WIPO |
| 91/07429 | 5/1991 | WIPO |
| 92/07870 | 5/1992 | WIPO |

OTHER PUBLICATIONS

Davies, et al., *Biochemical Society Transactions*, vol. 18, pp. 326–1328 (1990).
Diaz, H. and J. Kelly, *Tetrahedron Letters*, 32(41):5725–5728 (1991).
Ernest, I., et al., *Tetrahedron Letters*, 31(28):4011–4014 (1990).
Feigel, M., *J. Am. Chem. Soc.*, 108:181–182 (1986).
Feigel, M., *Liebigs Ann. Chem.*, pp. 459–468 (1989).
Rudinger, *Peptide Hormones*, pp. 1–7 (Jun. 1976).
The Merck Manual, 16th ed., Ch. 123, pp. 1451–1459. 1992.

*Primary Examiner*—Cecilia J. Tsang
*Assistant Examiner*—Anish Gupta
*Attorney, Agent, or Firm*—George W. Johnston; Dennis P. Tramaloni; Alan P. Kass

[57] ABSTRACT

There are described compounds of the formula

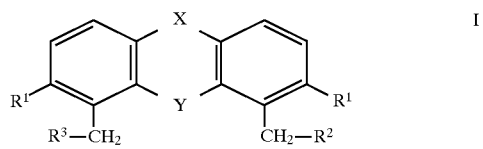

Wherein the variables have been defined herein. The compounds are useful as research tools in the determination of biologically active peptides sequences and also potentially suitable as medicaments, some of them being useful in the prevention or control of the formation of blood platelet thrombi, and some compounds are useful as intermediates.

2 Claims, No Drawings

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Ala   Thr   Val   Gly
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Arg   Gly   Asp   Val
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Gly   Asp   Gly   Gly
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gly   Gly   Ala   Gly
    1

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

```
Val  Arg  Lys  Lys
1
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ala  Arg  Gly  Asp  Phe  Pro
1                    5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Glu  Arg  Gly  Asp  Val  Tyr
1                    5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Ile  Ala  Arg  Gly  Asp  Phe  Pro  Asp
1                    5
```

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Val  Ala  Ala  Phe  Leu  Ala  Leu  Ala
1                    5
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Arg Ile Ala Arg Gly Asp Phe Pro Asp Asp
1               5                   10

( 2 ) INFORMATION FOR SEQ ID NO:11:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:11:

Ala Arg Ile Ala Arg Gly Asp Phe Pro Asp Asp Arg
1               5                   10

( 2 ) INFORMATION FOR SEQ ID NO:12:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:12:

Arg Gly Asp Phe
1

( 2 ) INFORMATION FOR SEQ ID NO:13:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:13:

Arg Gly Asp Ser
1

( 2 ) INFORMATION FOR SEQ ID NO:14:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:14:

Val Arg Lys Ile
1

( 2 ) INFORMATION FOR SEQ ID NO:15:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:15:

Ile Val Arg Lys Lys Pro

```
                 1                    5
```

(2) INFORMATION FOR SEQ ID NO:16:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa is d-arginine"

(ix) FEATURE:
        (A) NAME/KEY: Modified-site
        (B) LOCATION: 4
        (D) OTHER INFORMATION: /note= "Xaa is D-Isoleucine"

(xi) SEQUENCE DESCRIPTION: SEQ ID NO:16:

```
Gly  Xaa  Lys  Xaa
1
```

(2) INFORMATION FOR SEQ ID NO:17:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:17:

```
Arg  Lys  Ile  Gln  Ile  Val  Arg  Lys  Lys  Pro  Ile  Phe  Lys  Lys
1                    5                        10
```

TRI- AND TETRACYCLIC COMPOUNDS

This is a division of application Ser. No. 08/475,573, filed Jun. 7, 1995, now abandoned, which is a Continuation of application Ser. No. 08/106,508, filed Aug. 13, 1993, now abandoned.

BACKGROUND

FIELD OF THE INVENTION

This invention relates to tri- and tetracyclic compounds.

SUMMARY OF THE INVENTION

The present invention is concerned with tri- and tetracyclic compounds, primarily compounds of the general formula

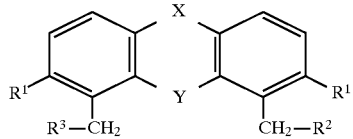

wherein X signifies a group of the formula

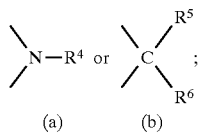

Y signifies oxygen or sulphur;

$R^1$ signifies hydrogen or lower alkoxy;

$R^2$ signifies protected amino, amino or a residue of the formula —NH—$R^7$ (c);

$R^3$ signifies carboxyl, functionally modified carboxyl or a residue of the formula —CO—$R^8$ (d);

$R^4$ signifies lower alkyl, aryl, aryl-lower alkyl, hydrogen or acyl;

$R^5$ and $R^6$ each signify lower alkyl, aryl or aryl-lower alkyl; and $R^7$ and $R^8$ are each individually a residue of an amino acid or a chain of up to 20 amino acid residues, whereby the amino acid residue or the amino acid residues can be protected or $R^7$ and $R^8$ together signify a residue of an amino acid or a chain of up to 20 amino acid residues whereby the amino acid residue or the amino acid residues can be protected, and whereby the molecule contains in total a maximum of 20 amino acid residues, and salts thereof.

The compounds of general formula I and their salts are novel. Those in which $R^2$ signifies a residue of formula (c), $R^3$ signifies a residue of formula (d) and $R^7$ and $R^8$ together signify a residue of an amino acid or a chain of up to 20 amino acid residues, i.e. compounds of the general formula

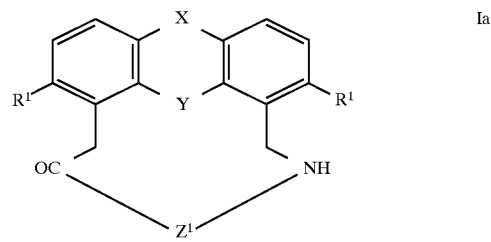

wherein X, Y and $R^1$ have the above significance and $Z^1$ signifies a residue of an amino acid or a chain of up to 20 amino acid residues, and salts thereof, especially those in which the amino acid residue or the chain of amino acid residues does not contain protecting group(s), are valuable aids in the determination of biologically active peptide sequences and are therefore so-called research tools; they are, however, also potentially suitable as medicaments. The remaining compounds of formula I and their salts are valuable intermediates.

Objects of the present invention are the compounds of general formula I and salts thereof per se, their manufacture and intermediates for their manufacture, the use of compounds of general formula Ia and of salts thereof as research tools and as medicaments or for the manufacture of medicaments, furthermore compounds of general formula Ia and salts thereof for use as therapeutically active substances, and medicaments containing a compound of general formula Ia or a salt thereof and the production of such medicaments.

DETAILED DESCRIPTION OF THE INVENTION

The present invention is concerned with tri- and tetracyclic compounds, primarily compounds of the general formula

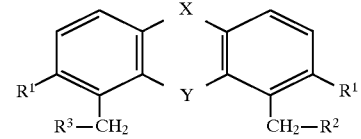

wherein X signifies a group of the formula

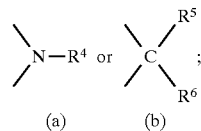

Y signifies oxygen or sulphur;

$R^1$ signifies hydrogen or lower alkoxy;

$R^2$ signifies protected amino, amino or a residue of the formula —NH—$R^7$ (c);

$R^3$ signifies carboxyl, functionally modified carboxyl or a residue of the formula —CO—$R^8$ (d);

$R^4$ signifies lower alkyl, aryl, aryl-lower alkyl, hydrogen or acyl;

$R^5$ and $R^6$ each signify lower alkyl, aryl or aryl-lower alkyl; and $R^7$ and $R^8$ are each individually a residue of an amino acid or a chain of up to 20 amino acid residues, whereby the amino acid residue or the amino acid residues can be protected or $R^7$ and $R^8$ together signify a residue of an amino acid or a chain of up to 20 amino acid residues whereby the amino acid residue or the amino acid residues can be protected, and whereby the molecule contains in total a maximum of 20 amino acid residues, and salts thereof.

The compounds of general formula I and their salts are novel. Those in which $R^2$ signifies a residue of formula (c), $R^3$ signifies a residue of formula (d) and $R^7$ and $R^8$ together signify a residue of an amino acid or a chain of up to 20 amino acid residues, i.e. compounds of the general formula

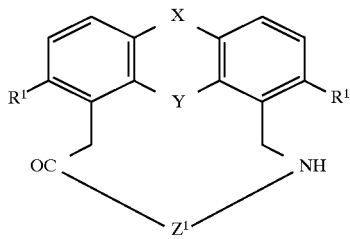

Ia wherein X, Y and $R^1$ have the above significance and $Z^1$ signifies a residue of an amino acid or a chain of up to 20 amino acid residues, and salts thereof, especially those in which the amino acid residue or the chain of amino acid residues does not contain protecting group(s), are valuable aids in the determination of biologically active peptide sequences and are therefore so-called research tools; they are, however, also potentially suitable as medicaments. The remaining compounds of formula I and their salts are valuable intermediates.

Objects of the present invention are the compounds of general formula I and salts thereof per se, their manufacture and intermediates for their manufacture, the use of compounds of general formula Ia and of salts thereof as research tools and as medicaments or for the manufacture of medicaments, furthermore compounds of general formula Ia and salts thereof for use as therapeutically active substances, and medicaments containing a compound of general formula Ia or a salt thereof and the production of such medicaments.

The term "lower alkyl" embraces straight-chain or branched saturated hydrocarbon residues with up to 7, preferably up to 4, carbon atoms such as methyl, ethyl, n-propyl, isopropyl, n-butyl, isobutyl, tert.butyl and the like. The term "lower alkoxy" embraces alkyloxy groups in the sense of the above description of the term "lower alkyl", such as methoxy, ethoxy, n-butoxy, and the like. The term "aryl" embraces the phenyl residue and substituted phenyl residues, especially mono- or disubstituted phenyl residues, with lower alkyl or lower alkoxy groups or halogen atoms primarily coming into consideration as substituents. The term "halogen" denotes the four forms fluorine, chlorine, bromine and iodine unless indicated otherwise. The term "acyl" embraces residues of aliphatic and aromatic carboxylic acids, primarily on the one hand lower alkanoyl groups such as acetyl, propionyl, butyryl or the like, which can be substituted, for example by carboxy or lower alkoxycarbonyl, as is the case e.g. in 4-carboxybutyryl, 4-methoxycarbonylbutyryl or the like, and on the other hand the benzoyl group and substituted benzoyl groups, especially mono- or disubstituted benzoyl groups, with lower alkyl or alkoxy groups or halogen atoms primarily coming into consideration as substituents. As used herein, the term "aralykyl" refers to groups comprising a lower-alkyl residue substituted by one or more aryl or substituted aryl groups, such as, for example, phenylmethyl, phenylethyl, phenylpropyl, phenylisopropyl, phenyl-tertiary butyl, hydroxyphenyl methyl and the like. The term "functionally modified carboxyl" embraces residues of the formula —COOR$^9$ (e) in which R$^9$ can signify lower alkyl, substituted lower alkyl, aryl-lower alkyl, aroyl-lower alkyl or allyl; R$^9$ conveniently signifies methyl, tert.-butyl, phenacyl, trimethylsilylethyl, trichloroethyl, phenyl, pentafluorophenyl, benzyl, allyl or the like. The term "protected amino" embraces on the one hand residues such as phthalimido and the like and on the other hand residues of the formula —NH—R$^{10}$ (f) in which R$^{10}$ can signify benzyloxycarbonyl ("Z"), tert.butyloxycarbonyl ("Boc"), 9-fluorenylmethoxy-carbonyl ("Fmoc"), allyloxycarbonyl ("Alloc"), trimethylsilylethoxycarbonyl ("Teoc"), trichloroethoxycarbonyl ("Tcc"), o-nitrophenylsulphenyl ("Nps") and the like.

As amino acid residues there primarily come into consideration those which are derived from α-amino acids, especially from natural a-amino acids; the amino acid residues can be present not only in the L form, but also in the D form and they can be optionally protected. Where the form of the amino acid residue is not stated, the L-form is denoted unless otherwise stated. Hereinafter there is given a list of amino acids which, or the residues of which, are suitable for the purpose of the present invention, with the abbreviations corresponding to the relevant IUPAC Rules (Biochemistry 11, 1726 (1972)) and to generally usual practice.

| | |
|---|---|
| Ac$_3$c | 1-Aminocyclopropanecarboxylic acid |
| Ac$_4$c | 1-Aminocyclobutanecarboxylic acid |
| Ac$_5$c | 1-Aminocyclopentanecarboxylic acid |
| Ac$_6$c | 1-Aminocyclohexanecarboxylic acid |
| Ac$_7$c | 1-Aminocycloheptanecarboxylic acid |
| Aib | 2-Amino-2-methylpropionic acid |
| Ala | L-Alanine |
| D-Ala | D-Alanine |
| β-Ala | β-Alanine |
| Arg | L-Arginine |
| D-Arg | D-Arginine |
| Asn | L-Asparagine |
| D-Asn | D-Asparagine |
| Asp | L-Aspartic acid |
| D-Asp | D-Aspartic acid |
| D-Asp (ONa) | Sodium D-aspartate |
| C$_3$al | L-3-Cyclopropylalanine |
| C$_4$al | L-3-Cyclobutylalanine |
| C$_5$al | L-3-Cyclopentylalanine |
| C$_6$al | L-3-Cyclohexylalanine |
| Cys | L-Cysteine |
| D-Cys | D-Cysteine |
| Glu | L-Glutamic acid |
| D-Glu | D-Glutamic acid |
| Gln | L-Glutamine |
| D-Gln | D-Glutamine |
| Gly | Glycine |
| His | L-Histidine |
| D-His | D-Histidine |
| Hyp | 4-Hydroxy-L-proline |
| Ile | L-Isoleucine |
| alle | L-Alloisoleucine |
| D-Ile | D-Isoleucine |
| D-alle | D-Alloisoleucine |
| D-Itg | D-2-(Isothiazolyl)glycine |
| Leu | L-Leucine |
| D-Leu | D-Leucine |
| tert.-Leu | L-2-Amino-3,3-dimethylbutyric acid |
| D-tert.-Leu | D-2-Amino-3,3-dimethylbutyric acid |
| Lys | L-Lysine |
| P-Lys | D-Lysine |
| Lys (CHO) | N$^6$-Formyl-L-lysine |
| MeAla | N-Methyl-L-alanine |
| MeLeu | N-Methyl-L-leucine |
| MeMet | N-Methyl-L-methionine |
| Met | L-Methionine |
| D-Met | D-Methionine |
| Met(O) | L-Methionine sulphoxide |
| D-Met(O) | D-Methionine sulphoxide |
| Met(O$_2$) | L-Methionine sulphone |

-continued

| | |
|---|---|
| D-Met(O₂) | D-Methionine sulphone |
| Nal | L-3-(1-Naphthylalanine) |
| D-Nal | D-3-(1-Naphthylalanine) |
| Nle | L-Norleucine |
| D-Nle | D-Norleucine |
| Nva | L-Norvaline |
| D-Nva | D-Norvaline |
| Orn | L-Ornithine |
| D-Orn | D-Ornithine |
| Orn(CHO) | N$^5$-Formyl-L-ornithine |
| Phe | L-Phenylalanine |
| D-Phe | D-Phenylalanine |
| L-Phg | L-Phenylglycine |
| D-Phg | D-Phenylglycine |
| Pip | L-Pipecolinic acid |
| D-Pip | D-Pipecolinic acid |
| Pro | L-Proline |
| D-Pro | D-Proline |
| Sar | Sarcosine |
| Ser | L-Serine |
| D-Ser | D-Serine |
| Thr | L-Threonine |
| D-Thr | D-Threonine |
| Thz | L-Thiazolidine-4-carboxylic acid |
| D-Thz | D-Thiazolidine-4-carboxylic acid |
| Trp | L-Tryptophane |
| D-Trp | D-Tryptophane |
| D-Trp(CHO) | N$^{in}$Formyl-D-tryptophane |
| D-Trp(O) | D-3-(2,3-Dihydro-2-oxoindol-3-yl)alanine |
| Tyr | L-Tyrosine |
| D-Tyr | D-Tyrosine |
| Tza | L-3-(2-Thiazolyl)alanine |
| D-Tza | D-3-(2-Thiazolyl)alanine |
| Tzg | L-2-(Thiazolyl)glycine |
| D-Tzg | D-2-(Thiazolyl)glycine |
| Val | L-Valine |
| D-Val | D-Valine |

Suitable protecting groups for amino acids and, respectively, their residues are, for example, for the amino group (as is present e.g. also in the side-chain of lysine)

| | |
|---|---|
| Z | Benzyloxycarbonyl |
| Boc | tert.-Butyloxycarbonyl |
| Fmoc | 9-Fluorenylmethoxycarbonyl |
| Alloc | Allyloxycarbonyl |
| Teoc | Trimethylsilylethoxycarbonyl |
| Tcc | Trichloroethoxycarbonyl |
| Nps | o-Nitrophenylsulphenyl; | for the carbonyl group (as is present e.g. also in the side-chain of aspartic acid and glutamic acid) by conversion into corresponding esters with the alcohol components

| | |
|---|---|
| tBu | tert.- Butyl |
| Bzl | Benzyl |
| Me | Methyl |
| Ph | Phenyl |
| Pac | Phenacyl |
| | Allyl |
| | Trimethylsilylethyl |
| | Trichloroethyl; | for the guanidine group (as is present, for example, in the side-chain of arginine)

| | |
|---|---|
| Pmc | 2,2,5,7,8-Pentamethylchroman-6-sulphonyl |
| Ts | Tosyl |
| Z | Benzyloxycarbonyl; | for the hydroxy group (as is present, for example, in the side-chain of threonine and serine)

| | |
|---|---|
| tBu | tert.-Butyl |
| Bzl | Benzyl |
| | Trityl; | and for the mercapto group (as is present, for example, in the side-chain of cysteine)

| | |
|---|---|
| tBu | tert.-Butyl |
| Bzl | Benzyl |
| | Trityl |
| | 2-Methoxytrityl. |

When X signifies a group of formula (a) in formula I or Ia, then $R^4$ conveniently signifies methyl, ethyl, hexyl, benzyl, hydrogen, 4-methoxycarbonylbutyryl or 4-carboxylbutyryl; where $R^4$ contains a carboxyl group, $R^3$ in formula I conveniently does not signify carboxyl. When X in formula I or Ia signifies a group of formula (b), then $R^5$ and $R^6$ both conveniently signify methyl.

Conveniently, the two symbols $R^1$ in formulae I and Ia both signify methoxy or both signify ethoxy.

The symbol $Z^1$ in formula Ia can conveniently contain up to 20 amino acid residues and preferably contain up to 14 amino acid residues and can have, for example, the following significances:

-Arg-
-Ala-
-Ala-Ala-
-Arg-Gln-
-Arg-Ser-
-Gln-Arg-
-Glu-Arg-
-Lys-Glu-
-Ser-Arg-
-Thr-Gly-
-Tyr-Phe-
-Leu-D-Try-D-Asp-
-Gly-Arg-Gly-
-Ile-Tyr-Ala-
-Leu-Tyr-Asp-
-Ala-Thr-Val-Gly-, -SEQ ID NO:1-,
-Arg-Gly-Asp-Val-, -SEQ ID NO:2-,
-Gly-Asp-Gly-Gly-, -SEQ ID NO:3-,
-Gly-Gly-Ala-Gly-, -SEQ ID NO:4-,
-Val-Arg-Lys-Lys-, -SEQ ID NO:5-,
-Ala-Arg-Gly-Asp-Phe-Pro-, -SEQ ID NO:6-,
-Glu-Arg-Gly-Asp-Val-Tyr-, -SEQ ID NO:7-,
-Ile-Ala-Arg-Gly-Asp-Phe-Pro-Asp-, -SEQ ID NO:8-,
-Val-Ala-Ala-Phe-Leu-Ala-Leu-Ala-, -SEQ ID NO:9-,
-Arg-Ile-Ala-Arg-Gly-Asp-Phe-Pro-Asp-Asp-, -SEQ ID NO:10-,
-Ala-Arg-Ile-Ala-Arg-Gly-Asp-Phe-Pro-Asp-Asp-Arg-, -SEQ ID NO:11-,

-Arg-Gly-Asp-Phe-, -SEQ ID NO:12-,
-Val-Arg-Lys-Lys, -SEQ ID NO:14-,
-Ile-Val-Arg-Lys-Lys-Pro-, -SEQ ID NO:15-,
-Gly-D-Arg-Lys-D-Ile-, -SEQ ID NO:16-, and
-Arg-Lys-Ile-Gln-Ile-Val-Arg-Lys-Lys-Pro-Ile-Phe-Lys-Lys-, -SEQ ID NO:17-.

Especially preferred compounds of formula Ia in the scope of the present invention are:

4,5-Cyclo-[acetyl-L-alanyl-L-arginyl-L-isoleucyl-L-alanyl-L-arginyl-glycyl-L-aspartyl-L-phenylalanyl-L-prolyl-L-aspartyl-L-aspartyl-L-arginyl--aminomethyl]-3,6-dimethoxy-9,9-dimethylxanthene(4,5-cyclo-[acetyl-SEQ ID NO:11-aminomethyl]-3,6-dimethyoxy-9,9-dimethylxanthene);

4,5-cyclo-[acetyl-L-arginyl-L-isoleucyl-L-alanyl-L-arginyl-glycyl-L-aspartyl-L-phenylalanyl-L-prolyl-L-aspartyl-L-aspartyl-aminomethyl]-3,6-dimethoxy-9,9-dimethylxanthene(4,5-cyclo-[acetyl-SEQ ID NO:10-aminomethyl]-3,6-dimethoxy-9,9-dimethylxanthene);

4,5-cyclo-[acetyl-L-isoleucyl-L-alanyl-L-arginyl-glycyl-L-aspartyl-L-phenylalanyl-L-prolyl-L-aspartyl-aminomethyl]-3,6-dimethoxy-9,9-dimethylxanthene(4,5-cyclo-[acetyl-SEQ ID NO:8-aminomethyl]-3,6-dimethoxy-9,9-dimethylxanthene);

4,5-cyclo-[acetyl-L-alanyl-L-arginyl-glycyl-L-aspartyl-L-phenylalanyl-L-prolyl-aminomethyl]-3,6-dimethoxy-9,9-dimethylxanthene(4,5-cyclo-[acetyl-SEQ ID NO:6-aminomethyl]-3,6-dimethoxy-9,9-dimethylxanthene);

4,5-cyclo-[acetyl-L-arginyl-glycyl-L-aspartyl-L-phenylalanyl-aminomethyl]-3,6-dimethoxy-9,9-dimethylxanthene(4,5-cyclo-[acetyl-SEQ ID NO:12-aminomethyl]-3,6-dimethoxy-9,9-dimethylxanthene);

4,5-cyclo-[acetyl-L-arginyl-glycyl-L-aspartyl-L-valyl-aminomethyl]-3,6-dimethoxy-9,9-dimethylxanthene(4,5-cyclo-[acetyl-SEQ ID NO:2-aminomethyl]-3,6-dimethoxy-9,9-dimethylxanthene);

10-methyl-4,6-cyclo-[acetyl-L-arginyl-glycyl-L-aspartyl-aminomethyl-L-valyl-aminomethyl]phenothiazine(10-methyl-4,6-cyclo-[acetyl-SEQ ID NO:2-aminomethyl]phenothiazine);

4,6-cyclo-[acetyl-L-arginyl-glycyl-L-aspartyl-L-valyl-aminomethyl]-3,7-diethoxy-10-ethyl-10H-dibenz[b,e][1,4]oxazine(4,6-cyclo-[acetyl-SEQ ID NO:2-aminomethyl]-3,7-diethoxy-10-ethyl-10H-dibenz[b,e][1,4]oxazine);

10-hexyl-3,7-dimethoxy-4,6-cyclo-[acetyl-L-arginyl-glycyl-L-aspartyl-L-valyl-aminomethyl]phenothiazine (10-hexyl-3,7-dimethoxy-4,6-cyclo-[acetyl-SEQ ID NO:2-aminomethyl]phenothizine); and 3,7-dimethoxy-10-methyl-4,6-cyclo-[acetyl-L-arginyl-glycyl-L-aspartyl-L-valyl-aminomethyl]phenothiazine(3,7-dimethoxy-10-methyl4,6-cyclo-[acetyl-SEQ ID NO:2-aminomethyl]phenothiazine).

Other preferred compounds of formula Ia are:

(S)-4,12-Dimethoxy-8-(3-guanidinopropyl)-17-methyl-1,15-imino-6,7,8,9,10,11-hexahydro-5H-dibenzol[b,k][1,5,8]-thiadiazacyclodecine-7,10-dione;

(S)-8-(3-guanidinopropyl)-17-hexyl-4,12-dimethoxy-1,15,-imino-6,7,8,9,10,11-hexahydro-5H-dibenzo[b,k][1,5,8]thiadiazacyclodecine-7,10-dione;

(S)-8-(3-guanidinopropyl)-17-methyl-1,15-imino-6,7,8,9,10,11-hexahydro-5H-dibenzo[b,k][1,5,8]thiadiazacyclodecine-7,10-dione;

10-hexyl-3,7-dimethoxy-4,6-cyclo-[acetyl-L-glutaminyl-L-arginyl-aminomethyl]phenothiazine;

10-hexyl-3,7-dimethoxy-4,6-cyclo[acetyl-L-arginyl-L-glutaminyl-aminomethyl]phenothiazine;

10-hexyl-3,7-dimethoxy-4,6-cyclo-[acetyl-L-seryl-L-arginyl-aminomethyl]phenothiazine;

10-hexyl-3,7-dimethoxy-4,6-cyclo-[acetyl-L-arginyl-L-seryl-aminomethyl]phenothiazine; and 10-hexyl-3,7-dimethoxy-4,6-cyclo[acetyl-glycyl-L-arginyl-glycyl-aminomethyl]phenothiazine.

The compounds of general formula I and their salts can be manufactured in accordance with the invention by a) reducing a compound of the general formula

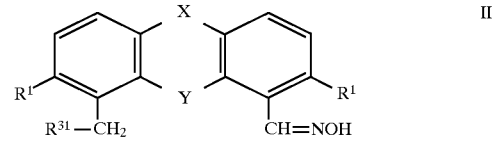

II wherein X, Y and $R^1$ have the above significance and $R^{31}$ signifies carboxyl or functionally modified carboxyl, or b) hydrolyzing a compound of the general formula

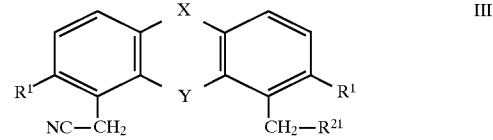

III wherein X, Y and $R^1$ have the above significance and $R^{21}$ signifies protected amino or amino, or c) converting the amino group in a compound of the general formula

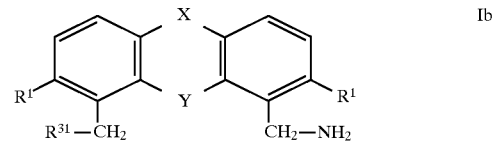

Ib wherein X, Y, $R^1$ and $R^{31}$ have the above significance, into a protected amino group; or d) converting the carboxyl group in a compound of the general formula

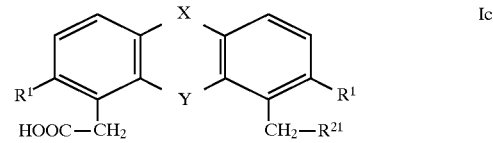

Ic wherein X, Y, $R^1$ and $R^{21}$ have the above significance, into a functionally modified carboxyl group; or e) cleaving off the protecting group in a compound of the formula

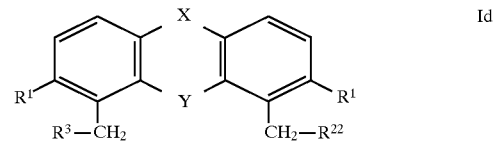

Id wherein X, Y, $R^1$ and $R^3$ have the above significance and $R^{22}$ signifies protected amino, or f) converting the functionally modified carboxyl group in a compound of the general formula

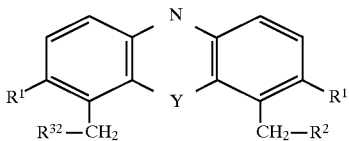

wherein X, Y, $R^1$ and $R^2$ have the above significance and $R^{32}$ signifies functionally modified carboxyl, into the carboxyl group; or g) removing the cleavable group from a compound of the general formula

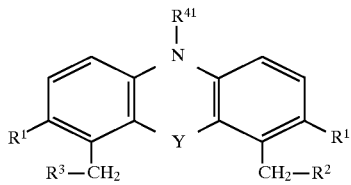

wherein Y, $R^1$, $R^2$ and $R^3$ have the above significance and $R^{41}$ signifies a cleavable aralkyl group,
or h) acylating a compound of the general formula

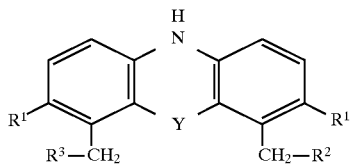

wherein Y, $R^1$, $R^2$ and $R^3$ have the above significance, and, if desired, esterifying a carboxyl group present in the introduced acyl group; or i) coupling a compound of the general formula

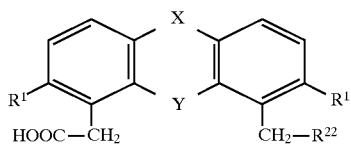

wherein X, Y, $R^1$ and $R^{22}$ have the above significance, with an optionally protected amino acid or with an optionally protected chain of up to 20 amino acids; or j) coupling a compound of the general formula

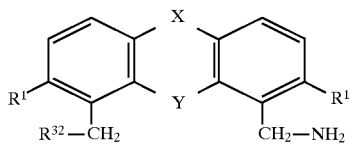

wherein X, Y, $R^1$ and $R^{32}$ have the above significance, with an optionally protected amino acid or with an optionally protected chain of up to 20 amino acids; or k) coupling a compound of the general formula

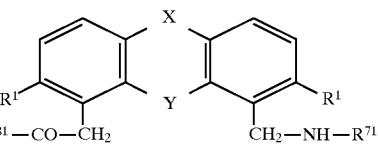

wherein X, Y and $R^1$ have the above significance and $R^{71}$ signifies hydrogen, an optionally protected residue of an amino acid or an optionally protected chain of amino acid residues and $R^{81}$ signifies hydrogen, an optionally protected residue of an amino acid or an optionally protected chain of amino acid residues, provided that at least one of $R^{71}$ and $R^{81}$ is different from hydrogen, with an optionally protected amino acid or with an optionally protected chain of amino acids, provided that in the two reaction components a maximum of 20 amino acid residues in total are present; or l) cyclizing a compound of the general formula

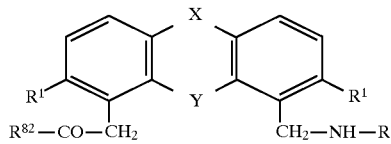

wherein X, Y and R have the above significance and $R^{72}$ signifies hydrogen, an optionally protected residue of an amino acid or an optionally protected chain of up to 20 amino acid residues and $R^{82}$ signifies hydrogen, an optionally protected residue of an amino acid or an optionally protected chain of up to 20 amino acid residues, provided that the molecule contains at least one amino acid residue and a maximum of 20 amino acid residues, or m) cleaving off the protecting group(s) from a compound of formula I which contains at least one protected amino acid residue; or n) converting a compound of formula I which contains a basic centre into a salt using an acid or converting a compound of formula I which contains an acidic centre into a salt using a base.

The reduction of a compound of formula II in accordance with process variant a) yields compounds of formula I in which $R^2$ signifies amino and $R^3$ signifies carboxyl or functionally modified carboxyl. It is effected using methods which are conventional and familiar to any person skilled in the art, conveniently by hydrogenation in the presence of a suitable catalyst such as palladium/charcoal.

The hydrolysis of a compound of formula III in accordance with process variant b) yields compounds of formula I in which $R^2$ signifies protected amino or amino and $R^3$ signifies carboxyl. It is likewise effected using methods which are conventional and familiar to any person skilled in the art, conveniently under strongly acidic conditions, e.g. by heating with concentrated hydrochloric acid, or under strongly alkaline conditions, e.g. by heating with about 5–7N sodium hydroxide solution or the like.

Process variant c) yields compounds of formula I in which $R^2$ signifies protected amino and $R^3$ signifies carboxyl or functionally modified carboxyl. The compound of formula Ib is treated with an agent which yields the desired protecting group using methods which are conventional and familiar to any person skilled in the art. Thus, di-tert.-butyl dicarbonate can be used, for example, for the introduction of a tert.-butyloxycarbonyl group (Boc), N-(9-fluorenylmethoxycarbonyl)-succinimide can be used, for example, for the introduction of a 9-fluorenylmethoxycarbonyl group (Fmoc), benzyl chloroformate can be used, for example, for the introduction of a benzyloxycarbonyl group (Z), and the like.

Process variant d) yields compounds of formula I in which $R^2$ signifies protected amino or amino and $R^3$ signifies functionally modified carboxyl. In this variant, a compound of formula Ic is appropriately esterified using methods which are conventional and familiar to any person skilled in the art. Thus, diazomethane can be used, for example, for the manufacture of a methyl ester, benzyl bromide in the presence of a suitable base such as 1,8-diazabicyclo[5.4.0]undec-7-ene (DBU) or benzyl alcohol in the presence of a suitable dehydrating agent such as dicyclohexylcarbodiimide and a suitable base such as 4-dimethylaminopyridine can be used for the manufacture of a benzyl ester, etc.

Compounds of formula I in which $R^2$ signifies amino are obtained in accordance with process variant e). In this variant, the protecting group is cleaved off from a compound of formula Id using methods which are conventional and familiar to any person skilled in the art. Thus, hydrazine hydrate can be used, for example, for the cleavage of a phthalimido group, trifluoroacetic acid can be used, for example, for the cleavage of a tert.-butyloxycarbonyl group (Boc), etc.

Process variant f) yields compounds of formula I in which $R^3$ signifies carboxyl and is effected using methods for the cleavage of an ester which are conventional and familiar to any person skilled in the art. Thus, the cleavage of a lower alkyl ester, e.g. a methyl ester, is conveniently effected by alkaline hydrolysis, for example using potassium hydroxide or sodium hydroxide in a mixture of water and the corresponding alcohol, the cleavage of a benzyl ester is conveniently effected by catalytic hydrogenation, e.g. in the presence of palladium/carbon, etc.

Compounds of formula I in which X signifies a residue of formula (a) and $R^4$ signifies hydrogen are obtained in accordance with process variant g). The cleavage of the group represented by the symbol $R^{41}$ in formula. If is effected using methods which are conventional and familiar to any person skilled in the art. The cleavable group is conveniently a benzyl group and this can be cleaved off, for example, by catalytic hydrogenation, with palladium/charcoal primarily coming into consideration as the hydrogenation catalyst.

Process variant h) yields compounds of formula I in which X signifies a residue of formula (a) and $R^4$ signifies acyl. The acylation of the compound of formula Ig is effected by treatment with a suitable acylating agent which yields the desired acyl residue using methods which are conventional and familiar to any person skilled in the art. Thus, for example, acetyl chloride or acetic anhydride is suitable for the introduction of an acetyl residue, benzoyl chloride or a correspondingly substituted benzoyl chloride is suitable for the introduction of a benzoyl residue or a substituted benzoyl residue, a corresponding dicarboxylic acid anhydride is suitable for the introduction of a carboxy-substituted lower alkanoyl residue (i.e. glutaric anhydride for the introduction of a 4-carboxybutyryl residue), etc.

The acylation is effected in the presence of a base, with inorganic bases such as sodium carbonate, sodium hydroxide or the like and/or organic bases such as triethylamine, 4-dimethylaminopyridine or the like coming into consideration depending on the nature of the compound of formula Ig to be acylated and on the nature of the acylating agent.

The esterification of a carboxyl group present in the introduced acyl group can be effected according to methods which are conventional and familiar to any person skilled in the art, e.g. using methyl iodide in the presence of a base such as 1,8-diazabicyclo[5.4.0]undec-7-ene.

Process variant i) yields compounds of formula I in which $R^2$ signifies protected amino, $R^3$ signifies a residue of formula (d) and $R^8$ signifies an optionally protected residue of an amino acid or an optionally protected chain of up to 20 amino acid residues; process variant j) yields compounds of formula I in which $R^3$ signifies functionally modified carboxyl, $R^2$ signifies a residue of formula (c) and $R^7$ signifies an optionally protected residue of an amino acid or an optionally protected chain of up to 20 amino acid residues; process variant k) yields compounds of formula I in which $R^2$ signifies a residue of formula (c), $R^3$ signifies a residue of formula (d) and $R^7$ and $R^8$ each signify an optionally protected residue of an amino acid or an optionally protected chain of amino acid residues, the molecule containing a maximum of 20 amino acid residues in total; and process variant l) yields compounds of formula I in which $R^2$ signifies a residue of formula (c), $R^3$ signifies a residue of formula (d) and $R^7$ and $R^8$ together signify an optionally protected residue of an amino acid or an optionally protected chain of up to 20 amino acid residues.

Methods which are conventional in peptide chemistry and familiar to any person skilled in the art are used in carrying out these process variants. One of these methods is solid phase synthesis which can be used where in the desired product one of the amino acid residues contains a terminal carboxyl group or a carboxyl group in the side-chain or the group denoted by the symbol X contains a carboxyl group; suitable carriers are, for example, p-hydroxymethyl-phenoxy-polystyrene resin, 4-(2',4'-dimethoxyphenyl-hydroxymethyl)phenoxy-polystyrene resin and the like.

When a compound of formula Ih is used in process variant i), then this is coupled with an amino acid component having a free amino group at the N-terminal and a protected carboxyl group at the C-terminal. When a compound of formula Ii is used in process variant j), then this is coupled with an amino acid component having a protected amino group at the N-terminal and a free carboxyl group at the C-terminal or with an activated derivative thereof. The compounds of formula Ij used as starting products in process variant k) contain a free amino group or a free carboxyl group depending on the nature of the residues $R^{71}$ and $R^{81}$; in the first case they are coupled with an amino acid component having a protected amino group at the N-terminal and having a free carboxyl group at the C-terminal or with an activated derivative. thereof, and in the latter case they are coupled with an amino acid component having a free amino group at the N-terminal and protected carboxyl group at the C-terminal. In the cyclization of a compound of formula Ik according to process variant l), a free carboxyl group or an activated derivative thereof and a free amino group are coupled with one another with the formation of an amide bond.

A wide variety of activating reagents which are conventional in peptide chemistry can be used to carry out this coupling, such as e.g. O-benzotriazol-1-yl-N,N,N',N'-tetramethyluronium hexafluorophosphate (HBTU), O-(1,2-dihydro-2-oxo-1-pyridyl)-N,N,N',N'-tetramethyluronium tetrafluoroborate (TPTU), 2-(1H-benzotriazol-1-yl)-1.1,3,3-tetramethyluronium tetrafluoroborate (TBTU), 1-hydrcombination with (HOBT) in combination with N,N-dicyclohexylcarbodiimide and the like.

When a compound of formula Ih or Ii or Ij is coupled with an optionally protected chain of amino acid residues in accordance with process variant i) or j) or k), then this can also be effected stepwise.

By cleaving off the protecting group(s) from a compound of formula I which contains at least one protected amino acid residue there is obtained in accordance with process variant m) a corresponding compound of formula I which contains 1–20 amino acid residues in which the amino acid residue or the amino acid residues does/do not contain protecting group(s). The cleavage of the protecting group(s) is effected according to methods which are conventional and familiar to any person skilled in the art, of course while taking into consideration the nature of the protecting group(s). Thus, the protecting groups referred to above can be cleaved off, for example, as follows:

| | |
|---|---|
| Z: | Catalytic hydrogenation in the presence of Pd/C in a lower alkanol such as methanol or ethanol. |
| Boc: | Using trifluoroacetic acid/methylene chloride (1:1) or using saturated hydrogen chloride solution in ethyl acetate. |
| Fmoc: | Using piperidine or 1,8-diazabicyclo[5.4.0]-undec-7-ene in dimethylformamide. |
| Alloc: | Using palladium-tetrakis-triphenylphosphine in tetrahydrofuran/dimethyl sulphoxide/0.1 N hydrochloric acid. |
| Teoc: | Using caesium fluoride or tetrabutylammonium fluoride in dimethylformamide or the like. |
| Tcc: | Using zinc in glacial acetic acid or methanol. |
| Nps: | Using sodium rhodanide or potassium rhodanide in a slightly acidic medium. |
| tBu: | Using trifluoroacetic acid/methylene chloride (1:1). |
| Bzl: | By catalytic hydrogenation in the presence of Pd/C in a lower alkanol such as methanol or ethanol. |
| Me: | Using lithium hydroxide in tetrahydrofuran/methanol/water (3:1:1). |
| Ph: | Using sodium peroxide at pH 10.5. |
| Pac: | Using zinc in glacial acetic acid or methanol or using sodium thiophenolate in dimethylformamide. |
| Allyl: | Using palladium-bis-triphenylphosphine dichloride and tributyltin hydride or using palladium-tetrakis-triphenylphosphine in tetrahydrofuran/dimethyl sulphoxide/0.5 N hydrochloric acid. |
| Trimethyl-silyl ether: | Using caesium fluoride or tetrabutylammonium fluoride in dimethylformamide or the like. |
| Trichloro-ethyl: | Using zinc in glacial acetic acid or methanol. |
| Pmc: | Using aqueous trifluoroacetic acid |
| Ts: | Using sodium in liquid ammonia or liquid hydrogen fluoride. |

In an analogous manner, compounds of formula I which contain an amino acid residue having a terminal carboxyl group or a carboxyl group in the side-chain or in which the group denoted by the symbol X contains a carboxyl group and which are manufactured by solid phase synthesis on a p-hydroxymethylphenoxy-polystyrene resin, on a 4-(2',4'-dimethoxyphenol-hydroxymethyl)phenoxy-polystyrene resin or the like can be cleaved off from the carrier resin, for example using "Field's reagent", i.e. a mixture of 82.5% trifluoroacetic acid, 5% phenol, 5% water, 5% thioanisole and 2.5% 1,2-ethanedithiol.

In accordance with process variant n), a compound of formula I which contains a basic centre or an acidic centre can be converted into a salt using an acid or a base, which can be effected according to methods which are conventional and familiar to any person skilled in the art. Acids which can be used are inorganic acids such as hydrochloric acid, sulphuric acid, phosphoric acid or the like or organic acids such as trifluoroacetic acid, methanesulphonic acid, p-toluenesulphonic acid or the like and bases which can be used are inorganic bases such as potassium hydroxide, sodium hydroxide or the like or organic bases such as triethylamine, dimethylaminopyridine, or the like.

The starting products which are required for process variants a) and b) are novel and are also an object of the present invention. They can be prepared in accordance with the following Reaction Scheme in which $X^1$ signifies a residue of formula (a), wherein $R^4$ signifies lower alkyl, aryl or aryl-lower alkyl, or a residue of formula (b); the two symbols $R^{11}$ each signify lower alkyl or together signify lower alkylene; $R^{12}$ signifies lower alkyl, aryl or aryl-lower alkyl; $R^{13}$ signifies a protecting group such as tert.-butyl-dimethyl-silyl (TBDMS), tert.-butyl-diphenylsilyl (TBDPS), 2-methoxyethoxymethyl (Mem) or the like; $R^{14}$ signifies hydrogen or a protecting group such as tert.-butyloxycarbonyl (Boc), 9-fluorenylmethoxycarbonyl (Fmoc) or the like; Phth signifies the phthalimido group; and Y and $R^1$ have the above significance.

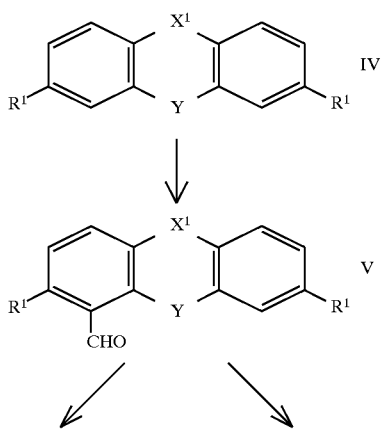

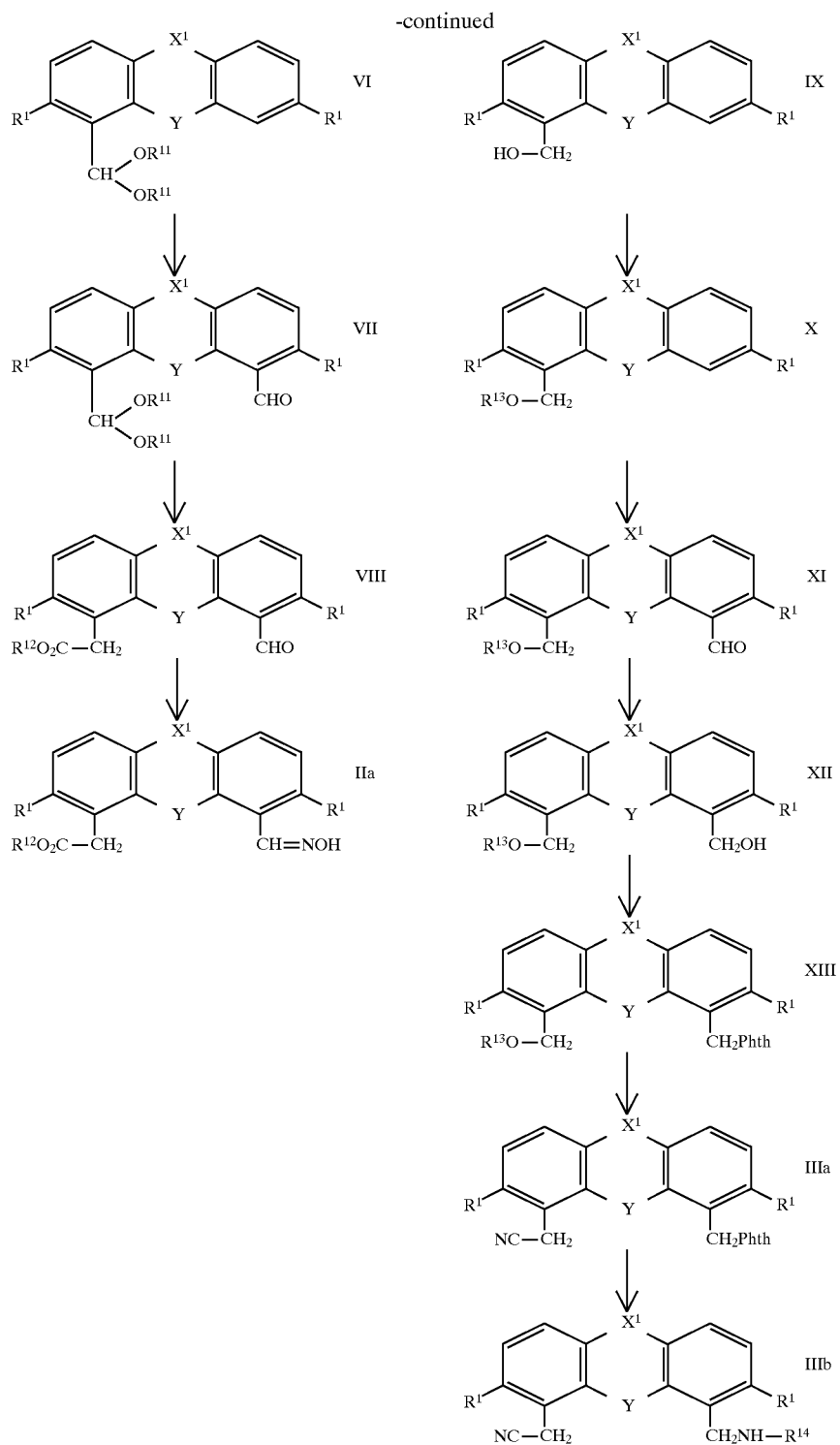

The compound of formula IV are known or can be prepared readily in analogy to the preparation of the known compounds according to methods which are conventional and familiar to any person skilled in the art; moreover, some of the Examples hereinafter contain detailed information concerning the preparation of certain compounds of formula IV which have hitherto not been described.

The individual steps of the foregoing Reaction Scheme are explained in more detail hereinafter.

IV→V

The compound of formula IV is conveniently reacted with somewhat more than the equimolar amount of butyllithium in ether/hexane. N-Formylpiperidine is conveniently used for the introduction of the formyl group.

V→VI

The formyl group is converted into an acetal group in the usual manner, conveniently using triethyl orthoformate or the like.

VI→VII

The compound of formula VI is conveniently reacted with somewhat more than the equimolar amount of butyllithium in ether/tetrahydrofuran/hexane. Again, N-formylpiperidine is conveniently used for the introduction of the formyl group.

VII→VIII

The compound of formula VII is conveniently reacted with methyl (methylthiomethyl) sulphoxide in the presence of a base such as Triton B. The resulting product is then conveniently treated with a solution of hydrochloric acid in an alcohol of the formula $R^{12}$—OH. In the resulting compound the formyl group is formed from the acetyl group of the compound of formula VII and the ester group ($R^{12}O_2C$—$CH_2$—) is formed from the formyl group of the compound of formula VII.

VIII→IIA

The aldehyde of formula VII is conveniently converted into the corresponding oxime using hydroxylamine hydrochloride in the presence of sodium acetate.

V→IX

The reduction of the formyl group to the hydroxymethyl group is conveniently effected using lithium borohydride in tetrahydrofuran.

IX→X

The hydroxymethyl group is protected in the usual manner, for example with tert.-butyldimethylchlorosilane/imidazole, with tert.-butyldiphenylsilyl chloride/triethylamine/dimethylaminopyridine, with 2-methoxyethoxymethyl chloride/butyllithium etc.

X→XI

The formylation is effected analogously to that described for step VI→VII.

XI→XII

The reduction of the formyl group to the hydroxymethyl group is effected analogously to that described for step V→IX.

XII→XIII

The replacement of the hydroxy group by the phthalimido group is conveniently effected according to the method described by Mitsunobu (Synthesis 1981, 1) using phthalimide/triphenylphosphine/dimethyl azodicarboxylate.

XIII→IIIa

Conveniently, the compound of formula XIII is firstly converted into the corresponding bromomethyl compound; when $R^{13}$ signifies methoxyethoxyethyl, this is conveniently effected using hydrogen bromide and when $R^{13}$ signifies tert.-butyldimethylsilyl or tert.-butyldiphenylsilyl this is conveniently effected using boron tribromide. The bromomethyl compound is then conveniently reacted with sodium cyanide.

III→IIIb

By cleavage of the phthalimido group, e.g. using hydrazine hydrate and subsequent hydrolysis or saponification, there is obtained a compound of formula IIIb in which $R^{14}$ signifies hydrogen. If desired, this can then be converted according to conventional methods into the corresponding compound of formula IIIb in which $R^{14}$ signifies a protecting group such as Boc, Fmoc or the like.

If desired, in a compound of formula VII, VIII, IIa, XI, XIII, IIIa or IIIb in which X signifies a residue of formula (a) and $R^4$ signifies a readily cleavable aralkyl group, this group can be cleaved off and, if desired, replaced by an acyl group, whereafter a carbonyl group present in the introduced acyl group can be esterified if desired. Furthermore, in a compound of formula VIII or IIa an ester cleavage (optionally followed by an esterification of the resulting carboxylic acid with a different alcohol) or a transesterification can be effected.

The compounds of formulae V to XIII are novel and are also objects of the present invention.

The compounds of formula Ia are amino acid derivatives in which the amino acid or the amino acid sequence is strongly restricted with respect to its conformational flexibility.

In particular, in compounds of formula Ia in which $Z^1$ signifies a chain of 2 or 4 amino acid residues the amino acid sequences are preferably present in a β-turn or β-turn-like conformation (see G. D. Rose, L. Gierasch, J. A. Smith, Advances in Protein Chemistry 1985, 37, 1–109 and P. Y. Chou, G. D. Fasman, J. Mol. Biol. 1977, 115 135–175).

The compounds of formula Ia, especially those in which the amino acid residue or the chain of amino acid residues dose not contain protecting group(s), are suitable as mimetics of exposed regions of proteins in order to elucidate their role with respect to interactions with other proteins (receptors, enzymes or the like). In particular, amino acid sequences having biological activity can be determined using compounds of formula Ia. They are accordingly suitable as research tools in connection with the preparation of biologically active peptide sequences. Starting from proteins having a known three dimensional structure, exposed loop-shaped peptide sequences can be detected. Such peptide sequences can then lead to pharmacologically valuable compounds. For example, compounds of formula Ia in which X is or contains the sequence -Arg-Gly-Asp-Phe-[SEQ ID NO:12] or Arg-Gly-Asp-Val-[SEQ ID NO:2] are active as fibrinogen antagonists, i.e. they inhibit the binding of the fibrinogen to fibrinogen receptors of the blood platelets (glycoprotein IIb/IIIa), which can be demonstrated as follows:

The glycoprotein IIb/IIIa is obtained from Triton X-100 extracts of human blood platelets and purified by lectin affinity chromatography (Analytical Biochemistry 151, 1985, 169–177) and chromatography on an Arg-Gly-Asp-Ser [SEQ ID NO:13] affinity column (Science 231, 1986, 1559–62). The thus-obtained receptor protein is bonded to microtitre plates. The specific binding of fibrinogen to the immobilized receptor is determined with the aid of an ELISA system ("enzyme-linked immunosorbent assay"). The $IC_{50}$ is that concentration of a test substance which is required to inhibit the binding of fibrinogen to the immobilized receptor by 50%. The following Table contains, for various compounds of formula I which fulfill the aforementioned structural criteria, data showing by which factor their $IC_{50}$ differs ("relative $IC_{50}$") from that determined for the standard co-investigated L-arginyl-glycyl-L-aspartyl-L-serine [SEQ ID NO:13] (for which the relative $IC_{50}$ is given as 1.0000).

| Test substance | Relative $IC_{50}$ |
| --- | --- |
| A | 0.0124 |
| B | 0.0062 |
| C | 0.0077 |
| D | 0.1553 |
| E | 0.0483 |
| F | 0.68 |
| G | 1.46 |
| H | 0.62 |
| I | 7.51 |
| Standard | 1.0000 |

A: 4,5-Cyclo-[acetyl-L-alanyl-L-arginyl-L-iso-luecyl-L-alanyl-L-arginyl-glycyl-L-aspartyl-L-

-continued

| | |
|---|---|
| | phenylalanyl-L-prolyl-L-aspartyl-L-aspartyl-L-arginyl-aminomethyl]-3,6-dimethoxy-9,9-dimethylxanthene (4,5-cyclo-[acetyl-SEQ ID NO: 11-aminomethyl]-3,6-dimethoxy-9,9-dimethylxanthene) |
| B: | 4,5-Cyclo-[acetyl-L-arginyl-L-isoleucyl-L-alanyl-L-arginyl-glycyl-L-aspartyl-L-phenyl-alanyl-L-prolyl-L-aspartyl-L-aspartyl-aminomethyl]-3,6-dimethoxy-9,9-dimethylxanthene (4,5-cyclo-[acetyl-SEQ ID NO: 10-aminomethyl-3,6-dimethoxy-9,9-dimethylxanthene) |
| C: | 4,5-Cyclo-[acetyl-L-isoleucyl-L-alanyl-L-arginyl-glycyl-L-aspartyl-L-phenylalanyl-L-prolyl-L-aspartyl-aminomethyl]-3,6-dimethoxy-9,9-dimethylxanthene (4,5-cyclo-[acetyl-SEQ ID NO: 8-aminomethyl)-3,6-dimethoxy-9,9-dimethylxanthene) |
| D: | 4,5-Cyclo-[acetyl-L-alanyl-L-arginyl-glycyl-L-aspartyl-L-phenylalanyl-L-prolyl-aminomethyl]-3,6-dimethoxy-9,9-dimethylxanthene (4,5-cyclo-[acetyl-SEQ ID NO: 6-aminomethyl]-3,6-dimethoxy-9,9-dimethylxanthene) |
| E: | 4,5-Cyclo-[acetyl-L-arginyl-glycyl-L-aspartyl-L-phenylalanyl-aminomethyl]-3,6-dimethoxy-9,9-dimethylxanthene (4,5-cyclo-[acetyl-SEQ ID NO: 12-aminomethyl]-3,6-dimethoxy-9,9-dimethylxanthene) |
| F: | 4,5-Cyclo-[acetyl-L-arginyl-glycyl-L-aspartyl-L-valyl-aminomethyl]-3,6-dimethoxy-9,9-dimethylxanthene (4,5-cyclo-[acetyl-SEQ ID NO: 2-aminomethyl]-3,6-dimethoxy -9,9-dimethylxanthene) |
| G: | 10-Methyl-4,6-cyclo-[acetyl-L-arginyl-glycyl-L-aspartyl-L-valyl-aminomethyl]phenothiazine (10-methyl-4,6-cyclo-[acetyl-SEQ ID NO: 2-aminomethyl]phenothiazine) |
| H: | 4,6-Cyclo-[acetyl-L-arginyl-glycyl-L-aspartyl-L-valyl-aminomethyl]-3,7-diethoxy-10-ethyl-10H-dibenz[b,e][1,4]oxazine (4,6-cyclo-[acetyl-SEQ ID NO: 2-aminomethyl]-3,7-diethoxy-10-ethyl-10H-dibenz[b,e][1,4]oxazine) |
| I: | 10-Hexyl-3,7-dimethoxy-4,6-cyclo-[acetyl-L-arginyl-glycyl-L-aspartyl-L-valyl-aminomethyl-]phenothiazine) (10-hexyl-3,7-dimethoxy-4,6-cyclo-[acetyl-SEQ ID NO: 2-aminomethyl]phenothiazine) |

From the above it will be evident that the compounds of formula Ia, especially those in which the amino acid residue or the chain of amino acid residues dose not contain protecting group(s), can be used not only as research tools, but are also potentially suitable as medicaments, in mammals, both human and non-human, with the respective therapeutic applicability depending primarily on the nature, number and sequence of amino acid residues present in the molecule. Thus, for example, the previously discussed compounds A to I, which are active as fibrinogen antagonists, and pharmaceutically usable salts thereof can be used to prevent or control the formation of blood platelet thrombi and thus for the control or prevention of illnesses such as thrombosis, stroke, cardiac infarct, inflammation and arteriosclerosis in mammals, both human and non-human.

Accordingly, as mentioned earlier, medicaments containing a compound of formula Ia or a pharmaceutically usable salt thereof and a pharmaceutically usable adjuvant are also an object of the present invention, furthermore also a process for the manufacture of such medicaments in unit dosage forms which comprises bringing one or more compounds of formula Ia or pharmaceutically usable salts thereof and, if desired, one or more other therapeutically valuable substances into a galenical administration form together with one or more pharmaceutically usable adjuvants. The medicaments can be administered enterally, e.g. orally in the form of tablets, coated tablets, dragées, hard and soft gelatine capsules, solutions, emulsions or suspensions, or rectally, e.g. in the form of suppositories, or as a spray. The administration can, however, also be effected parenterally, e.g. in the form of injection solutions.

The active substances can be mixed with pharmaceutically inert, inorganic or organic excipients for the manufacture of tablets, coated tablets, dragées and hard gelatine capsules. Lactose, corn starch or derivatives thereof, talc, stearic acid or its salts can be used e.g. as such excipients for tablets, dragées and hard gelatine capsules. Suitable excipients for soft gelatine capsules are e.g. vegetable oils, waxes, fats, semi-solid and liquid polyols; depending on the nature of the active substance or active substances no excipients are generally required in the case of soft gelatine capsules. Suitable excipients for the manufacture of solutions and syrups are e.g. water, polyols, saccharose, invert sugar and glucose; suitable excipients for injection solutions are e.g. water, alcohols, polyols, glycerol and vegetable oils and suitable excipients for suppositories are e.g. natural or hardened oils, waxes, fats and semi-liquid or liquid polyols. The pharmaceutical preparations can, also contain preservatives, solubilizers, colorants, flavorants, salts for varying the osmotic pressure, coating agents or antioxidants.

Finally, the use of compounds of formula Ia and of salts thereof as research tools for determining biologically active peptide sequences and the use of compounds of formula Ia and of pharmaceutically usable salts thereof as medicaments or for the manufacture of medicaments, for example the use of the hereinbefore discussed compounds A to I, which are active as fibrinogen antagonists, and of pharmaceutically usable salts thereof for the prevention or control of the formation of blood platelet thrombi or for the manufacture of corresponding medicaments are objects of the invention.

In the following Examples, which illustrate the invention in more detail but are not intended to limit its scope in any manner, all temperatures are given in degrees Celsius. Unless otherwise stated, all Examples were carried out as written.

EXAMPLE 1.1.1a

A solution of 10.8 g (40 mmol) of 3,6-dimethoxy-9,9-dimethylxanthene [prepared according to Coll. Czech. Chem. Commun. 24 (1959), 1061] in absolute ether was cooled to 0° to −5°. 50 ml of a 1.6M butyllithium solution (in hexane) were added dropwise while stirring. 9.04 g (80 mmol) of N-formylpiperidine were added dropwise after 15 hours and the mixture was subsequently stirred at 0° for 1 hour and at room temperature for 2 hours. Thereafter, the reaction mixture was poured into acidic (pH 1) ice-water, whereupon it was extracted twice with 200 ml of ether each time. The combined extracts were washed neutral with ice-water, dried over $Na_2SO_4$ and concentrated. The residual oil was purified on silica gel with hexane/ethyl acetate and thereafter crystallized from t-butyl methyl ether/hexane. There were obtained 7.1 g of 3,6-dimethoxy-9,9-dimethylxanthene-4-carboxaldehyde of m.p. 84.5°–86°; IR 2966, 1688, 1637, 1605, 1568, 1515, 1486 $cm^{-1}$.

EXAMPLE 1.1.1.b

A solution of 24.15 g of 3,6-dimethoxy-9,9-dimethylxanthene-4-carboxaldehyde in 50 ml of absolute ethanol was treated with 50 ml of triethyl orthoformate. After the addition of 100 mg of p-toluenesulphonic acid monohydrate the mixture was boiled under reflux for 1 hour, then cooled and poured into ice-cold sodium bicarbonate solution, whereupon the mixture was extracted twice with 200 ml of ether each time. The combined extracts were washed neutral with water, dried over $Na_2SO_4$ and concentrated. The residue was purified on silica gel with hexane/ethyl acetate, whereby there were obtained 19.6 g of 3,6-dimethoxy-9,9-dimethylxanthene-4-carboxaldehyde dimethyl acetal as a pale yellow oil which crystallized slowly; m.p. 60°–62°, IR 2972, 1606, 1572, 1490 $cm^{-1}$.

EXAMPLE 1.1.1.c 4.46 g (12 mmol) of 3,6-dimethoxy-9,9-dimethylxanthene-4-carboxaldehyde dimethyl acetal were dissolved in a mixture of 43 ml of ether and 10 ml of THF. The solution obtained was cooled to −10° and treated dropwise with 11.25 ml (18 mmol) of a 1.6M butyllithium solution (in hexane). 2.17 g (19.2 mmol) of N-formylpiperidine were added after 6 hours. After a further hour the mixture was poured into ice-water, whereupon it was extracted with ether. The extracts were washed with ice-water, dried over $Na_2SO_4$ and concentrated. The residue was crystallized from hexane/ether, whereby 3,6-dimethoxy-9,9-dimethylxanthene-4,5-dicarboxaldehyde-4-diethyl acetal of m.p. 144°–145° was obtained; IR 1685, 1624, 1603, 1568, 1465, 1390 $cm^{-1}$.

EXAMPLE 1.1.1.d

A solution of 2.15 g (5.37 mmol) of 3,6-dimethoxy-9,9-dimethylxanthene-4,5-dicarboxaldehyde-4-diethyl acetal in 15 ml of THF was treated firstly with 0.8 g (6.44 mmol) of methyl (methylthiomethyl) sulphoxide and thereafter with 0.63 ml of a Triton-B solution (35% in methanol). The mixture was heated under reflux for 3 hours, then cooled and finally poured into ice-water, whereupon it was extracted with 2*50 ml of ether. The extracts were washed neutral with water, dried over magnesium sulphate and concentrated. The residue remaining (2.66 g) was treated with 30 ml of a ethanolic hydrochloric acid solution (20%). The mixture was stirred at room temperature for 3 hours and then poured into ice-cold saturated sodium bicarbonate solution, whereupon is was extracted with 2*50 ml of ether. The ethereal phase was washed neutral with water, dried over magnesium sulphate and concentrated. The residue was chromatographed on silica gel with hexane/ethyl acetate and thereafter recrystallized from hexane/ethyl acetate, whereby 1.05 g of methyl 3,6-dimethoxy-9,9-dimethyl-5-formylxanthene-4-acetate of m.p. 142°–143.5° were obtained; IR 2964, 1730, 1681, 1625, 1602, 1573 $cm^{-1}$.

EXAMPLE 1.1.1.e 5 g (13.5 mmol) of methyl 3,6-dimethoxy-9,9-dimethyl-5-formylxanthene-4-acetate were dissolved in a mixture of 75 ml of methanol, 75 ml of THF and 20 ml of water. After the addition of 1.66 g of sodium acetate and 1.4 g of hydroxylamine hydrochloride the mixture was stirred at room temperature overnight and then diluted with 200 ml of water. The precipitated solid was filtered off, washed with water and dried, whereby 4.95 g of methyl 3,6-dimethoxy-9,9-dimethyl-5-[(hydroximino)methyl]xanthene-4-acetate were obtained as a white powder of m.p. 234°–236°; IR 1743, 1629, 1604, 1582, 1498 $cm^{-1}$.

4 g (10.4 mmol) of methyl 3,6-dimethoxy-9,9-dimethyl-5-[(hydroximino)methyl]xanthene4-acetate were suspended in 100 ml of methanol, whereupon 60 ml of a 20% methanolic hydrochloric acid solution were added. The mixture was left to stand at room temperature for 2 hours, then treated with 1 g of palladium/charcoal (10%) and stirred under hydrogen for 20 hours. Thereafter, the catalyst was filtered off and the filtrate was evaporated to dryness. The crude product remaining as the residue was recrystallized from methanol/ether, whereby 2.95 g of colourless methyl 5-aminomethyl-3,6-dimethoxy-9,9-dimethylxanthene-4-acetate hydrochloride of m.p. 261°–262° were obtained; IR 3233, 2967, 2838, 1724, 1606 and 1495 $cm^{-1}$.

EXAMPLE 1.1.2

A solution of 1 g (2.45 mmol) of methyl 5-aminomethyl-3,6-dimethoxy-9,9-dimethylxanthene-4-acetate hydrochloride in 30 ml of dioxan was diluted with 15 ml of water and adjusted to pH 9 at 0° with 1N sodium hydroxide solution. Thereafter, a solution of 0.8 g (3.7 mmol) of di-tert-butyldicarbonate in 2 ml of dioxan was added dropwise. The mixture was stirred at 0° for 2 hours and then poured into ice-water, whereupon it was extracted three times with methylene chloride. The combined extracts were washed firstly with water and then with saturated sodium chloride solution, dried over sodium sulphate and concentrated, whereby 1.47 g of methyl 5-[(1-tert-butylformamido)methyl]-3,6-dimethoxy-9,9-dimethylxanthene-4-acetate remained as the residue in the form of a colourless oil; IR 3462, 3425, 2971, 2838, 1741, 1714, 1605, 1495 $cm^{-1}$.

EXAMPLE 1.1.3

A solution of 4 g (8.48 mmol) of methyl 5-[(1-tert-butylformamido)methyl]-3,6-dimethoxy-9,9-dimethylxanthene-4-acetate in 80 ml of methanol was treated with 25 ml of 1N potassium hydroxide solution. The mixture was heated to 50° for 2 hours, then treated with a further 9 ml of 1N potassium hydroxide solution, thereupon stirred at 50° for 5 hours and then cooled. The pH was adjusted to 1 with 2N hydrochloric acid, whereupon the mixture was extracted three times with 180 ml of methylene chloride each time. The combined organic extracts were washed with dilute sodium chloride solution, dried over magnesium sulphate and freed from solvent, whereby 3.3 g of 5-[(1-tert-butoxyformamido)methyl]-3,6-dimethoxy-9,9-dimethylxanthene-4-acetic acid remained as the residue in the form of a colourless powder; IR 2970, 1714, 1629, 1606, 1494 $cm^{-1}$.

EXAMPLE 1.1.4

A solution of 3 g (6.55 mmol) of 5-[(1-tert-butoxyformamido)methyl]-3,6-dimethoxy-9,9-dimethylxanthene-4-acetic acid in 65 ml of methylene chloride was cooled to 20° and treated with 1.1 ml (10.62 mmol) of benzyl alcohol. After the addition of 20 mg of 4-dimethylaminopyridine a solution of 1.5 g (7.27 mmol) of dicyclohexylcarbodiimide in 16 ml of methylene chloride was added dropwise, whereupon the mixture was warmed to room temperature and was stirred for 3 hours. The precipitated dicyclohexylurea was filtered off and washed with a small amount of methylene chloride. The filtrate was washed with sodium bicarbonate solution and water, dried over sodium sulphate and concentrated. The residue remaining was chromatographed on silica gel with hexane/ethyl acetate, whereby 2.9 g of benzyl 5-[(1-tert-butoxyformamido)methyl]-3,6-dimethoxy-9,9-dimethylxanthene-4-acetate were obtained as a colourless powder m.p. of 139°–141°; IR 3443, 2972, 2930, 1724, 1605, 1498 $cm^{-1}$.

EXAMPLE 1.1.5

2.9 g (5.29 mmol) of benzyl 5-[(1-tert-butoxyformamido) methyl]-3,6-dimethoxy-9,9-dimethylxanthene-4-acetate were taken up in a mixture of 10 ml of trifluoroacetic acid and 5 ml of water at 0°. After half an hour the solvents were removed, whereupon the residue was treated with 20 ml of ether. The resulting solid was filtered off, washed with ether and dried over magnesium sulphate, whereby 2.25 g of benzyl 5-aminomethyl-3,6-dimethoxy-9,9-dimethylxanthene-4-acetate trifluoroacetate were obtained as a colourless powder of m.p. 169.5°–171°; IR 1716, 1662, 1631, 1604, 1538, 1494 cm$^{-1}$.

EXAMPLE 1.1.6

A solution of 2 g (3.56 mmol) of benzyl 5-aminomethyl-3,6-dimethoxy-9,9-dimethylxanthene-4-acetate trifluoroacetate in 70 ml of methanol was stirred at room temperature under hydrogen in the presence of 200 mg of palladium/charcoal (10%). After 30 minutes the catalyst was filtered off and the filtrate was concentrated. The residue was washed with ether and dried, whereby 1.6 g of 5-aminomethyl-3,6-dimethoxy-9,9-dimethylxanthene-4-acetic acid trifluoroacetate of m.p. 178°–184° (dec.) were obtained; IR 1680, 1630, 1608, 1496 cm$^{-1}$ absorbed.

EXAMPLE 1.1.7

1.58 g (34.35 mmol) of 5-aminomethyl-3,6-dimethoxy-9,9-dimethylxanthene-4-acetic acid trifluoroacetate were suspended in a mixture of 7 ml of dioxan and 7 ml of water together with 1.13 g (3.35 mmol) of N-(9-fluorenylmethoxycarbonyl)-succinimide, whereupon 0.9 ml (5.03 mmol) of ethyldiisopropylamine was added at 0°. The mixture was stirred at 0° for 2 hours and thereafter at room temperature for 4 hours. The solid obtained was filtered off, washed with water, dried and chromatographed on silica gel with chloroform/methanol. The fractions containing the desired product were combined, washed with dilute potassium hydrogen sulphate solution and thereafter with water, dried over magnesium sulphate and concentrated, whereby 1.17 g of 5-[(9-fluorenylmethoxyformamido)methyl]-3,6-dimethoxy-9,9-dimethylxanthene-4-acetic acid were obtained as a colourless powder of m.p. 134°–136°; IR 1727, 1703, 1606, 1495 cm$^{-1}$.

EXAMPLE 1.2.1

A solution of 0.3 g (0.534 mmol) of benzyl 5-aminomethyl-3,6-dimethoxy-9,9-dimethylxanthene-4-acetate trifluoroacetate in 60 ml of acetonitrile was treated firstly with 91 mg (1.09 mmol) of solid sodium bicarbonate and then with 0.43 g (0.64 mmol) of $N^\alpha,N^G,N^{G'}$-tris(benzyloxycarbonyl)-L-arginine N-hydroxysuccinimide ester. The mixture was stirred at room temperature for 21 hours and then poured into ice-water, whereupon it was extracted three times with methylene chloride. The combined extracts were washed with water, dried over magnesium sulphate and concentrated. The residue was prewashed twice with hexane/ethyl acetate and then chromatographed over silica gel in the same solvent mixture, whereby 0.45 g of benzyl 5-[(N$^2$-benzyloxycarbonyl-N$^5$-(benzyloxycarbonylamino-benzyloxycarbonylimino-methyl)-L-ornithyl-aminomethyl]-3,6-dimethoxy-9,9-dimethylxanthene-4-acetate was obtained as a colourless amorphous powder; IR 3388, 2958, 1720, 1676, 1607, 1495 cm$^{-1}$.

EXAMPLE 1.2.2

A solution of 0.38 g of benzyl 5-[(N$^2$-benzyloxycarbonyl-N$^5$-(benzyloxycarbonylamino-benzyloxycarbonylimino-methyl)-L-ornithyl-aminomethyl]-3,6-dimethoxy-9,9-dimethylxanthene-4-acetate in 48 ml of trifluoroethanol was treated with 77 mg of palladium/charcoal (10%) and stirred under hydrogen for 2 hours. Thereafter, the catalyst was filtered off and the filtrate was concentrated. The residue obtained was washed with ether and 0.2 g of 5-L-arginyl-aminomethyl-3,6-dimethoxy-9,9-dimethylxanthene-4-acetic acid was obtained; IR 3380-2830, 1656, 1604, 1557, 1492 cm$^{-1}$ absorbed.

EXAMPLE 1.2.3

A solution of 0.18 g (0.35 mmol) of 5-L-arginylaminomethyl-3,6-dimethoxy-9,9-dimethylxanthene-4-acetic acid in 72 ml of dimethylformamide was treated at 0° with 48 mg of dry sodium bicarbonate and then with 0.26 g (0.68 mmol) of O-benzotriazol-1-yl-N,N,N',N'-tetramethyluronium hexafluorophosphate. The reaction solution was stirred at 0° for 2.5 hours and thereafter evaporated to dryness. The residue was washed is with water and chromatographed on silica gel with chloroform/methanol/water, whereby (S)-8-(3-guanidinopropyl)-4,12-dimethoxy-17,17-dimethyl-1,1,5-methano-6,7,8,9,10,11-hexahydro-5H-dibenz[b,k][1,5,8]oxadiazacyclododecine-7,10-dione hexafluorophosphate was obtained; IR 3405, 2963, 1661, 1535, 1493 cm$^{-1}$.

EXAMPLE 1.2.4

A solution of 0.35 g of benzyl 5-aminomethyl-3,6-dimethoxy-9,9-dimethylxanthene-4-acetate trifluoroacetate in 70 ml of acetonitrite was cooled to 0° and treated with 0.15 g of N-benzyloxycarbonyl-L-alanine. A total of 0.36 9 of O-benzotriazol-1-yl-N,N,N',N'-tetramethyluronium hexafluorophosphate and 0.17 g of sodium bicarbonate were added in several portions. The reaction mixture was stirred for a total of 36 hours and thereby warmed to room temperature, whereupon it was diluted with ice-water and extracted with methylene chloride. The organic phase was washed with water, dried over magnesium sulphate and concentrated. The residue was chromatographed several times over silica gel in chloroform/methanol, whereby 0.33 g of benzyl 5-[(N-benzyloxycarbonyl-L-alanyl)aminomethyl]-3,6-dimethoxy-9,9-dimethylxanthene-4-acetate was obtained as a colourless foam; IR 1728, 1673, 1605, 1494 cm$^{-1}$.

EXAMPLE 1.2.5

A solution of 0.3 g of benzyl 5-[(N-benzyloxycarbonyl-L-alanyl)aminomethyl]-3,6-dimethoxy-9,9-dimethylxanthene-4-acetate in 85 ml of trifluoroethanol was stirred under hydrogen for 15 minutes in the presence of palladium/charcoal (10%). The catalyst was filtered off and rinsed with trifluoroethanol. The filtrate and wash solution were brought to dryness and the combined residue was chromatographed over silica gel in chloroform/methanol/water, whereby 0.1.8 g 5-(L-alanylaminomethyl)-3,6-dimethoxy-9,9-dimethylxanthene-4-acetic acid was obtained as a colourless foam; IR 3450–2400, 1679, 1606, 1575, 1493 cm$^{-1}$.

EXAMPLE 1.2.6

A solution of 0.15 g of 5-(L-alanyl-aminomethyl)-3,6-dimethoxy-9,9-dimethylxanthene-4-acetic acid in 84 ml of dimethylformamide was cooled to 0° and treated at this temperature with 49 mg of sodium bicarbonate and with 0.26 g of O-benzotriazol-1-yl-N,N,N',N'- tetramethyluronium hexafluorophosphate. The mixture was stirred at 0° for 5 hours and subsequently concentrated. The residue was taken up in ether/chloroform, whereupon the solution obtained was washed with water. After removing the solvent the crude product was chromatographed over silica gel in chloroform/methanol, whereby 87 mg of (S)-4,12-dimethoxy-8,17,17-trimethyl-1,15-methano-6,7,8,9,10,11-hexahydro-5H-dibenz[b,k][1,5,8]oxadiazacyclododecine-7,10-dione were obtained; IR 3398, 3294, 2966, 1660, 1603, 1530, 1491, 1463, 1419 cm$^{-1}$.

EXAMPLE 1.2.7

A solution of 0.9 g (1.55 mmol) of calcium (N$^2$-Benzyloxycarbonyl-N$^6$-tert-butoxycarbonyl-L-lysyl)-L-glutamate in 50 ml of dimethylformamide was cooled to 0°, whereupon firstly 0.9 g (1.6 mmol) of benzyl 5-aminomethyl-3,6-dimethoxy-9,9-dimethylxanthene-4-acetate trifluoroacetate, then 0.91 g (2.4 mmol) of O-benzotriazol-1-yl-N,N,N',N'-tetramethyluronium hexafluorophosphate and then 0.48 g (4.8 mmol) of N-methylmorpholine were added. The mixture was warmed to room temperature within 15 hours and then concentrated. The residue was taken up in chloroform, whereupon the solution was washed with 3×50 ml of water and dried over magnesium sulphate. The solution obtained was filtered over silica gel in chloroform, whereby 0.99 g of benzyl 5-[(N$^2$-benzyloxycarbonyl-N$^6$-tert-butoxycarbonyl-L-lysyl-5-O-tert-butyl-L-glutamyl)aminomethyl]-3,6-dimethoxy-9,9-dimethylxanthene-4-acetate of m.p. 132°–135° was obtained; IR 1707, 1668, 1605, 1525, 1496 cm$^{-1}$.

EXAMPLE 1.2.8

A solution of 0.5 g (0.5 mmol) of benzyl 5-[(N$^2$-benzyloxycarbonyl-N$^6$-tert-butoxycarbonyl-L-lysyl-5-O-tert-butyl-L-glutamyl)aminomethyl]-3,6-dimethoxy-9,9-dimethylxanthene-4-acetate was dissolved in 40 ml of methanol, whereupon 100 mg of palladium/charcoal (10%) were added and the mixture was stirred under hydrogen for 4.5 hours. After filtering of the catalyst and concentrating the filtrate 0.39 g of 5-[(N$^6$-tert-butoxycarbonyl-L-lysyl-5-O-tert-butyl-L-glutamyl)aminomethyl]-3,6-dimethoxy-9,9-dimethylxanthene-4-acetic acid remained behind as a colourless powder of m.p. 122°–125°; IR 3395, 2973, 2935, 2600, 1713, 1682, 1606, 1521, 1494 cm$^{-1}$.

EXAMPLE 1.2.9

A solution of 0.365 g of 5-[(N$^6$-tert-butoxycarbonyl-L-lysyl-5-O-tert-butyl-L-glutamyl)aminomethyl]-3,6-dimethoxy-9,9-dimethylxanthene-4-acetic acid in 500 ml of dimethylformamide was cooled to 0°, whereupon firstly 0.54 g of O-benzotriazol-1-yl-N,N,N',N'-tetramethyluronium hexafluorophosphate and then 0.2 g of sodium bicarbonate were added. After 15 hours the mixture was warmed to room temperature and concentrated. The residual oil was taken up in chloroform and the solution obtained was washed three times with water, dried over magnesium sulphate and concentrated. The residue obtained was chromatographed several times over silica gel in chloroform/methanol, whereby tert-butyl 3-[(8S,11S)-11-(4-tert-butoxycarbonylaminobutyl)-4,15-dimethoxy-20,20-dimethyl-7,10,13-trioxo-1,18-methano-5,6,7,8,9,10,11,12,13,14-decahydrodibenz[b,n][1,5,8,11]oxatriazacyclopentadecin-8-yl]propionate was obtained as an amorphous powder; IR 3309, 2924, 2933, 1683, 1606, 1522, 1491 cm$^{-1}$.

EXAMPLE 1.2.10

50 mg of tert-butyl 3-[(8S,11S)-11-(4-tert-butoxycarbonylaminobutyl)-4,15-dimethoxy-20,20-dimethyl-7,10,13-trioxo-1,18-methano-5,6,7,8,9,10,11,12,13,14-decahydrodibenz[b,n][1,5,8,11]loxatriazacyclopentadecin-8-yl]propionate were dissolved in a mixture of trifluoroacetic acid and methylene chloride (1/1). The solution was stirred at room temperature for 90 minutes and then concentrated. The residue was purified on silica gel in chloroform/methanol/water, whereby 22 mg of 3-[(8S,11 S)-11-(4-aminobutyl-4,15-dimethoxy-20,20-dimethyl-7,10,13-trioxa-1,18-methano-5,6,7,8,9,10,11,12,13,14-decahydrodibenz[b,n][1,5,8,11]oxatriazacyclopentadecin-8-yl]propionic acid were obtained; IR 3419, 3304, 2961, 1671, 1605, 1531, 1493 cm$^{-1}$.

EXAMPLE 1.2.11

A solution of 0.55 g (1.5 mmol) of N-[(2S,3R)-2-benzyloxycarbonyl-3-tert-butoxy-butyryl]-glycine in 75 ml of dimethylformamide was cooled to 0°–5° and treated firstly with 0.84 9 (1.5 mmol) of benzyl 5-aminomethyl-3,6-dimethoxy-9,9-dimethylxanthene-4-acetate trifluoroacetate, then with 0.85 g (2.25 mmol) of O-benzotriazol-1-yl-N,N,N',N'-tetramethyluronium hexafluorophosphate and finally with 0.5 ml of N-methylmorpholine. The mixture obtained was brought to room temperature while stirring in the course of 15 hours and thereafter freed from solvent. The residue was taken up in 100 ml of ethyl acetate, whereupon the solution was washed with 2×50 ml of water, dried over sodium sulphate and evaporated. The foam remaining as the residue was chromatographed on silica gel in chloroform/methanol, whereby 0.94 g of benzyl 5-[(N-benzyloxycarbonyl-O-tert-butyl-L-threonylglycyl)aminomethyl]-3,6-dimethoxy-9,9-dimethylxanthene-4-acetate was obtained; IR 3401, 2972, 1726, 1667, 1605, 1493 cm$^{-1}$.

EXAMPLE 1.2.12

A solution of 0.67 g (0.84 mmol) of benzyl 5-[(N-benzyloxycarbonyl-O-tert-butyl-L-threonyl-glycyl)aminomethyl]-3,6-dimethoxy-9,9-dimethylxanthene-4-acetate in 100 ml of methanol was treated with 140 mg of palladium/charcoal (10%) and stirred under hydrogen for 1 hour. Thereafter, the catalyst was filtered off and the filtrate was brought to dryness. 0.46 g of 5-[O-tert-butyl-L-threonyl-glycyl)aminomethyl1-3,6-dimethoxy-9,9-dimethylxanthene-4-acetic acid was obtained as the residue in the form of a colourless amorphous powder; IR 3400–2500, 1675, 1606, 1578, 1531, 1493 cm$^{-1}$.

EXAMPLE 1.2.13

A solution of 50 mg of 5-[O-tert-butyl-L-threonyl-glycyl)aminomethyl]-3,6-dimethoxy-9,9-dimethylxanthene-4-acetic acid in 105 ml of dimethylformamide was cooled to 0°, whereupon firstly 99 mg of O-benzotriazol-1-yl-N,N,N', N'-tetramethyluronium hexafluorophosphate and then 37 mg of sodium bicarbonate were added. The solution obtained was warmed to room temperature overnight and then evaporated. The residue was taken up in ethyl acetate/water. The organic phase was separated, back-washed with water, dried over magnesium sulphate and freed from solvent. The residue remaining was filtered over silica gel in chloroform/methanol, whereby 49 mg of (11S)-[(R)-11 -(1-tert-butoxyethyl)]-4,15-dimethoxy-20,20-dimethyl-1,18-methano-5,6,7,8,9,10,11,12,13,14-decahydro-dibenz[b,n][1,5,8,11]oxatriazacyclopentadecine-7,10,13-trione were obtained as a pale yellow, amorphous powder; IR 3426, 3306, 2972, 1684, 1653, 1605, 1527, 1492 cm$^{-1}$.

EXAMPLE 1.2.14

A solution of 0.27 g (0.48 mmol) of (11S)-[(R)-11-(1-tert-butoxyethyl)]-4,15-dimethoxy-20,20-dimethyl-1,18-methano-5,6,7,8,9,10,11,12,13,14-decahydro-dibenz[b,n][1,5,8,1 1]oxatriazacyclopentadecine-7,10,13-trione in 4 ml of methylene chloride was cooled to 0° and treated slowly with 4 ml of trifluoroacetic acid. The solution obtained was warmed to room temperature, stirred for 5 hours and evaporated to dryness. The residue was chromatographed over silica gel in chloroform/methanol, whereby 0.22 g of (11S)-[(R)-11-(1-hydroxyethyl)]-4,15-dimethoxy-20,20-dimethyl-1,18-methano-5,6,7,8,9,10,11, 12,13,14-decahydro-dibenz (b,n][1,5,8,11]-oxatriazacyclopentadecine-7,10,13-trione was obtained as a light yellowish foam; IR 3432, 3274, 2968, 2934, 1678, 1645, 1605, 1533, 1493 cm$^{-1}$. A sample of this material was recrystallized from ethanol/water and then showed a m.p. of 194°–196° (dec.).

EXAMPLE 1.2.15

A solution of 0.52 g (0.8 mmol) of N-(9H-fluoren-9-ylmethoxycarbonyl)-L-isoleucyl-O-tert-butyl-L-tyrosyl-L-alanine in 20 ml of dimethylformamide was cooled to 0° and treated with 0.45 g (0.8 mmol) of benzyl 5-aminomethyl-3,6-dimethoxy-9,9-dimethylxanthene-4-acetate trifluoroacetate and with 0.45 g (1.2 mmol) of O-benzotriazol-1-yl-N,N,N',N'-tetra-methyluronium hexafluorophosphate. Thereafter, 0.31 g (2.4 mmol) of ethyldiisopropylamine was added, whereupon the reaction mixture obtained was warmed from 0° to room temperature within 3 hours and concentrated. The residue remaining was taken up in chloroform, whereupon the solution obtained was washed with water and dried over magnesium sulphate. After chromatography over silica gel (chloroform) 0.77 g of benzyl 3,6-dimethoxy-9,9-dimethyl-5-[(N-(9H-fluoren-9-ylmethoxycarbonyl)-L-isoleucyl-O-tert-butyl-L-tyrosyl-L-alanyl)aminomethyl]xanthene-4-acetate of m.p. 218°–220° was obtained; IR 1728, 1662, 1606, 1503, 1492 cm$^{-1}$.

EXAMPLE 1.2.16

A solution of 0.74 g (0.73 mmol) of benzyl 3,6-dimethoxy-9,9-dimethyl-5-[(N-(9H-fluoren-9-ylmethoxycarbonyl)-L-isoleucyl-O-tert-butyl-L-tyrosyl-L-alanyl)aminomethyl]xanthene-4-acetate in 7 ml of dimethylformamide was stirred at 0° for 1 hour in the presence of 0.7 ml of diethylamine. The reaction mixture was brought to dryness. The residue obtained was chromatographed over silica gel in chloroform/methanol, whereby 0.53 g of benzyl 3,6-dimethoxy-9,9-dimethyl-5-[(L-isoleucyl-O-tert-butyl-L-tyrosyl-L-alanyl)aminomethyl] xanthene-4-acetate was obtained; IR 3292, 2970, 1742, 1672, 1655, 1627, 1605, 1536, 1502, 1499 cm$^{-1}$.

EXAMPLE 1.2.17

A solution of 0.27 g of benzyl 3,6-dimethoxy-9,9-dimethyl-5-[(L-isoleucyl-O-tert-butyl-L-tyrosyl-L-alanyl) aminomethyl]xanthene-4-acetate in 15 ml of methanol was treated with 50 mg of palladium/charcoal (10%) and stirred under hydrogen for 3 hours. After filtering off the catalyst the solvent was removed and the residue was washed with ether. 0.24 g of 3,6-dimethoxy-9,9-dimethyl-5-[(L-isoleucyl-O-tert-butyl-L-tyrosyl-L-alanyl)aminomethyl] xanthene-4-acetic acid of m.p. 146°–149° was obtained; IR 1662, 1606, 1506, 1494 cm$^{-1}$.

EXAMPLE 1.2.18

A solution of 0.24 g (0.32 mmol) of 3,6-dimethoxy-9,9-dimethyl-5-[(L-isoleucyl-O-tert-butyl-L-tyrosyl-L-alanyl) aminomethyl]xanthene-4-acetic acid in 480 ml of dimethylformamide was cooled to 0° and treated firstly with 0.36 g (0.96 mmol) of O-benzotriazol-1-yl-N,N,N',N'-tetramethyluronium hexafluorophosphate and then with 0.16 g (1.90 mmol) of sodium bicarbonate. The reaction mixture was stirred at 0° for 3 hours, warmed to room temperature and concentrated. The residue was taken up in chloroform and the solution obtained was washed with water, dried over magnesium sulphate and concentrated. After chromatography over silica gel (in chloroform/methanol) 0.16 g of 4,5-cyclo-[acetyl-L-isoleucyl-O-tert-butyl-L-tyrosyl-L-alanyl-aminomethyl]-3,6-dimethoxy-9,9-dimethylxanthene was obtained as a colourless powder; IR 3406, 3328, 2971, 1664, 1605, 1506 cm$^{-1}$.

EXAMPLE 1.2.19

A solution of 0.1 g (0.134 mmol) of 4,5-cyclo-[acetyl-L-isoleucyl-O-tert-butyl-L-tyrosyl-L-alanyl-aminomethyl]-3, 6-dimethoxy-9,9-dimethylxanthene in 4 ml of methylene chloride is was cooled to 0°, treated with 0.5 ml of trifluoroacetic acid and thereafter stirred at 0° for 5 hours. After warming to room temperature the mixture was concentrated. The residue remaining was washed with ether, whereby 91 mg of 4,5-cyclo[acetyl-L-isoleucyl-L-tyrosyl-L-alanyl-aminomethyl]-3,6-dimethoxy-9,9-dimethylxanthene of m.p. 193°–196° (dec.) were obtained; IR 3331, 2965, 1662, 1608, 1515, 1498 cm$^{-1}$.

EXAMPLE 1.2.20

A solution of 45 mg of N-benzyloxycarbonyl-L-valyl-L-alanyl-L-alanyl-L-phenylalanyl-L-leucyl-L-alanyl-L-leucyl-L-alanine -alanine in 5 ml of dimethylformamide was treated with 27 mg of benzyl 5-aminomethyl-3,6-dimethoxy-9,9-dimethylxanthene-4-acetate trifluoroacetate and 28 mg of O-benzotriazol-1-yl-N,N,N',N'-tetramethyluronium hexafluorophosphate and thereafter cooled to 0°. After adding 16 mg of ethyldiisopropylamine the mixture was stirred for 15 hours while warming to room temperature. The residue remaining after removal of the solvent was washed in succession with water and methanol and chromatographed on silica gel in chloroform/methanol, whereby benzyl 5-[(N-benzyloxycarbonyl-L-valyl-L-alanyl-L-alanyl-L-phenyl-alanyl-L-leucyl-L-alanyl-L-leucyl-L-alanyl)aminomethyl]-3,6-dimethoxy-9,9-dimethylxanthene-4-acetate(benzyl 5-[(N-benzyloxycarbonyl-SEQ ID NO:9)aminomethyl]-3,6-dimethoxy-9,9-dimethylxanthene-4-acetate) of m.p. 287°–290° was obtained; IR 3284, 2959, 1632, 1532, 1500 cm$^{-1}$.

EXAMPLE 1.2.21

100 mg of benzyl 5-[(N-benzyloxycarbonyl-L-valyl-L-alanyl-L-alanyl-L-phenylalanyl-L-leucyl-L-alanyl-L-leucyl-L-alanyl)aminomethyl]-3,6-dimethoxy-9,9-dimethylxanthene-4-acetate (benzyl 5-[(N-benzyloxycarbonyl-SEQ ID NO:9)aminomethyl]-3,6-dimethoxy-9,9-dimethylxanthene-4-acetate) were dissolved in 200 ml of hexafluoroisopropanol, treated with 60 mg of palladium on calcium carbonate (10%) and stirred under hydrogen for 3 hours. After filtering the catalyst the filtrate was concentrated. The residue remaining was washed several times with methanol and thereafter chromatographed over silica gel in chloroform/methanol/hexafluoroisopropanol, whereby 65 mg of 3,6-dimethoxy-9,9-dimethyl-5-[(L-valyl-L-alanyl-L-alanyl-L-phenylalanyl-L-leucyl-L-alanyl-L-leucyl-L-alanyl)

aminomethyl]xanthene-4-acetic acid (3,6-dimethoxy-9,9-dimethyl-5-[(SEQ ID NO:9)aminomethyl]xanthene-4-acetic acid) were obtained; IR 3393, 3288, 2963, 1685, 1636, 1531 cm$^{-1}$.

EXAMPLE 1.2.22

A solution of 104 mg of 3,6-dimethoxy-9,9-dimethyl-5-[(L-valyl-L-alanyl-L-alanyl-L-phenylalanyl-L-leucyl-L-alanyl-L-leucyl-L-alanyl)aminomethyl]xanthene-4-acetic acid (3,6-dimethoxy-9,9-dimethyl-5-[(SEQ ID NO:9) aminomethyl]xanthene-4-acetic acid) in 140 ml of dimethylformamide was cooled to 0° and treated with 106 mg of O-benzotriazol-1-yl-N,N,N',N'-tetramethyluronium hexafluorophosphate and with 40 mg of sodium bicarbonate. The mixture was stirred for 25 hours while warming to room temperature. After removing the solvent the residue was chromatographed several times over silica gel in chloroform/methanol. After crystallization from chloroform/methanol there remained 17 mg of colourless 4,5-cyclo-[acetyl-L-valyl-L-alanyl-L-alanyl-L-phenylalanyl-L-leucyl-L-alanyl-L-leucyl-L-alanyl-aminomethyl]-3,6-dimethoxy-9,9-dimethylxanthene(4,5-cyclo-[acetyl-SEQ ID NO:9-aminomethyl]-3,6-dimethoxy-9,9-dimethylxanthene) of m.p. 277°–280°; IR 3322, 2958, 1650, 1523 cm$^{-1}$.

EXAMPLE 1.2.23

A solution of 0.17 g of benzyl 5-aminomethyl-3,6-dimethoxy-9,9-dimethylxanthene-4-acetate trifluoroacetate and 0.14 g of N-(9-fluorenylmethoxycarbonyl)-4-O-tert-butyl-D-aspartic acid in 5 ml of dimethylformamide was treated with 0.11 g of O-benzotriazol-1-yl-N,N,N',N'-tetramethyluronium tetrafluoroborate and with 0.11 ml of diisopropylethylamine. The mixture was stirred at room temperature for 1 hour and thereafter poured into dilute sodium bicarbonate solution. The resulting precipitate was filtered off, washed with water KHSO$_4$/K$_2$SO$_4$ solution and again with water and dried with 400 in a vacuum, whereby 0.25 g of benzyl 5-[(N-(9-fluorenylmethoxycarbonyl)-4-O-tert-butyl-D-aspartyl)aminomethyl]-3,6-dimethoxy-9,9-dimethylxanthene-4-acetate was obtained; MS: 841.5 (M+H)$^+$.

EXAMPLE 1.2.24

A solution of 0.21 g of benzyl 5-[(N-(9-fluorenylmethoxycarbonyl)-4-O-tert-butyl-D-aspartyl) aminomethyl]-3,6-dimethoxy-9,9-dimethylxanthene-4-acetate in 8 ml of dimethylformamide was treated with 2 ml of piperidine, left to stand at room temperature for 30 minutes and subsequently concentrated in a vacuum. The residue remaining was treated in succession with 0.11 g of N-(9-fluorenylmethoxycarbonyl-D-tryptophan, 0.08 g of O-benzotriazol-1-yl-N,N,N',N'-tetramethyluronium tetrafluoroborate and 0.056 ml of diisopropylethylamine. The mixture was stirred at room temperature for 2 hours and thereafter treated with dilute sodium bicarbonate solution, whereby a precipitate separated. The precipitate was filtered off and dissolved in ethyl acetate. The solution was washed in succession with saturated sodium bicarbonate solution, KHSO$_4$/K$_2$SO$_4$ solution and saturated sodium chloride solution, dried over sodium sulphate and concentrated. The residue was precipitated from ethanol/water and dried at 400 in a vacuum, whereby 0.22 g of benzyl 5-[(N-(9-fluorenylmethoxycarbonyl)-D-tryptophanyl-4-O-tert-butyl-D-aspartyl)aminomethyl]-3,6-dimethoxy-9,9-dimethylxanthene-4-acetate was obtained; MS: 1027.2 (M+H)$^+$.

EXAMPLE 1.2.25

A solution of 0.19 9 of benzyl 5-[(N-(9-fluorenylmethoxycarbonyl)-D-tryptophanyl-4-O-tert-butyl-D-aspartyl)aminomethyl]-3,6-dimethoxy-9,9-dimethylxanthene-4-acetate in 8 ml of dimethylformamide was treated with 2 ml of piperidine, whereupon the mixture was left to stand at room temperature for 30 minutes and then concentrated. The residue was washed with hexane with the addition of a small amount of ether and dissolved in 3 ml of dimethylformamide. The solution was treated with 0.09 g of N-(benzyloxycarbonyl)-L-leucine N-hydroxysuccinimide ester and stirred at room temperature for 3 hours, whereupon dilute sodium bicarbonate solution was added. The precipitate was filtered off, washed with water, KHSO$_4$K$_2$SO$_4$ solution and again with water and dissolved in 10 ml of methanol. The solution obtained was stirred under hydrogen for 4 hours in the presence of 16 mg of palladium/charcoal (10%). The catalyst was filtered off and the filtrate was freed from solvent. The residue was taken up in 10 ml of dimethylformamide and treated with 0.06 ml of diisopropylethylamine. The solution obtained was added within 30 minutes while stirring to a solution of 0.13 g of O-benzotriazol-1-yl-N,N,N',N'-tetramethyluronium tetrafluoroborate in 50 ml of dimethylformamide. The mixture was stirred at room temperature for a further 2 hours and thereafter added dropwise to dilute sodium bicarbonate solution. The separated precipitate was filtered off, washed with KHSO$_4$/K$_2$SO$_4$ solution, dried in a vacuum and taken up in a mixture of 9.5 ml of trifluoroacetic acid and 0.5 ml of water. The solution was left to stand at room temperature for 1 hour and then freed from solvent. The residue was purified by HPLC (C-18 phase, gradient water/ethanol with 1% trifluoroacetic acid), whereby 34 mg of 4,5-cyclo-[acetyl-L-leucyl-D-tryptophanyl-D-aspartyl-aminomethyl]-3,6-dimethoxy-9,9-dimethylxanthene were obtained; IR 3407, 2958, 1660, 1524 and 1493 cm$^{-1}$; MS: 754.2 (M+H)$^+$.

EXAMPLE 1.2.26

A solution of 0.25 g of benzyl 5-aminomethyl-3,6-dimethoxy-9,9-dimethylxanthene-4-acetate trifluoroacetate in 3 ml of dimethylformamide was treated in succession with 0.36 g of N$^\alpha$-benzyloxycarbonyl-N$^G$-(2,2,5,7,8-pentamethylchroman-6-sulphonyl)-L-arginyl-glycyl-4-O-tert-butyl-L-aspartyl-L-valine, 0.17 g of O-benzotriazol-1-yl-N,N,N',N'-tetramethyluronium hexafluorophosphate and 0.17 ml of diisopropylethylamine. After stirring for 30 minutes the reaction mixture was poured into dilute sodium bicarbonate solution. The precipitate obtained was filtered off, washed with water and dried in a vacuum, whereby 0.5 g of benzyl 5-[(N$^\alpha$-benzyloxycarbonyl-N$^G$-(2,2,5,7,8-pentamethylchroman-6-sulphonyl)-L-arginyl-glycyl-4-O-tert-butyl-L-aspartyl-Lvalyl)aminomethyl]-3,6-dimethoxy-9,9-dimethylxanthene-4-acetate was obtained; MS: 1331.6 (M+H)$^+$.

EXAMPLE 1.2.27

A solution of 0.47g of benzyl 5-[(N$^\alpha$-benzylbxycarbonyl-N$^G$-(2,2,5,7,8-pentamethylchroman-6-sulphonyl)-L-arginyl-glycyl-4-O-tert-butyl-L-aspartyl-L-valyl) aminomethyl]-3,6-dimethoxy-9,9-dimethylxanthene-4-acetate in 25 ml of trifluoroethanol was stirred under hydrogen for 2 hours in the presence of palladium/charcoal (10%). Thereafter, the catalyst was filtered off and the filtrate was brought to dryness, The residue was taken up in 20 ml of dimethylformamide together with 0.34 ml of diisopropylethylamine. The solution obtained was added dropwise within 20 minutes to a solution of 0.66 g of O-benzotriazol-1-yl-N,N,N',N'-tetramethyluronium hexafluorophosphate in 50 ml of dimethylformamide, whereupon the mixture was stirred at room temperature for 1 hour. Subsequently, the majority of the solvent was removed in a vacuum, whereupon the concentrate obtained was poured into dilute sodium bicarbonate solution. The resulting precipitate was filtered off, washed with water and dried. This crude product was dissolved in a mixture of 20 ml of trifluoroacetic acid, 0.5 ml of water and 0.2 ml of phenol. The solution was left to stand at room temperature for 1 hour and then concentrated. The residue remaining was digested with ether and lyophilized from glacial acetic acid. After purification by HPLC (C-18 phase; gradient: water/ethanol with 0.1% trifluoroacetic acid) 75 mg of 4,5-cyclo-[acetyl-L-arginyl-glycyl-L-aspartyl-L-valyl-aminomethyl]-3,6-dimethoxy-9,9-dimethylxanthene trifluoroacetate(4,5-cyclo-[acetyl-SEQ ID NO:2-aminomethyl]-3,6-dimethoxy-9,9-dimethylxanthene trifluoroacetate) were obtained; IR 3364, 2965, 2841, 1664, 1577 and 1497 cm$^{-1}$; MS: 767 (M+H)$^+$.

EXAMPLE 1.3.1

A solution of 0.13 g (0.24 mmol) of N-benzyloxycarbonyl-L-alanyl-O-tert-butyl-L-threonyl-L-valyl-glycine and 0.11 g (0.3 mmol) of O-benzotriazol-1-yl-N,N,N',N'-tetramethyluronium hexafluorophosphate in 8 ml of dimethylformamide was treated with 0.08 g (0.2 mmol) of methyl 5-aminomethyl-3,6-dimethoxy-9,9-dimethylxanthene-4-acetate hydrochloride. The mixture was cooled to 0°, treated with 0.07g (0.54mmol) of ethyidiisopropylamine and stirred at 0° for 19 hours. After warming to room temperature water was added, whereupon the precipitate formed was filtered off, washed with water and purified over silica gel in chloroform/methanol. The product obtained was precipitated with ether, whereby 0.16 g of methyl 5-[(N-benzyloxycarbonyl-L-alanyl-O-tert-butyl-L-threonyl-L-valyl-glycyl)aminomethyl]-3,6-dimethoxy-9,9-dimethylxanthene-4-acetate of m.p. 181°–184° was obtained; IR 3277, 2968, 1738, 35 1671, 1632, 1600, 1524, 1495 cm$^{-1}$.

EXAMPLE 1.3.2

A solution of 70 mg of methyl 5-[(N-benzyloxycarbonyl-L-alanyl-O-tert-butyl-L-threonyl-L-valyl-glycyl) aminomethyl]-3,6-dimethoxy-9,9-dimethylxanthene-4-acetate in 20 ml of dioxan was treated with 47 mg of palladium/charcoal (10%) and stirred under hydrogen for 19 hours. After filtering off the catalyst the filtrate was concentrated, whereby 59 mg of colourless methyl 5-[(L-alanyl-O-tert-butyl-L-threonyl-L-valyl -glycyl) aminomethyl]-3,6-dimethoxy-9,9-dimethylxanthene-4-acetate was obtained; IR 3300, 2970, 1741,. 1680, 1658, 1631, 1523, 1494 cm$^{-1}$.

EXAMPLE 1.3.3

A solution of 30 mg of methyl 5-[(L-alanyl-O-tert-butyl-L-threonyl-L-valyl-glycyl)aminomethyl]-3,6-dimethoxy-9,9-dimethylxanthene-4-acetate in 0.6 ml of pyridine, was cooled to 0° and treated in several portions with a total of 0.17 ml of 2N sodium hydroxide solution. The reaction mixture obtained was stirred for 24 hours and thereafter brought to dryness, and the residue was taken up in water. The solution obtained was acidified with 1N hydrochloric acid, washed with ethyl acetate and brought to dryness. The colourless residue was taken up in 20 ml of dimethylformamide and the solution obtained was cooled to 0°, treated at this temperature with 37 mg of sodium bicarbonate and 69 mg of diphenylphosphoryl azide and stirred for 14 hours while slowly warming to room temperature The residue remaining after removing the solvent was washed with pentane and thereafter partitioned between water and ethyl acetate. The combined organic phases were dried over magnesium sulphate anoverncentrated. The residue was chromatographed over silica gel in chloroform/methanol, whereby 7 mg of 4,5-cyclo-[acetyl-L-alanyl-O-tert-butyl-L-threonyl-L-valyl-glycylaminomethyl]-3,6-dimethoxy-9,9-dimethylxanthene were obtained; IR 3415, 3345, 2971, 2931, 1672, 1605, 1515 cm$^{-1}$.

EXAMPLE 1.3.4

A solution of 4 mg of 4,5-cyclo-[acetyl-L-alanyl-O-tert-butyl-L-threonyl-L-valyl-glycyl-aminomethyl]-3,6-dimethoxy-9,9-dimethylxanthene in 0.4 ml of trifluoroacetic acid was treated with two drops of water and stirred at room temperature for 2 hours. The reaction mixture was brought to dryness and the residue obtained was chromatographed over silica gel and subsequently recrystallized from acetonitrile. 3 mg of 4,5-cyclo-[acetyl-L-alanyl-L-threonyl-L-valy-glycyl-aminomethyl]-3,6-dimethoxy-9,9-dimethylxanthene(4,5-cyclo-[acetyl-SEQ ID NO:1-aminomethyl]-3,6-dimethoxy-9,9-dimethylxanthene) of m.p. 239°–242° were obtained; IR 3395, 2965, 2933, 1672, 1608, 1531, 1494 cm$^{-1}$.

EXAMPLE 1.4.1

A solution of 0.46 g of 5-[(1-tert-butoxyformamido) methyl]-3,6-dimethoxy-9,9-dimethylxanthene-4-acetic acid and 0.3 g of O-benzyl-L-glutamine hydrochloride in 10 ml of dimethylformamide was cooled to 0° and treated firstly with 0.45 g of O-benzotriazol-1-yl-N,N,N',N'-tetramethyluronium hexafluorophosphate and then with 0.37 ml of diisopropylethylamine. The solution obtained was warmed to room temperature, stirred for 2 hours and then poured into dilute sodium bicarbonate solution. The separated precipitate was filtered off, washed with water and dried in a vacuum, whereby 0.59 g of 5-[N-(tert-butyloxycarbonyl)aminomethyl]-3,6-dimethoxy-9,9-dimethoxyxanthene-4-acetic acid (O-benzyl-L-glutamyl) amide was obtained; MS: 676 (M+H)$^+$.

EXAMPLE 1.4.2

A solution of 0.54 g of 5-[N-(tert-butyloxycarbonyl) aminomethyl]-3,6-dimethoxy-9,9-dimethoxyxanthene-4-acetic acid (O-benzyl-L-glutamyl)amide in 10 ml of trifluoroacetic acid and 0.5 ml of water was left to stand at room temperature for 10 minutes and the concentrated. The residue was brought to dryness twice with toluene and then taken up in 10 ml of dimethylformamide. The solution obtained was treated in succession with 0.46 g of N-(9-fluorenylmethoxycarbonyl)-O-tert-butyl-L-tyrosine, 0.42 g of O-benzotriazol-1-yl-N,N,N',N'-tetra-methyluronium hexafluorophosphate and 0.35 ml of diisopropylethyluronium. The mixture was stirred at room temperature for 1.5 hours and thereafter poured into dilute sodium bicarbonate solution. The separated precipitate was filtered off, dried and re-precipitated from hexane/ethyl acetate, whereby 0.47 g of 5-[(N-(9-fluorenylmethoxycarbonyl)-O-tert-butyl-L-tyrosyl)amino-methyl]-3,6-dimethoxy-9,9-dimethylxanthene-4-acetic acid (O-benzyl-L-glutamyl) amide was obtained; MS: 1017.3 (M+H)$^+$.

EXAMPLE 1.4.3

A solution of 0.39 g of 5-[(N-(9-fluorenylmethoxycarbonyl)-O-tert-butyl-L-tyrosyl)

aminomethyl]-3,6-dimethoxy-9,9-dimethylxanthene-4-acetic acid (O-benzyl-L-glutamyl)amide in 6 ml of dimethylformamide and 4 ml of piperidine was left to stand at room temperature for 15 minutes and then brought to dryness. The residue remaining was digested with hexane and subsequently dissolved in 5 ml of dimethylformamide. The solution obtained was cooled to 0° and treated in succession with 0.36 g of $N^\alpha,N^G,N^G$-tris (benzyloxycarbonyl)-L-arginyl-glycyl-4-O-tert-butyl-L-aspartyl-L-valine 0.06 g of N-hydroxybenzotriazole hydrate, 0.13 g of O-(1,2-dihydro-2-oxo-1-pyridyl)-N,N,N',N'-tetramethyluronium tetrafluoroborate and 0.15 ml of diisopropylethylamine. The reaction mixture was stirred at room temperature for 30 minutes and then poured into dilute sodium bicarbonate solution. The separated precipitated was filtered off, washed with water and $KHSO_4/K_2SO_4$ solution and reprecipitated from hexane/ethyl acetate, whereby 0.53 g of 5-[($N^\alpha,N^G,N^G$-tris(benzyloxycarbonyl)-L-arginyl-glycyl-4-O -tert-butyl-L-aspartyl-L-valyl-O-tert-butyl-L-tyrosyl)aminomethyl]-3,6-dimethoxy-9,9-dimethylxanthene-4-acetic acid (O-benzyl-L-glutamyl) amide was obtained; MS: 1681.7 $(M+H)^+$.

EXAMPLE 1.4.4

A solution of 0.47 g of 5-[($N^\alpha,N^G,N^G$-tris (benzyloxycarbonyl)-L-arginyl-glycyl-4-O-tert-butyl-L-aspartyl-L-valyl-O-tert-butyl-L-tyrosyl)aminomethyl]-3,6-dimethoxy-9,9-dimethylxanthene-4-acetic acid (O-benzyl-L-glutamyl)amide in 20 ml of trifluoroethanol was hydrogenated at room temperature and normal pressure with the addition of palladium/charcoal (10%). Thereafter, the catalyst was filtered off and the filtrate was concentrated. The residue was taken up in 20 ml of dimethylformamide and the solution obtained was treated with 0.04 g of N-hydroxybenzotriazole hydrate. The solution was added dropwise within 20 minutes to a solution of 0.24 g of O-(1,2-dihydro-2-oxo-1-pyridyl)-N,N,N',N'-tetramethyluronium tetrafluoroborate and 0.14 ml of diisopropylethylamine in 80 ml of dimethylformamide. The reaction mixture was stirred at room temperature for 1 hour and thereafter concentrated. The residue was partitioned between n-butanol/ethyl acetate and saturated sodium bicarbonate solution. The organic phase was separated, backwashed with saturated sodium chloride solution and freed from solvent. The residue remaining was dissolved in 25 ml of trifluoroacetic acid and the solution was left to stand at room temperature for 1 hour and then concentrated. The crude product remaining as the residue was purified by HPLC (C-18 phase; gradient: water/ethanol with 0.1% trifluoroacetic acid), whereby 79 mg of 4,5-cyclo-[acetyl-L-glutamyl-L-arginyl-glycyl-L-aspartyl-L-valyl-L-tyrosyl-aminomethyl]-3,6-dimethoxy-9,9-dimethylxanthene trifluoroacetate(4,5-cyclo-[acetyl-SEQ ID NO:7-aminomethyl]-3,6-dimethoxy-9,9-dimethylxanthene trifluoroacetate) were obtained; IR 3379, 2966, 1663 and 1516 $cm^{-1}$; MS: 1058.4 $(M+H)^+$.

EXAMPLE 1.5.1

20 g of p-hydroxymethylphenoxy-polystyrene resin were suspended in 250 ml of DMF in a peptide synthesizer and then treated in succession with 9.88 g of Fmoc-Asp-OAllyl [A. Trzeciak, W. Bannwarth; Tetrahedron Letters, 33, 4557–4560 (1992)], 4.45 ml of DIPEA and 317 mg of 4-dimethylaminopyridine, whereupon the mixture was shaken at room temperature for 18 hours. The esterified resin was washed with dimethylformamide, isopropanol and diethyl ether and dried in a vacuum, there being obtained 23.8 g of loaded resin (0.4 mmol/g).

4g of the loaded resin were subjected to the synthesis cycle according to Example 2.2.2. and coupled with the amino acid derivatives Fmoc-Pro-OH, Fmoc-Phe-OH, Fmoc-Asp(OBut)-OH, Fmoc-Gly-OH, Fmoc-Arg(Pmc)-OH, Fmoc-Ala-OH and Fmoc-Ile-OH. After completion of the synthesis the resin was dried; yield 6 g.

0.8 g of the resin obtained was treated with 10 ml of a 20% solution of piperidine in DMF, whereupon it was coupled with 170 mg of 5-[(9-fluorenylmethoxyformamido) methyl]-3,6-dimethoxy-9,9-dimethylxanthene-4-acetic acid and 103 mg of TBTU and 0.055 ml of DIPEA. In order to cleave the allyl ester, the resin was suspended in a mixture of 10.9 ml of DMSO, 10.9 ml of THF, 1.85 ml of methylaniline and 5.45 ml of 0.5N HCl under an argon atmosphere, whereupon 107 mg of $Pd^0$ $[P(C_6H_5)_3]_4$ were added and the mixture was shaken for 18 hours [see Williams, P. L., et al. Tetrahedron Lett. 1991, 32, 4207.]. The resin was washed with DMF and the Fmoc protecting group was removed using piperidine (20% in DMF). For the cyclization, the resin was suspended in 10 ml of DMF and treated with 160 mg of TBTU and 0.085 ml of DIPEA, whereupon the mixture was shaken for 3 hours and subsequently washed with DMF, isopropanol and diethyl ether. The resin was thereupon suspended in 40 ml of a mixture of 82.5% trifluoroacetic acid, 5% phenol, 5% water, 5% thioanisole and 2.5% ethanedithiol, whereupon the mixture was shaken for 2 hours and then filtered. The filtrate was concentrated in a vacuum and the residue was digested with diethyl ether. The purification was effected analogously to that described in Example 2.2.1. and 44 mg of 4,5-cyclo-[acetyl-L-isoleucyl-L-alanyl-L-arginyl-glycyl-L-aspartyl-L-phenylalanyl-L-prolyl-L-aspartyl-aminomethyl]-3,6-dimethoxy-9,9-dimethylxanthene trifluoroacetate(4,5-cyclo-[acetyl-SEQ ID NO:8-aminomethyl]- 3,6-dimethoxy-9,9-dimethylxanthene trifluoroacetate) were obtained; MS: 1211.7 $(MH^+)$.

EXAMPLE 1.5.2

The following compounds were manufactured analogously to that described in Example 1.5.1.:

a) 4,5-Cyclo-[acetyl-L-alanyl-L-arginyl-L-isoleucyl-L-alanyl-L-arginyl-glycyl-L-aspartyl-L-phenylalanyl-L-prolyl-L-aspartyl-L-aspartyl-L-arginyl-aminomethyl]-3,6-dimethoxy-9,9-dimethylxanthene trifluoroacetate, (4,5-cyclo-[acetyl-SEQ ID NO:11-aminomethyl]-3,6-dimethoxy-9,9-dimethylxanthene trifluoroacetate) FAB-MS: 1710;

b) 4,5-cyclo-[acetyl-L-alanyl-L-arginyl-glycyl-L-aspartyl-L-phenylalanyl-L-prolyl-aminomethyl]-3,6-dimethoxy-9,9-dimethylxanthene trifluoroacetate, (4,5-cyclo-[acetyl-SEQ ID NO:6-aminomethyl]-3,6-dimethoxy-9,9-dimethylxanthene trifluoroacetate) FAB-MS: 984;

c) 4,5-cyclo-[acetyl-L-arginyl-glycyl-L-aspartyl-L-3,6-dimethoxy-9,9-dimethylxanthene trifluoroacetate, (4,5-cyclo-[acetyl-SEQ ID NO:12-aminomethyl]-3,6-dimethoxy-9,9-dimethylxanthene trifluoroacetate) FAB-MS:816;

d) 4,5-cyclo-[acetyl-L-arginyl-L-isoleucyl-L-alanyl-L-arginyl-glycyl-L-aspartyl-L-phenylalanyl-L-prolyl-L-aspartyl-L-aspartyl-aminomethyl]-3,6-dimethoxy-9,9-dimethylxanthene trifluoroacetate, (4,5-cyclo-[acetyl-SEQ ID NO:10-aminomethyl]-3,6-dimethoxy-9,9-dimethylxanthene trifluoroacetate) FAB-MS: 1482

EXAMPLE 1.5.3

0.6 g (0.26 mmol) of Fmoc-Lys(Boc)-Sasrin$^R$ (Bachem AG, D-1 365, see EP 0 292 729 A2) was subjected to the synthesis cycle according to Example 2.2.2 herein below and coupled in sequence with Fmoc-Arg(Pmc)-OH, Fmoc-Val-OH, 5-[(9-fluorenylmethoxyformamido)methyl]-3,6-dimethoxy-9,9-dimethylxanthene-4-acetic acid and Fmoc-Ile-OH. After completion of the synthesis the peptide resin was washed several times with methylene chloride and subsequently shaken two to four times with 50 ml of a solution of 2% TFA in methylene chloride for 2 minutes. The resin was filtered off and the filtrate was neutralized with pyridine and evaporated in a vacuum. The residue was partitioned between ethyl acetate and 5% $KHSO_4$/10% $K_2SO_4$ solution, whereupon the organic phase was washed neutral thoroughly with dist. water and concentrated in a vacuum. The residue obtained was taken up twice in toluene and the toluene was evaporated in a vacuum each time. In order to remove the Fmoc group, the residue was dissolved in 10 ml of a 20% solution of piperidine in DMF, whereupon the solution was left to stand at room temperature for 20 min. and subsequently concentrated in a vacuum. The residue was digested several times with hexane and subsequently cyclized, deblocked and purified as described in Example 2.2.2.c. There were obtained 26 mg of 4,5-Cyclo[acetyl-L-valyl-L-arginyl-L-lysyl-L-isoleucyl-aminomethyl]-3,6-dimethoxy-9,9-dimethylxanthene trifluoroacetate(4,5-cyclo-[acetyl-SEQ ID NO:14-aminomethyl]-3,6-dimethoxy-9,9-dimethylxanthene trifluoroacetate) (1:2), MS (ISP) 836.6.

EXAMPLE 1.5.4

The following compounds were manufactured analogously to that described in Example 1.5.3.
a) 4,5-Cyclo-[acetyl-L-isoleucyl-L-valyl-L-arginyl-L-lysyl-L-lysyl-L-prolyl-aminomethyl]-3,6-dimethoxy-9,9-dimethylxanthene trifluoroacetate(4,5-cyclo-[acetyl-SEQ ID NO:15-aminomethyl]-3,6-dimethoxy-9,9-dimethylxanthene trifluoroacetate) (1:3), MS (ISP) 1061.4;
b) 4,5-cyclo-[acetyl-glycyl-D-arginyl-L-lysyl-D-isoleucyl-aminomethyl]-3,6-dimethoxy-9,9-dimethylxanthene trifluoroacetate(4,5-cyclo-[acetyl-SEQ ID NO:1 6-aminomethyl]-3,6-dimethoxy-9,9-dimethylxanthene trifluoroacetate) (1:2), MS (ISP) 794.6;
c) 4,5-cyclo-[acetyl-L-valyl-L-arginyl-L-lysyl-L-isoleucyl-aminomethyl]-3,6-dimethoxy-9,9-dimethylxanthene trifluoroacetate(4,5-cyclo-[acetyl-SEO ID NO: 14-aminomethyl]-3,6-dimethoxy-9,9-dimethylxanthene trifluoroacetate) (1:2), MS (ISP) 836.6; and
d) 4,5-cyclo-[acetyl-L-arginyl-L-lysyl-L-isoleucyl-L-glutamyl-L-isoleucyl-L-valyl-L-arginyl-L-lysyl-L-lysyl-L-prolyl-L-isoleucyl-L-phenylalanyl-L-lysyl-L-lysyl-aminomethyl]-3,6-dimethoxy-9,9-dimethylxanthene trifluoroacetate(4,5-cyclo-[acetyl-SEQ ID NO:17-aminomethyl]-3,6-dimethoxy-9,9-dimethylxanthene trifluoroacetate) (1:7), MS (ISP) 2105.0.

EXAMPLE 2.1.1.a 21.7 ml of tert-butyllithium solution (1.4M in pentane) were slowly added dropwise under argon at −78° to a solution of 5.0 g (23.4 mmol) of 10-methylphenothiazine in 10 ml of absolute diethyl ether and 7 ml of freshly distilled N,N,N',N'-tetramethylethylenediamine. The reaction mixture was subsequently brought slowly to room temperature, stirred for 18 hours, then cooled to 0° and thereupon treated with 3.90 ml (35.1 mmol) of N-formylpiperidine. The reaction mixture was stirred at room temperature for 2 hours and then poured into 50 g of ice, 50 ml of 0.1N aqueous hydrochloric acid solution and 1.50 ml of diethyl ether. The aqueous phase was extracted twice with 100 ml of diethyl ether and the combined organic fractions were dried over magnesium sulphate and concentrated. The residue was chromatographed on 500 g of silica gel with ethyl acetate/hexane (1:3), whereafter, after recrystallization from ethyl acetate/hexane, 4.20 g (74.4%) of 10-methyl-phenothiazine-4-carbaldehyde were obtained as a yellow solid of m.p. 103°.

EXAMPLE 2.1.1.b 12.0 ml of lithium borohydride solution (2M in tetrahydrofuran) were slowly added dropwise under an argon atmosphere and while cooling with ice to a solution of 10.0 g (41.4 mmol) of 10-methyl-phenothiazine-4-carbaldehyde in 135 ml of abs. tetra-hydrofuran. The reaction mixture was stirred at 0° for 30 minutes and then poured into 100 ml of 0.1N aqueous hydrochloric acid solution and 200 ml of ethyl acetate. The aqueous phase was extracted twice with 100 ml of ethyl acetate and the combined organic fractions were washed with saturated sodium chloride solution, dried over magnesium sulphate and concentrated. After crystallization from ethyl acetate/hexane and drying in a high vacuum 9.49 g (94.2%) of (10-methyl-phenotiazin-4-yl)methanol were obtained as a beige solid of m.p. 113°.

EXAMPLE 2.1.1.ca 22.3 ml (87.1 mmol) of tert-butyldiphenylsilyl chloride were slowly added dropwise to an ice-cooled solution of 17.66 g (72.6 mmol) of (10-methyl-phenothiazin-4-yl)methanol and 10.87 g (159.7 mmol) of imidazole in 220 ml of N,N-dimethylformamide. The reaction mixture was stirred at 0° for 30 minutes and at room temperature for 1 hour and then poured into 100 ml of 0.5N aqueous hydrochloric acid solution, 100 g of ice and 200 ml of diethyl ether. The aqueous phase was extracted with diethyl ether and the combined organic fractions were dried over magnesium sulphate and concentrated. The residue was crystallized from diethyl ether/hexane, whereupon 27.69 g (79.2%) of 4-(tert-butyl-diphenyl-silanyloxymethyl)-10-methyl-penothiazine were obtained as a light yellowish solid of m.p. 127°–128°.

EXAMPLE 2.1.1.cb 8.05 g (53.4 mmol) of tert-butyldimethylsiyl chloride were slowly added dropwise to an ice-cooled solution of 10.0 g (41.1 mmol) of (10-methyl-phenothiazin-4-yl)methanol and 6.16 g (90.4 mmol) of imidazole in 125 ml of N,N-dimethylformamide. The reaction mixture was stirred at 0° for 30 minutes and at room temperature for 1 hour and then poured into 50 g of ice, 50 ml of 0.1N aqueous hydrochloric acid solution and 250 ml of diethyl ether. The organic phase was separated, dried over magnesium sulphate and evaporated. The residue was chromatographed on 1 kg of silica gel with diethyl ether/hexane (1:10), whereupon 13.0 g (88.5%) of 4-(tert-butyl-dimethyl-silanyloxymethyl)-10-methyl-phenothiazine were obtained as a colourless oil. NMR (250 MHz, DMSO-$d_6$): 7.3–7.15 (m,3 arom. H); 7.1–7.0 (m, 1 arom. H); 7.0–6.85 (m, 3 arom. H); 4.68 (s, C$\underline{H}_2$O); 3.31 (s, MeN); 0.70 (s, OSi(CH$_3$)$_2$C(C$\underline{H}_3$)$_3$); 0.09 (s, OSi(C$\underline{H}_3$)$_2$C(CH$_3$)$_3$).

EXAMPLE 2.1.1.da 41.1 ml of tert-butyllithium solution (1.4M in pentane) were slowly added dropwise under argon and at −78° to a solution of 20.8 g (43.2 mmol) of 4-(tert-butyl-diphenyl-silanyloxymethyl)-10-methyl-penothiazine and 6.8 ml of N,N,N',N'-tetramethylethylenediamine in 125 ml of diethyl ether. The reaction mixture was stirred at 0° for 4 hours and at room temperature for a further 2 hours and then treated at 0° with 7.4 ml (66.5 mmol) of N-formylpiperidine. The crude 6-[(tert-butyldiphenylsilanyoxy)methyl]-10-methyl-10H-phenothiazine-4-carbaldehyde was reduced analogously to that described in Example 2.1.1.db. After chromatography on 1 kg of silica gel with diethyl ether/hexane (1:2) there were obtained, in addition to 4.0 g (19%) of 4-(tert-butyldiphenyl-silanyloxymethyl)-10-methyl-phenothiazine, 7.12 g. (32.2%) of [6-(tert-butyl-diphenyl-silanyloxymethyl)-10-methyl-phenothiazin-4-yl]-methanol as an amorphous solid. MS: 511 (M$^+$, 100) 439(52), 316(46), 238(36), 199(48), 139(58) 91(20).

EXAMPLE 2.1.1.db 36.4 ml of tert-butyllithium solution (1.4M in pentane) were slowly added dropwise under argon at –78° to a solution of 14.0 g (39.2 mmol) of 4-(tert-butyl-dimethyl-silanyloxymethyl)-10-methyl-phenothiazine and 6.39 ml of N,N,N',N'-tetramethylethylenediamine in 120 ml of diethyl ether. The reaction mixture was stirred at –78° for 30 minutes, brought slowly to room temperature, stirred for 3 hours, thereupon treated with 5.66 ml (51.0 mmol) of N-formylpiperidine, stirred at 0° for 40 minutes and then poured into 50 g of ice, 50 ml of 0.1N aqueous hydrochloric acid solution and 250 ml of diethyl ether. The aqueous phase was extracted several times with diethyl ether. The combined organic phases were dried over magnesium sulphate and concentrated. The crude 6-(tert-butyl-dimethyl-silanyloxymethyl)-10-methyl-phenothiazine-4-carbaldehyde (about 14 g) remaining as the residue was dried in a high vacuum, dissolved in 120 ml of tetrahydrofuran and treated at 0° with 50 ml of lithium borohydride solution (1N in tetrahydrofuran). The reaction mixture was stirred at room temperature for 1 hour and then poured into 100 ml of 0.1N aqueous hydrochloric acid solution, 100 g of ice and 150 ml of diethyl ether. The aqueous phase was extracted with diethyl ether and the combined organic fractions were dried over magnesium sulphate and concentrated. The residue was chromatographed on 1.3 kg of silica gel with ethyl acetate/hexane (1:4), whereupon, after drying in a high vacuum, 4.57 g (30.0%) of [6-(tert-butyl-dimethyl-silanyloxymethyl)-10-methyl-phenothiazin-4-yl]-methanol were obtained as a colourless oil. MS: 387 (M$^+$; 100), 238(91), 224(24), 75(97).

EXAMPLE 2.1.1.ea 2.90 ml (18.43 mmol) of diethyl azodicarboxylate were slowly added dropwise under argon and while cooling with ice to a solution of 7.1 g (14.18 mmol) of [6-(tert-butyl-dimethyl-silanyloxymethyl)-10-methyl-phenothiazin-4-yl]-methanol, 3.13 g (21.3 mmol) of phthalimide and 4.20 g (16.0 mmol) of triphenylphosphine in 110 ml of tetrahydrofuran. The reaction mixture was stirred at 0° for 2.5 hours and then poured into 100 g of ice, 100 ml of water and 200 ml of ethyl acetate/hexane (1:1). The organic phase was separated, washed with water, dried over magnesium sulphate and concentrated. The residue was chromatographed on 1 kg of silica gel with toluene/ethyl acetate (20:1), whereupon, after crystallization from ethyl acetate/hexane, 6.87 g (77.3%) of 2-[6-(tert-butyl-diphenylsilanyloxy)-methyl-10-methyl-phenothiazin-4-yl-methyl]-2,3-dihydro-1H-isoindole-1,3-dione were obtained as a light yellowish solid of m.p. 182°–184°.

EXAMPLE 2.1.1.eb 1.62 ml (10.34 mmol) of diethyl azodicarboxylate were slowly added dropwise while cooling with ice and under argon to a solution of 3.09 g (7.97 mmol) of [6-(tert-butyl-dimethyl-silanyloxymethyl)-10-methyl-phenothiazin-4-yl]-methanol, 1.76 g (11.9 mmol) of phthalimide and 2.30 g (8.75 mmol) of triphenylphosphine in 65 ml of tetrahydrofuran. The reaction mixture was stirred at 0° for 3 hours and then worked-up analogously to that described in Example 2.1.1.ea. The residue was chromatographed on 500 g of silica gel with toluene/ethyl acetate (19:1), whereupon, after crystallization from ethanol/ethyl acetate, 3.22 g (78.2%) of 2-[6-(tert-butyl-dimethyl-silanyloxymethyl)-10-methyl-phenothiazin-4-ylmethyl]-2,3-dihydro-1H-isoindole-1,3-dione were obtained as a light yellow solid of m.p. 195°–196°.

EXAMPLE 2.1.1.fa

A solution of 6.53 g (10.38 mmol) of 2-[6-(tert-butyl-diphenyl-silanyloxymethyl)-10-methyl-phenothiazin-4-ylmethyl]-2,3-dihydro-1H-isoindole-1,3-dione in 50 ml of methylene chloride was reacted with 11.5 ml of boron tribromide solution (1M in methylene chloride) and 5.1 g of sodium cyanide analogously to that described in Example 2.1.1.fb, whereupon, analogously to that described in Example 2.1.1.fb after recrystallization from toluene/acetonitrile, 3.82 g (89.4%) of [6-(1,3-dioxo-2,3-dihydro-1H-isoindol-2-ylmethyl)-10-methyl-phenothiazin-4-yl]-acetonitrile of m.p. 245°–247° were obtained.

EXAMPLE 2.1.1.fb 4.5 ml of boron tribromide solution (1M in methylene chloride) were slowly added dropwise while cooling with ice to a solution of 2.1 g (4.06 mmol) of 2-[6-(tert-butyl-dimethyl-silanyloxymethyl)-10-methyl-phenothiazin-4-ylmethyl]-2,3-dihydro-1H-isoindole-1,3-dione in 15 ml of methylene chloride. The reaction mixture was stirred at 0° for 10 minutes, brought to room temperature, stirred at 65° under argon for 1 hour, then cooled and poured into ice, 1M sodium dihydrogen phosphate solution and methylene chloride. The organic phase was separated, dried over magnesium sulphate and concentrated; the residue was dried in a high vacuum for 2 hours and then dissolved in 10 ml of N,N-dimethylformamide. The solution was treated with 2.0 g (46.0 mmol) of sodium cyanide and the reaction mixture was stirred at 65° for 1 hour, cooled and poured into ice-water. The suspension obtained was stirred for 1 hour and filtered; the filter residue was washed with water and dried in a high vacuum over-phosphorus pentoxide. After recrystallization from toluene/acetonitrile 2.32 g (93.3%) of [6-(1,3-dioxo-2,3-dihydro-1H-isoindol-2-ylmethyl)-10-methyl-phenothiazin-4-yl]-acetonitrile as colourless crystals of m.p. 245°–247° were obtained.

EXAMPLE 2.1.1.ga 4.0 ml of hydrazine hydrate solution (1M in methanol) were added dropwise to a solution of 823 mg (2.0 mmol) of [6-(1,3-dioxo-2,3-dihydro-1H-isoindol-2-ylmethyl)-10-methyl-phenothiazin-4-yl]-acetonitrile in 10 ml of dioxan. The reaction mixture was stirred at 80° for 3 hours, cooled, mixed with 50 ml of 10% aqueous sodium carbonate solution and 50 ml of methylene chloride and extracted thoroughly. The aqueous phase was extracted twice with 30 ml of methylene chloride. The combined organic phases were dried over magnesium sulphate and evaporated, and the residue was dried in a high vacuum. The resulting 6-aminomethyl-10-methyl-phenothiazine-4-acetonitrile was dissolved in 20 ml of dioxan. The solution was treated with 20 ml of fuming hydrochloric acid, heated at 100° for 2 hours, cooled and evaporated to dryness, and the residue was dried in a high vacuum. The resulting amorphous 6-aminomethyl-10-methyl-phenothiazine-4-acetic acid was taken up in 20 ml of dioxan/water (2:1). The solution was made basic dropwise with 1N aqueous sodium hydroxide solution, treated with a solution of 546 mg (2.5 mmol) of di-tert.butyl dicarbonate in 5 ml of dioxan while cooling with ice and then slowly brought to room temperature. The reaction mixture was stirred at room temperature for 1 hour and then poured into ice-water and methylene chloride, whereupon the mixture was made acid with 1N hydrochloric acid solution and the aqueous phase was extracted twice with methylene chloride. The combined organic fractions were dried over magnesium sulphate and concentrated, and the residue was chromatographed on 100 g of silica gel with chloroform/methanol (9:1), whereupon 660 mg (82.3%) of (6-tert-butoxycarbonyl-aminomethyl-10-methyl-phenothiazin-4-yl)-acetic acid were obtained as an amorphous solid. IR(KBr): 3413w, 3060w, 2975w, 2929w, 1708s, 1678s, 1597s, 1563s, 1503w, 1457s, 1426s, 1394s, 1283m, 1249m, 1167s, 1051w, 757w.

EXAMPLE 2.1.1.gb1

15.0 ml of triethyl orthoformate were added at room temperature to a solution of 4.90 g (20.3 mmol) of 10-methyl-phenothiazine-4-carbaldehyde and 50 mg of p-toluenesulphonic acix1H$_2$O in 15 ml of methanol. The reaction mixture was boiled at reflux for 45 minutes, cooled and poured into 30 g of ice, 30 ml of saturated aqueous sodium hydrogen carbonate solution and 100 ml of diethyl ether. The organic phase was washed with 50 ml of saturated sodium chloride solution, dried over magnesium sulphate and concentrated. The residue was chromatographed on 300 g of silica gel with diethyl ether/hexane (1:4), whereupon, after crystallization from diethyl ether/hexane in a refrigerator, 6.16 g (96.2%) of 4-diethoxymethyl-10-methyl-phenothiazine were obtained as a white solid of m.p. 44.6°–46.2°.

EXAMPLE 2.1.1.gb 2

7.4 ml of tert-butyllithium solution (1.4M in pentane) were slowly added dropwise under argon and at −78° to a solution of 2.5 g (7.93 mmol) of 4-diethoxymethyl-10-methyl-phenothiazine and 2.4 ml of N,N,N',N'-tetramethylethylenediamine in 25 ml of diethyl ether. The reaction mixture was brought slowly to room temperature, stirred for 3.5 hours and then treated with 1.32 ml (11.9 mmol) of N-formylpiperidine. The reaction mixture was stirred at 0° for 1 hour and then poured into 30 g of ice, 30 ml of 0.1N aqueous hydrochloric acid solution and 70 ml of ethyl acetate. The aqueous phase was extracted with ethyl acetate and the combined organic phases were dried over magnesium sulphate and evaporated. The residue was chromatographed on 200 g of silica gel with ethyl acetate/hexane (1:4), whereupon 310 mg (12.4%) of starting product and, after crystallization from ethyl acetate/hexane, 520 mg (19%) of 6-diethoxymethyl-10-methyl-phenothiazine-4-carbaldehyde were obtained as a yellow solid of m.p. 154°–154.5°.

EXAMPLE 2.1.1.gb 3

A solution of 500 mg (1.46 mmol) of 6-diethoxymethyl-10-methyl-phenothiazine-4-carbaldehyde in 5 ml of tetrahydrofuran can be converted analogously to that described in Example 1.1.1.d with 0.22 g (1.75 mmol) of methyl (methylthiomethyl)sulphoxide, 0.14 ml of Triton B solution (35% in methanol) and hydrolysis into methyl 6-formyl-10-methyl-phenothiazine-4-acetate. This compound can be converted analogously to that described in Example 1.1.1.e in methanol, water and tetrahydrofuran using sodium acetate and hydroxylamine hydrochloride into methyl 6-[(hydroximino)methyl]-10-methyl-phenothiazine-4-acetate. This compound can be hydrogenated over palladium/charcaol in methanol and methanolic hydrochloric acid (20%) analogously to that described in Example 1.1.1.f, whereby there is obtained methyl 6-aminomethyl-10-methyl-phenothiazine-4-acetate hydrochloride which can be converted analogously to that described in Example 1.1.2 in dioxan and 1N sodium hydroxide solution using di-tert-butyl dicarbonate into methyl 6-[(1-tert-butylformamido) methyl]-10-methyl-phenothiazine-4-acetate. The product obtained can be hydrolyzed with 1N potassium hydroxide solution in methanol analogously to that described in Example 1.1.3 to give (6-tert-butoxycarbonyl-aminomethyl-10-methyl-phenothiazin-4-yl)-acetic acid prepared according to Example 2.1.1.g.

EXAMPLE 2.1.2

1 ml of diazomethane solution (~0.3N in diethyl ether) was added dropwise while cooling with ice to a solution of 80 mg (0.19 mmol) of (6-tert-butoxycarbonyl-aminomethyl-10-methyl-phenothiazin-4-yl)-acetic acid in 4 ml of methylene chloride. The reaction mixture was brought to room temperature, stirred for 1.5 hours and evaporated. The residue was crystallized from ethyl acetate/hexane, whereupon, after drying in a high vacuum, 72 mg (91%) of methyl (6-tert-butoxycarbonyl-aminomethyl-10-methyl-phenothiazin-4-yl)-acetate were obtained as a white solid. MS 414 (M$^+$, 64), 358 (100), 343 (15), 314 (15), 238 (15), 57 (16).

EXAMPLE 2.1.3

A solution of 823 mg (2.0 mmol) of [6-(1,3-dioxo-2,3-dihydro-1H-isoindol-2-ylmethyl)-10-methyl-phenothiazin-4-yl]acetonitrile was treated firstly with 4.0 ml of hydrazine hydrate solution (1M in methanol) and then with 20 ml of fuming hydrochloric acid analogously to that described in Example 2.1.1.g. The residue was dried in a high vacuum for 3 hours and dissolved in 20 ml of dioxan/water (2:1). The solution was made basic dropwise with 10% aqueous sodium carbonate solution and treated with a solution of 650 mg (2.51 mmol) of fluorenylmethyl chlorocarbonate in 5 ml of dioxan while cooling with ice. The reaction mixture was brought slowly to room temperature, stirred for 1 hour, made acid with 1N aqueous hydrochloric acid solution and poured into ice-water. The mixture was extracted with methylene chloride. The organic phase was dried over magnesium sulphate and concentrated. The residue was chromatographed on 80 g of silica gel with chloroform/methanol (18:1), whereupon, after recrystallization from ethanol, 784 mg (75%) of [6-(fluoren-9-ylmethoxycarbonyl-aminomethyl)-10-methyl-phenothiazin-4-yl]-acetic acid were obtained as a beige solid of m.p. 217°–219°.

EXAMPLE 2.1.4

20 mg of N,N-dimethylaminopyridine and a solution of 455 mg (2.2 mmol) of N,N-dicyclohexylcarbodiimide in 5 ml of methylene chloride were added while cooling with ice to a solution of 801 mg (2.0 mmol) of (6-tertbutoxycarbonyl-aminomethyl-10-methyl-phenothiazin-4-yl)-acetic acid and 324.5 mg (3.0 mmol) of benzyl alcohol in methylene chloride. The reaction mixture was stirred at 0° for 15 minutes, brought slowly to room temperature, stirred for 2 hours and then poured into ice and saturated sodium hydrogen carbonate solution, whereupon the mixture was extracted three times with methylene chloride. The combined organic phases were dried over magnesium sulphate and evaporated. The residue was chromatographed on 100 g of silica gel with ethyl acetate/hexane (3:2), whereupon 730 mg (74.4%) of benzyl (6-tert.-butoxycarbonyl-aminomethyl-10-methyl-phenothiazin-4-yl)-acetate were obtained as an amorphous solid. MS: 490 ($M^+$78), 434(100), 416(22), 390(20), 91(60).

EXAMPLE 2.1.5

3 ml of trifluoroacetic acid were slowly added dropwise while cooling with ice to a solution of 730 mg (1.48 mmol) of benzyl (6-tert.-butoxycarbonyl-aminomethyl-10-methyl-phenothiazin-4-yl)-acetate in 3 ml of methylene chloride. The reaction mixture was stirred at 0° for 2 hours, whereupon the solvent was removed in a vacuum and the residue was dried in a high vacuum. The residue was treated with 10 ml of diethyl ether. The suspension was stirred for 1 hour and filtered. The white residue was washed with diethyl ether and dried in a high vacuum, whereupon 720 mg (96.4%) of benzyl [6-aminomethyl-10-methyl-phenothiazin-4-yl]-acetate trifluoroacetate (1:1) were obtained as a white solid of m.p. 192°.

EXAMPLE 2.1.6.a 38.6 ml of tert-butyllithium solution (1.4M in hexane) were slowly added dropwise at −78° under argon and while stirring to a solution of 11.80 g (41.6 mmol) of 10-hexyl-phenothiazine in 125 ml of abs. diethyl ether and 12.5 ml of N,N,N,N-tetramethylethylenediamine. The reaction mixture was stirred at −75° for 16 hours, brought slowly to 0°, treated with 6.92 ml (1.5 eq.) of N-formylpiperidine, stirred at 0° for 1 hour and then poured into ice, 100 ml of 0.1N hydrochloric acid solution and 250 ml of ethyl acetate. The organic phase was washed with saturated sodium chloride solution, dried over magnesium sulphate and concentrated. The residue was chromatographed on 1 kg of silica gel with ethyl acetate/hexane (1:1), whereupon 6.33 g (48.8%) of 10-hexyl-phenothiazine-4-carbaldehyde were obtained as a light yellowish oil. IR (film): 3064w, 2927m, 2854m, 2731w, 1689s, 1561m, 1455s, 1388w, 1336m, 1286m, 1259s, 1052w, 784m, 750m, 724m.

EXAMPLE 2.1.6.b 6 ml of lithium borohydride solution (2M in tetrahydrofuran) were slowly added dropwise under an argon atmosphere and while cooling with ice to a solution of 6.30 g (20.2 mmol) of 10-hexyl-phenothiazine-4-carbaldehyde in 60 ml of tetrahydrofuran. The reaction mixture was stirred at 0° for 30 minutes and poured into 100 g of ice, 100 ml of 0.1N hydrochloric acid solution and 200 ml of ethyl acetate. The organic phase was washed with saturated sodium chloride solution and concentrated; the residue was crystallized from ethyl acetate/hexane in a refrigerator. After filtration and drying in a high vacuum 5.75 g (90.8%) of (10-hexyl-phenothiazin-4-yl)-methanol of m.p. 73.5°–74.5° were obtained.

EXAMPLE 2.1.6.c 3.4 ml (13.27 mmol) of tert-butyidiphenylsilyl chloride were added dropwise to an ice-cooled solution of 3.20 g (10.21 mmol) of (10-hexyl-phenothiazin-4-yl)-methanol, 1.85 ml (13.27 mmol) of triethylamine and 62 mg of dimethylaminopyridine in 35 ml of methylene chloride. The reaction mixture was stirred at 0° for 30 minutes and at room temperature for 2 hours and then poured into 10 ml of 2N aqueous sodium dihydrogen phosphate solution, 20 g of ice and 30 ml of diethyl ether. The aqueous phase was extracted with diethyl ether and the combined organic phases were dried over magnesium sulphate and evaporated. The residue was chromatographed on 400 g of silica gel with diethyl ether/hexane (1:20), whereupon 5.40 g (95.8%) of 4-(tert-butyl-diphenyl-sitanyloxy-methyl)-10-hexyl-phenothiazine were obtained as a colourless oil. MS : 551 ($M^+$, 72). 494(100), 296(65). 211(62), 43(38).

EXAMPLE 2.1.6.d 7.4 ml of tert-butyllithium solution (1.4M in pentane) were slowly added dropwise under argon and at −78° to a solution of 4.40 g (7.97 mmol) of 4-(tert-butyl-diphenyl-silanyloxy-methyl)-10-hexyl-phenothiazine and 1.3 ml of N,N,N',N'-tetra-methylethylenediamine in 25 ml of diethyl ether. The reaction mixture was brought to 0°, stirred for 4 hours, then treated with 1.33 ml (11.96 mmol) of N-formylpiperidine and subsequently stirred at 0° for 40 minutes. The reaction mixture was worked-up analogously to that described in Example 2.1.1.db and the 6-(tert-butyldiphenylsilanyloxy)methyl]-10-hexyl-phenothiazine-4-carbaldehyde was reduced analogously to that described in Example 2.1.1 db. The residue was chromatographed on 400 g of silica gel with diethyl ether/hexane (1:3), whereupon 1.95 (42%) of [6-(tert-butyl-diphenyl-silanyloxymethyl)-10-hexyl-phenothiazin-4-yl]-methanol were obtained as a light yellowish amorphous foam. MS: 581 ($M^+$, 100), 439 (51), 386(30), 301(35), 199(40), 139(29), 43(36).

EXAMPLE 2.1.6.e 0.68 ml (4.36 mmol) of diethyl azodicarboxylate was slowly added dropwise under argon and while cooling with ice to a solution of 1.95 g (3.35 mmol) of [6-(tert-butyl-diphenyl-silanyloxymethyl)-10-hexyl-phenothiazin-4-yl]-methanol, 876 mg (5.03 mmol) of phthalimide and 968 mg (3.69 mmol) of triphenylphosphine in 25 ml of tetrahydrofuran. The reaction mixture was stirred at 0° for 2 hours and at room temperature for 20 minutes and then worked up analogously to that described in Example 2.1.1 ea. The residue was chromatographed on 250 g of silica gel with diethyl ether/hexane (1:3), whereupon, after precipitation from hexane, 1.74 g (73.1%) of 2-[6-(tert-butyl-diphenyl-silanyloxymethyl)-10-hexyl-phenothiazin-4-ylmethyl]-2,3-dihydro-1H-isoindole-1,3-dione were obtained as a light yellowish amorphous solid. MS: 710 ($M^+$, 100), 653(61), 506(16), 370(36), 308(41), 268(40), 224(21), 160(34), 130 (45), 43(43).

EXAMPLE 2.1.6.f

A solution of 1.5 g (1.41 mmol) of 2-[6-(tert-butyl-diphenyl-silanyloxymethyl)-10-hexyl-phenothiazin-4-ylmethyl]-2,3-dihydro-1H-isoindole-1,3-dione in 5 ml of methylene chloride was reacted with 1.5 ml of boron tribromide solution (1M in methylene chloride) and with 691 mg (14.1 mmol) of sodium cyanide analogously to that described in Example 2.1.1.fb. The reaction mixture was poured into ice-water and ethyl acetate. The organic phase was washed with saturated sodium chloride solution and concentrated. The residue was chromatographed on 120 g of silica gel with diethyl ether/hexane (1:3), whereupon 510 mg (75%) of [6-(1,3-dioxo-2,3-dihydro-1H-isoindol-2-ylmethyl)-10-hexyl-phenothiazin-4-yl]-acetonitrile were obtained as a light yellowish amorphous foam. MS: 481 ($M^+$, 100), 410(50), 396(70), 263(15), 140(15).

EXAMPLE 2.1.6.g

Analogously to that described in Example 2.1.1.ga, a solution of 500 mg (1.04 mmol) of [6-(1,3-dioxo-2,3-dihydro-1H-isoindol-2-ylmethyl)-10-hexyl-phenothiazin-4-yl]-acetonitrile in 5 ml of dioxan was treated with 2 ml of hydrazine hydrate solution (1M in ethanol) and the resulting 6-aminomethyl-10-hexyl-phenothiazin-4-yl)-acetonitrile was converted using a solution of fuming hydrochloric acid in dioxan into 6-aminomethyl-10-hexyl-phenothiazine-4-acetic acid which was then reacted with 273 mg (1.25 mmol) of di-tert-butyl dicarbonate in dioxan analogously to that described in Example 2.1.1.ga. After chromatography on silica gel with chloroform/methanol (9:1) 395 mg (85%) of 6-[(1-tert-butoxyformamido)methyl]-10-hexylphenothiazine-4acetic acid were obtained as an amorphous solid. MS (FAB): 447 ($M^+$+1), 446 ($M^+$).

EXAMPLE 2.2.1

A solution of 75 mg of benzyl [6-aminomethyl-10-methyl-phenothiazin-4yl]-acetate trifluoroacetate (1:1) in 3 ml of N,N-dimethylformamide (DMF) was treated with 135 mg of $N^\alpha,N^G,N^E$ tris-(benzyloxycarbonyl)-L-arginine-N-hydroxysuccinimide ester. The pH value was adjusted to 8.5 with N-methylmorpholine, whereupon the reaction mixture was stirred at 20° for 1 hour and then poured, into dilute $NaHCO_3$ solution. The precipitated product was filtered off, rinsed with 5% $KHSO_4$/10%. $K_2SO_4$ solution and dist. water and then digested with ethanol. The crystalline solid was dissolved in trifluoroethanol and hydrogenated in the presence of 10% Pd-C. The catalyst was filtered off and the filtrate was evaporated. The residue was dissolved in 3 ml of DMF and treated with 20.3 mg of 1-hydroxybenzotriazole $H_2O$ and 0.05 ml of diisopropylethylamine. This solution was added dropwise while stirring within 10 minutes to a solution of 89 mg of O-(1,2-dihydro-2-oxo-1-pyridyl)-N,N,N',N'-tetramethyluronium tetrafluoroborate in 20 ml of DMF. The reaction mixture was stirred for a further 30 minutes and concentrated in a vacuum. The crude product remaining as the residue was purified by HPLC on a Zorbase ODS $C_{18}$ (8 μm) column in the gradient system 0.1% trifluoroacetic acid-ethanol. 18.2 mg of lyophilized (S)-8-(3-guanidinopropyl)17-methyl-1,15-imino-6,7,8,9,10,11-hexahydro-5H-dibenzo[b,k][1,5,8]thiadiazacyclodecine-7,10-dione trifluorocetate (1:1) were obtained. MS: 439 ($M^+$, 10), 327(25), 237(60).

EXAMPLE 2.2.2

(a) 4 g of 4-(2',4'-dimethoxyphenyl-hydroxymethyl) phenoxypolystyrene resin (Novabiochem, 01-64-0012) were filled into a peptide synthesizer [Labortec SP G40]. The resin was suspended in 40 ml of DMF and treated in succession with 3.3 g of (Fmoc-Val)$_2$O, 61 mg of 4-dimethylaminopyridine and 0.85 ml of diisopropylethylamine and shaken at 20° for 3 hours. The esterified resin was then subjected to the following synthesis cycle.

| Step | Reagent | Time |
|---|---|---|
| 1 | DMF | 2 × 1 min. |
| 2 | 20% piperidine/DMF | 1 × 7 min. |
| 3 | DMF | 5 × 1 min. |
| 4 | 2.5 eq. Fmoc- or Z-amino acid/DMF + 2.5 eq. 1-benzotriazol-1-yl-tetramethyluronium hexafluorophosphate + 2.5 eq. diisopropylethylamine | 1 × 90 min. |
| 5 | DMF | 3 × 1 min. |
| 6 | isopropyl alcohol | 2 × 1 min. |

30 ml of solvent were used in each step. Fmoc-Asp (OBut)-OH, Fmoc-Gly-OH and Z-Arg(Pmc)-OH were coupled according to the above protocol. After completion of the synthesis the peptide resin was suspended in 60 ml of acetic acid/methylene chloride (1:2) and shaken for 20 minutes, whereupon the resin was filtered off and the filtrate was concentrated. The residue was partitioned between ethyl acetate and water. The organic phase was washed with saturated sodium chloride solution and dried over sodium sulphate. The resulting Z-Arg(Pmc)-Gly-Asp(OBut)-Val-OH was precipitated from ethyl acetate/hexane; yield: 1.05 g, MS: 902 $MH^+$.

b) 133 mg of 1-benzotriazol-1-yl-N,N,N',N'-tetramethyluronium hexafluorophosphate and 0.17 ml of diisopropylethylamine were added to a solution of 128 mg of benzyl 6-aminomethyl-10-methyl-phenothiazin-4-yl]-acetate trifluoroacetate (1:1) and 270 mg of Z-Arg(Pmc)-Gly-Asp(OBut)-Val-OH in 5 ml of DMF, whereupon the reaction mixture was stirred at 20° for 1 hour and then evaporated in a vacuum. The residue was partitioned between ethyl acetate and saturated $NaHCO_3$ solution. The organic phase was washed with saturated NaCl solution, dried over $Na_2SO_4$ and evaporated. The residue was digested with diethyl ether and there were obtained 260 mg of benzyl 6-[(((N$^\alpha$-benzyloxycarbonyl-N$^G$-(2,5,5,7,8)-pentamethyl-chroman-6-sulphonyl)-L-arginyl-glycyl-4-O-tert.-butyl-L-aspartyl-L-valyl)aminomethyl)-3,7-dimethoxy-10-methyl-phenothiazin-4-yl]-acetate; MS: 1274.5 $MH^+$ c) 255 mg of the product obtained were dissolved in 25 ml of trifluoroethanol and hydrogenated in the presence of 10% Pd-C. The catalyst was filtered off and the filtrate was evaporated. The residue was dissolved in 20 ml of DMF and treated with 0.2 ml of diisopropylethylamine. The solution obtained was added dropwise while stirring during 20 minutes to a solution of 379.2 mg of 1-benzotriazol-1-yl-N,N,N',N'-tetramethyluronium hexafluorophosphate in 50 ml of DMF. The mixture was stirred at 20° for 1 hour, subsequently concentrated in a vacuum and then poured into dil. sodium hydrogen carbonate solution, whereby a solid separated and was filtered off, rinsed on the filter with dist. water and dried. The amorphous powder obtained was dissolved in 20 ml of trifluoroacetic acid/0.2 ml of phenol/1 ml of water. The mixture was left to stand at 20° for 2 hours and then concentrated in a vacuum. The residue was digested with diethyl ether and lyophilized from acetic acid. The lyophilizate was purified as described in Example 2.2.1. and 15.8 mg of 10-methyl-4,6-cyclo-[acetyl-L-arginyl-glycyl-L-aspartyl-L-valyl-aminomethyl]-phenothiazine trifluoroacetate(10-methyl-4,6-cyclo-[acetyl-SEQ ID NO:2-aminomethyl]phenothiazine trifluoroacetate) (1:1) were obtained; MS 710 $MH^+$.

EXAMPLE 3.1.1. a 12.1 ml of dimethyl sulphate were added at room temperature while stirring well to a suspension of 20.0 g (85.0 mmol) of resorufin, 17.6 g of freshly powdered potassium carbonate and 10 drops of tris-[2-(2-methoxyethoxy)ethyl] amine in 150 ml of dioxan. The reaction mixture was subsequently stirred at 100° for 2 hours, cooled and then treated with 150 ml of water. The solid was filtered off, washed with water and dried over phosphorus pentoxide. 11.5 g (59.5%) of resorufin methyl ether of m.p. 240°–244° (dec.) were obtained.

21.2 g of sodium dithionite were added portionwise under argon at room temperature to a suspension of 10.0 g (44.0 mmol) of resorufin methyl ether in a mixture of 60 ml of water and 250 ml of acetone. The reaction mixture was then boiled at reflux under argon for 3 hours, cooled and treated with 100 ml of 5% sodium dithionite solution and 300 ml of ethyl acetate. The organic phase was separated, dried over magnesium sulphate and evaporated. The brown-green solid was dried in a vacuum, dissolved in 150 ml of dioxan and treated under argon with 18.4 g of potassium carbonate (powdered), 15 drops of tris-[2-(2-methoxyethoxy)ethyl] amine and 12.6 ml of dimethyl sulphate. The reaction mixture was heated to 100° under argon for 2 hours, then treated with 6.1 g of potassium carbonate and 4.2 ml of dimethyl sulphate, stirred at 100° under argon for 18 hours, cooled and poured into 100 g of ice, 150 ml of saturated sodium bicarbonate solution and 300 ml of ethyl acetate. The aqueous phase was extracted with 2×150 ml of ethyl acetate. The combined organic phases were dried over magnesium sulphate and evaporated, and the residue was chromatographed on 500 g of silica gel with hexane/diethyl ether (4:1). After recrystallization from ethyl acetate/hexane (1:2) 6.25 g (55.2%) of 3,7-dimethoxy-10-methyl-10H-phenoxazine were obtained as white needles. M.p. 125°–127°.

EXAMPLE 3.1.1. b 12.63 ml of n-butyllithium solution (1.6M in hexane) were slowly added dropwise at −78° to a suspension of 4.0 g (15.55 mmol) of 3,7-dimethoxy-10-methyl-10H-phenoxazine in 15 ml of tetrahydrofuran and 60 ml of diethyl ether. The reaction mixture was brought slowly to 0°, whereby at −20° a clear solution formed for a short time. At −10° a precipitate formed and the suspension was stirred at 0° for 2 hours, followed by the addition of 2.6 ml (1.5 eq.) of N-formylpiperidine and stirring at 0° for 1 hour. The reaction mixture was poured into ice/0.5N hydrochloric acid solution and diethyl ether, the aqueous phase was extracted twice with ethyl acetate and the combined organic phases were washed with saturated sodium chloride solution, dried over magnesium sulphate and evaporated. The solid orange residue was dissolved in 60 ml of tetrahydrofuran, whereupon 10 ml of a 2M lithium borohydride solution (in tetrahydrofuran) were added slowly at 0°. The mixture was stirred at 0° for 1 hour and then treated with 50 ml of saturated ammonium chloride solution, ice and diethyl ether. The aqueous phase was extracted twice with diethyl ether. The combined organic phases were dried over magnesium sulphate and concentrated. The residue was chromatographed on 180 g of $SiO_2$ with a mixture of hexane/ethyl acetate (2:3). After drying in a high vacuum and recrystallization from hexane/ethyl acetate 3.71 g (83.3%) of 3,7-dimethoxy-10-methyl-10H-dibenzo[b,e][1,4]oxazine-4-methanol of m.p. 65°–66° were obtained.

EXAMPLE 3.1.1.c 8.6 ml of n-butyllithium solution (1.6M in hexane) were added dropwise at −78° to a solution of 3.3 g (11.49 mmol) of 3,7-dimethoxy-10-methyl-10H-dibenzo[b,e][1,4] oxazine-4-methanol in 33 ml of absolute tetrahydrofuran, whereby a white precipitate formed. The reaction mixture was brought to 0°, stirred for 30 minutes, treated at 0° with 1.96 ml (1.5 eq.) of 2-(methoxyethoxy)methyl chloride, stirred at room temperature for 1 hour and then poured into ice, saturated ammonium chloride solution and diethyl ether. The organic phase was dried over magnesium sulphate and evaporated. The residue was chromatographed on silica gel with a mixture of ethyl acetate/hexane (1:2), whereupon, after drying in a high vacuum, 4.13 g (95.75%) of 3,7-dimethoxy-4-[[(2-methoxyethoxy)methoxy]methyl]-10-methyl-10H-dibenzo[b,e][1,4]oxazine were obtained as a colourless oil. MS: 375 ($M^+$, 100), 360(11), 270(14), 256 (21), 226(14).

EXAMPLE 3.1.1.d 8.9 ml of n-butyllithium solution were added under argon at −78° to a solution of 4.10 g (10.92 mmol) of 3,7-dimethoxy-4-[[(2-methoxyethoxy)methoxy]methyl]-10-methyl-10H-dibenzo[[b,e][1,4]oxazine in 10 ml of tetrahydrofuran and 40 ml of diethyl ether. The reaction mixture was brought slowly to 0° and stirred for 1.5 hours, whereupon the suspension was treated with 1.82 ml (1.5 eq.) of N-formylpiperidine, stirred at 0° for 30 minutes and poured into 100 g of ice, 100 ml of 0.1N hydrochloric acid solution and 150 ml of diethyl ether. The aqueous phase was extracted three times with chloroform and the combined organic phases were dried over $MgSO_4$ and evaporated. The reddish residue was dissolved in 50 ml of tetrahydrofuran and treated at 0° under argon with 5 ml of lithium borohydride solution (2M in tetrahydrofuran). The reaction mixture was stirred at 0° for 30 minutes and then poured into 50 g of ice, 50 ml of saturated ammonium chloride solution and diethyl ether. The aqueous phase was extracted twice with ethyl acetate and the combined organic phases were dried over $MgSO_4$ and evaporated. The residue was chromatographed on 200 g of silica gel with ethyl acetate/hexane (2:1), whereupon, after drying in a high vacuum, 3.90 g (88.1%) of 3,7-dimethoxy-6-[[(2-methoxyethoxy)methoxy] methyl]-10-methyl-10H-dibenzo[b,e][1,4]oxazine-4-methanol were obtained as a colourless solid of m.p. 68°–70°.

EXAMPLE 3.1.1.e 1.63 g (1.5 eq.) of phthalimide and 2.91 g (1.5 eq.) of triphenylphosphine were added portionwise while cooling with ice to a solution of 3.0 g (7.40 mmol) of 3,7-dimethoxy-6-[[(2-methoxyethoxy)methoxy]methyl]-10-methyl-10H-dibenzo[b,e][1,4]oxazine-4-methanol in 40 ml of tetrahydrofuran. Then, a solution of 2.06 g (1.6 eq.) of diethyl diazodicarboxylate in 10 ml of tetrahydrofuran was slowly added dropwise at 0° during 2 hours. The reaction mixture was stirred at 0° for 10 hours and then poured into 50 ml of water, 100 ml of hexane, 50 ml of methanol and 50 ml of ethyl acetate. The organic phase was separated, washed with saturated sodium chloride solution, dried over magnesium sulphate and concentrated. The residue was chromatographed on 200 g of silica gel with ethyl acetate/hexane (1:1), whereupon 3.61 g (93.7%) of N-[[3,7-dimethoxy-6-[ [(2-methoxyethoxy)methoxy]methyl]-10-methyl-10H-dibenzo[b,e][1,4]oxazin-1-yl]methyl]-2,3-dihydro-1H-isoindole-1,3-dione were obtained as an amorphous foam. MS: 534 ($M^+$, 100), 160(8).

EXAMPLE 3.1.1.f 9.0 ml of 33% hydrobromic acid in acetic acid were slowly added dropwise under argon to an ice-cooled solution of 5.73 g (10.72 mmol) of N-[[3,7-dimethoxy-6-[[(2-methoxyethoxy)methoxy]methyl]-10-methyl-10H-dibenzo[b,e][1,4]oxazin-1-yl]methyl]-2,3-dihydro-1H-isoindole-1,3-dione in 60 ml of methylene chloride. After stirring at room temperature for 45 minutes a further 2.5 ml of 33% hydrobromic acid in glacial acetic acid were added dropwise, whereupon the reaction mixture was stirred at room temperature for 2 hours and then poured into 100 g of ice, 100 ml of saturated sodium hydrogen carbonate solution and 50 ml of methylene chloride. The aqueous phase was extracted twice with methylene chloride. The combined organic phases were dried over magnesium sulphate and concentrated. The residue was dried in a high vacuum and subsequently dissolved in 60 ml of N,N-dimethylformamide and treated with 5.26 g of powdered sodium cyanide. The reaction mixture was stirred at 60° for 45 minutes, then cooled and poured into ice-water. After 2 hours the suspension was filtered and the filter residue was washed with water and dried over phosphorus pentoxide in a high vacuum, whereupon 4.66 g (95.3%) of N-[3,7-dimethoxy-6-(1,3-dioxo-2,3-dihydro-1H-isoindol-2-ylmethyl)-10-methyl-10H-dibenz[b,e][1,4]-oxazin-4-yl]-acetonitrile were obtained as a light yellowish solid of m.p. 215°–217°.

EXAMPLE 3.1.1.ga

A suspension of 270 mg (0.57 mmol) of [3,7-dimethoxy-6-(1,3-dioxo-2,3-dihydro-1H-isoindol-2-ylmethyl)-10-methyl-10H-dibenz[b,e][1,4]-oxazin-4-yl]-acetonitrile in 2 ml of dioxan and 2 ml concentrated hydrochloric acid was heated to 100° in a bomb tube for 1.5 hours, then cooled and poured into ice-water. The separated precipitate was filtered off, washed several times with water and dried over phosphorus pentoxide in a high vacuum. After recrystallization from acetone/methanol (1:1) 240 mg (88.7%) of [3,7-dimethoxy-6-(1,3-dioxo-2,3-dihydro-1H-isoindol-2-ylmethyl)-10-methyl-10H-dibenz[b,e][1,4]oxazin-4-yl]-acetic acid were obtained as a beige solid of m.p. >220° (dec.).

EXAMPLE 3.1.1.gb 2.0 ml of ethanolic hydrazine hydrate solution (1M) were added at room temperature to a suspension of 280 mg of [3,7-dimethoxy-6-(1,3-dioxo-2,3-dihydro-1H-isoindol-2-ylmethyl)-10-methyl-10H-dibenz[b,e][1,4]-oxazin-4-yl]-acetonitrile. The reaction mixture was heated to 85° for 4 hours, the cooled and poured into methylene chloride and 10% sodium carbonate solution. The aqueous phase was extracted with ethylene chloride and the combined organic fractions were dried over magnesium chloride and concentrated. The residue was dried in a high vacuum and, after recrystallization from tert.-butyl methyl ether/methanol, 180 mg (90.1%) of 6-aminomethyl-3,7-dimethoxy-10-methyl-10H-dibenzo[b,e][1,4]oxazine-4-acetonitrile were obtained as a beige solid of m.p. 167°–169° (dec.).

EXAMPLE 3.1.1.ha

A solution of 200 mg (0.42 mmol) of [3,7-dimethoxy-6-(1,3-dioxo-2,3-dihydro-1H-isoindol-2-ylmethyl)-10-methyl-10H-dibenz(b,e][1,4]oxazin-4-yl]-acetic acid in 1 ml of methanol was treated at room temperature with 1 ml of hydrazine hydrate solution (1M in ethanol) and the reaction mixture was stirred at 80° for 4 hours, then cooled and evaporated to dryness. The residue was suspended in 2 ml of dioxan and the suspension neutralized with 1N sodium hydroxide solution, treated with 140 mg (1.5 eq.) of di-tert-butyl dicarbonate and stirred at room temperature for 3 hours. The reaction mixture was poured into ice, 1N HCl solution and ethyl acetate, whereupon the organic phase was separated dried over MgSO$_4$ and evaporated. The residue was chromatographed on silica gel with chloroform/methanol (9:1), whereupon 121 mg (65%) of 6-[(1-tert-butoxyformamido)methyl]-3,7-dimethoxy-10-methyl-10H-phenoxazine-4-acetic acid were obtained as a yellowish amorphous solid. MS: 445 (M$^+$).

EXAMPLE 3.1.1.hb

A solution of 150 mg (0.46 mmol) of 6-aminomethyl-3,7-dimethoxy-10-methyl-10H-dibenzo[b,e][1,4]oxazine-4-acetonitrile in 2 ml of methanol was treated with 2 ml of 6N sodium hydroxide solution and heated at 110° in a bomb tube for 2 hours. The reaction mixture was evaporated to dryness and the residue was neutralized with 2N hydrochloric acid. After evaporating again the residue was dissolved in 2 ml of dioxan, whereupon the pH was adjusted to 8 with 1N sodium hydroxide solution and 151 mg (0.69 mmol) of di-tert-butyl dicarbonate were added. The reaction mixture was stirred at room temperature for 2 hours and then poured into ice/2N HCl solution and ethyl acetate. The organic phase was separated, dried over MgSO$_4$ and evaporated. The residue was chromatographed on silica gel with chloroform/methanol (9:1), whereupon 160 mg (78.3%) of 6-[(1-tert-butoxyformamido)methyl]-3,7-dimethoxy-10-methyl-10H-phenoxazine-4-acetic acid were obtained as a yellowish amorphous solid; MS: 445 (M$^+$).

EXAMPLE 3.1.2.a

A suspension of 5.0 g (21.3 mmol) of resorufin, 10 drops of tris-[2-(methoxyethoxy)ethyt]amine and 3.5 ml (1.5 eq.) of diethyl sulphate in 70 ml of dioxan was mixed at room temperature, stirred at 100° for 18 hours and then poured into a mixture of 50 g of ice and 50 ml of 2N hydrochloric acid solution. The precipitate was filtered off and the brown-orange filter residue was washed with water. After drying the residue in a desiccator over phosphorus pentoxide in a vacuum 4.15 g (80.8%) of resorufin ethyl ether were obtained.

A solution of 3.0 g (12.44 mmol) of this product in 130 ml of acetone and 16 ml of water was de-gassed using a nitrogen stream for 1 hour, then treated with 6.0 g of sodium dithionite, heated to 70° under nitrogen for 2-hours, cooled and poured into a mixture of 2% sodium dithionite solution and ethyl acetate. The organic phase was separated, dried over magnesium sulphate, filtered and concentrated. The residue was dried in a vacuum and mixed under argon at room temperature with 7.95 g (4.4 eq.) of potassium carbonate, 6.30 ml of diethyl sulphate, 20 drops of tris-[2-(methoxyethoxy)ethyl]amine and 45 ml of dioxan. The mixture was stirred at 100° for 48 hours, cooled and poured into water/diethyl ether. The aqueous phase was extracted with 2×100 ml of diethyl ether. The combined organic phases were washed with saturated sodium chloride solution, dried over magnesium sulphate and concentrated. The residue was chromatographed on 300 g of silica gel with a mixture of diethyl ether/hexane (1:12), whereupon, after recrystallization, 2.82 g (82.3%) of 3,7-diethoxy-10-ethyl-10H-phenoxazine of m.p. 69.0°–69.5° were obtained.

EXAMPLE 3.1.2.b 4.2 ml of n-butyllithium solution (1.6M in hexane) were slowly added dropwise at −78° under argon to a suspension of 1.35 g (4.51 mmol) of 3,7-diethoxy-10-ethyl-10H-phenoxazine in 4 ml of anhydrous tetrahydrofuran and 16 ml of diethyl ether. The reaction mixture was stirred at −78° for 15 minutes, brought slowly to 0° and stirred at 0° for a further 4 hours. Thereafter, 1.0 ml of N-formylpiperidine was added dropwise at 0°, whereupon the reaction mixture was poured into ice/0.5N hydrochloric acid solution and diethyl ether. The aqueous phase was extracted twice with diethyl ether. The combined organic phases were dried over magnesium sulphate and concentrated. The residue was dried in a high vacuum and dissolved in 20 ml of absolute tetrahydrofuran, whereupon 2.3 ml of lithium borohydride solution (2M in tetrahydrofuran) were added at 0°. The reaction mixture was stirred at 0° for 30 minutes and then poured into ice, saturated ammonium chloride solution and diethyl ether. The aqueous phase was extracted twice with diethyl ether. The combined organic phases were dried over magnesium sulphate and concentrated. The residue was chromatographed on 100 g of $SiO_2$ with hexane/diethyl ether (3:2). After drying in a high vacuum 970 mg (65.3%) of 3,7-diethoxy-10-ethyl-10H-dibenzo[b,e][1,4]oxazine-4-methanol were obtained as a white solid of m.p. 71.5–72.5.

EXAMPLE 3.1.2.ca 2.1 ml of n-butyllithium solution (1.6M in hexane) were added at −78° to a solution of 1.0 g (3.04 mmol) of 3,7-diethoxy-10-ethyl-10H-phenoxazine in 10 ml of absolute tetrahydrofuran. The reaction mixture was stirred at −78° for 30 minutes, brought slowly to 0°, treated with 0.45 ml of 2-(methoxyethoxy)methyl chloride, stirred at room temperature for 2 hours and then poured into ice, saturated sodium bicarbonate solution and diethyl ether. The aqueous phase was extracted twice with diethyl ether and the combined organic phases were dried over magnesium sulphate and evaporated. The residue was chromatographed on 100 g of silica gel with a mixture of diethyl ether/hexane (1:1), whereupon, after drying in a high vacuum, 1.13g (89%) of 10-ethyl-3,7-diethoxy-4-[[(2-methoxyethoxy)methoxy]methyl]-10H-dibenzo[b,e][1,4]oxazine were obtained as a colourless oil. MS: 417 ($M^+$; 100), 388(58), 313(20), 284 (44), 254(60), 226(30).

EXAMPLE 3.1.2.cb

A solution of 1.92 g (1.3 eq.) of tert-butyldimethylsilyl chloride in 10 ml of N,N-dimethylformamide was added dropwise while cooling with ice to a mixture of 3.23 g (9.80 mmol) of 3,7-diethoxy-10-ethyl-10H-dibenzo[b,e][1,4]oxazine-4-methanol and 1.47 g (2.2 eq.) of imidazole in 30 ml of N,N-dimethylformamide. The reaction mixture was stirred at 0° for 30 minutes, brought slowly to room temperature, stirred for 1 hour and then poured into 100 ml of water, 50 ml of diethyl ether and 50 ml of hexane. The organic phase was separated, extracted twice with water, dried over magnesium sulphate and concentrated. The residue was chromatographed on 250 g of silica gel with diethyl ether/hexane (1:10), whereupon, after drying in a high vacuum, 4.30 g (98.9%) of 10-methyl-3,7-diethoxyl-4-[(tert-butyl-dimethylsilyl)oxy]methyl]-10H-dibenzo[b,e][1,4]oxazine were obtained as a colourless solid of m.p. 77.5°–78.5°.

EXAMPLE 3.1.2.da

A solution of 1.13 g (2.70 mmol) of 10-ethyl-3,7-diethoxy-4-[[(2-methoxyethoxy)methoxy]methyl]-10H-dibenzo[b,e][1,4]oxazine in 2 ml of tetrahydrofuran and 8 ml of diethyl ether was reacted with 2.2 ml of n-butyllithium solution (1.6M in hexane) and 0.54 ml of N-formylpiperidine in analogy to Example 3.1.1.d. The reduction was also effected in analogy to Example 3.1.1.d. using 1.5 ml of lithium borohydride solution (2M in tetrahydrofuran). After chromatography of the crude product on 80 g of silica gel with diethyl ether/hexane (3:1) and drying in a high vacuum 880 mg (72.8%) of 10-ethyl-3,7-diethoxy-6-[[(2-methoxyethoxy)methoxy]methyl]-10H-dibenzo[b,e][1,4]oxazine-4-methanol were obtained as a colourless solid of m.p. 60°–62°.

EXAMPLE 3.1.2.db 7.33 ml of n-butyllithium solution (1.6M in hexane) were added dropwise under argon at −78° to a solution of 4.0 g (9.02 mmol) of 10-ethyl-3,7-diethoxy-4-[(tert-butyidimethylsilyl)oxy]methyl]-10H-dibenzo[b,e][1,4] oxazine in 40 ml of diethyl ether and 10 ml of tetrahydrofuran. The reaction mixture was brought to 0°, stirred for 3 hours; treated with 1.85 ml of N-formylpiperidine, stirred at 0° for 30 minutes and then poured into 50 g of ice, 50 ml of saturated sodium dihydrogen phosphate solution and 100 ml of diethyl ether. The aqueous phase was extracted twice with diethyl ether and the combined organic phases were dried over magnesium sulphate and evaporated. The residue was dried in a high vacuum, dissolved in 50 ml of tetrahydrofuran and treated at 0° with 5 ml of lithium borohydride solution (2M in tetrahydrofuran). The mixture was stirred at 0° for 30 minutes and then poured into 50 g of ice, 50 ml of saturated sodium dihydrogen phosphate solution and 100 ml of ethyl acetate. The organic phase was dried over magnesium sulphate and evaporated. The residue was chromatographed on 250 g of silica gel with diethyl ether/hexane (1:2), whereupon 3.90 g (91%) of 10-ethyl-3,7-diethoxy-6-[[(tert-butyidimethylsilyl)oxy]methyl]-10H-dibenzo[b,e][1,4]oxazine-4-methanol were obtained as a colourless oil. MS: 473 ($M^+$; 100), 444(32), 387(24), 238(24).

EXAMPLE 3.1.2.db

A solution of 700 mg (1.56 mmol) of 10-ethyl-3,7-diethoxy-6-[[(2-methoxyethoxy)methoxy]methyl]-10H-dibenzo[b,e][1,4]oxazine-4-methanol in tetrahydrofuran can be converted analogously to Example 3.1.1.e using triphenylphosphine, diethyl diazodicarboxylate and phthalimide into N-[[3,7-diethoxy-6-[[(2-methoxyethoxy)methoxy]methyl]-10-hexyl-10H-dibenzo[b,e][1,4]-oxazin-1-yl]methyl]-2,3-dihydro-1H-isoindole-1,3-dione. By treatment with hydrobromic acid in acetic acid and then with sodium cyanide in dimethylformamide there can be obtained therefrom analogously to that described in Example 3.1.1.f 3,7-diethoxy-10-ethyl-6-(1,3-dioxo-2,3-dihydro-1H-isoindol-2-yl)methyl)-dibenzo[b,e][1,4]oxazine-4-acetonitrile; m.p., >205° (dec.).

EXAMPLE 3.1.2.eb1

A solution of 1.64 g (1.2 eq.) of diethyl azodicarboxylate in 10 ml of tetrahydrofuran was slowly added dropwise at 0° over 2 hours to a solution of 3.73 g (7.87 mmol) of 10-ethyl-3,7-diethoxy-6-[[(tert-butyidimethylsilyl)oxy]methyl]-10H-dibenzo[b,e][1,4]oxazine-4-methanol, 2.27 g (1.5 eq.) of triphenylphosphine and 1.74 g (1.5 eq.) of phthalimide in 50 ml of absolute tetrahydrofuran. The reaction mixture was stirred at room temperature for 4 hours and then poured into 100 g of ice, 100 ml of hexane, 50 ml of diethyl ether and 50 ml of methanol. The organic phase was extracted twice with water, dried over magnesium sulphate and evaporated. The residue was chromatographed on 300 g of silica gel with diethyl ether/hexane (2:3), whereupon, after crystallization from ethyl acetate/hexane, 3.59 g (75.7%) of N-[[10-ethyl-3,7-diethoxy-6-[[(tert-butyldimethylsilyl)oxy]methyl]-10H-dibenzo[b,e][1,4] oxazin-1-yl]methyl]-2,3-dihydro-1H-isoindole-1,3-dione of m.p. 158°–159° were obtained.

EXAMPLE 3.1.2.eb2

7.0 ml of 33% hydrogen bromide solution in glacial acetic acid were slowly added dropwise while cooling with ice to a solution of 2.45 g (4.06 mmol) of N-[[10-ethyl-3,7-diethoxy-6-[[(tert-butyldimethylsilyl)oxy]methyl]-10H-dibenzo[b,e][1,4]oxazin-1-yl]methyl]-2,3-dihydro-1H-isoindole-1,3-dione in 20 ml of methylene chloride. The reaction mixture was brought slowly to room temperature, stirred for 1.5 hours and then poured into 50 g of ice, 40 ml of saturated sodium hydrogen carbonate solution and 20 ml of methylene chloride. The aqueous phase was extracted twice with methylene chloride. The combined organic phases were dried over magnesium sulphate and evaporated. The residue was dried in a high vacuum, dissolved in 15 ml of N,N-dimethylformamide and treated with 2.64 g of powdered sodium cyanide. The reaction mixture was stirred at 60° for 1 hour, then cooled and poured into ice-water. The resulting suspension was stirred at room temperature for 1 hour and then filtered. The filter residue was washed with water and dried over phosphorus pentoxide in a high vacuum. After recrystallization from acetone/ethanol (1:1) 1.91 g (94.9%) of [3,7-diethoxy-10-ethyl-6-(1,3-dioxo-2,3-dihydro-1H-isoindol-2-ylmethyl)-dibenz[b,e][1,4]oxazin-4-yl]-acetic acid of m.p. >205° (dec.) were obtained.

EXAMPLE 3.1.2.f

A solution of 1.0 g (2.72 mmol) of [3,7-diethoxy-10-ethyl-6-(1,3-dioxo-2,3-dihydro-1H-isoindol-2-ylmethyl)-dibenz[b,e][1,4]oxazin-4-yl]-acetic acid in 40 ml of dioxan and 40 ml of concentrated hydrochloric acid was heated to 100° in a bomb tube for 2 hours, then cooled and evaporated to dryness. The residue was dried overnight in a high vacuum and then dissolved in 30 ml of dioxan/water (2:1). The solution was cooled to 0° and treated dropwise with 1N sodium hydroxide solution until the pH had reached ~8. The mixture was treated portionwise with 742 mg (3.4 mmol) of di-tert-butyidicarbonate and stirred at room temperature for 1 hour. The reaction mixture was poured into ice-water and methylene chloride and made slightly acidic with 1M hydrochloric acid solution. The organic phase was separated, dried over magnesium sulphate and evaporated. The residue was chromatographed on 150 g of silica gel with chloroform/methanol (9:1), whereupon, after recrystallization from chloroform/acetonitrile, 1.16 g (87.6%) of 3,7-diethoxy-10-ethyl-6-[((1-tert-butoxyformamido)methyl)-10H-dibenz[b,e][1,4]oxazin-4-yl]-acetic acid were obtained as a beige solid of m.p. >230° (dec.).

EXAMPLE 3.1.3

A solution of 173 mg (1.1 eq.) of N,N-dicyclohexylcarbodiimide in 1 ml of methylene chloride was slowly added dropwise to an ice-cooled solution of 370 mg (0.76 mmol) of 3,7-diethoxy-10-ethyl-6-[((1 -tert-butoxyformamido)methyl)-10H-dibenz[b,e][1,4]oxazin-4-yl]-acetic acid, 100 mg of benzyl alcohol and 20 mg of N,N-dimethylaminopyridine in 2 ml of methylene chloride. The reaction mixture was stirred at 0° for 1 hour, then brought slowly to room temperature and stirred for a further 3 hours. The precipitated solid was filtered off and washed with methylene chloride. The organic filtrates were washed with 5 ml of saturated sodium hydrogen carbonate solution and 5 ml of 1N aqueous hydrochloric acid, dried over magnesium sulphate and concentrated. The residue was chromatographed on silica gel with ethyl acetate/hexane (1:1), whereupon, after recrystallization from ethyl acetate/hexane, 230 mg (52.5%) of benzyl [3,7-diethoxy-10-ethyl-6-[((1-tert-butoxyformamido)methyl)-10H-dibenz[b,e][1,4] oxazin-4-yl]acetate were obtained as a light yellowish solid of m.p. 124°–126°.

EXAMPLE 3.2.1 a) 15.83 g of 1-benzotriazol-1-yl-N,N,N',N'-tetramethyluronium hexafluorophosphate and 9 ml of N-methylmorpholine were added to a solution of 13.65 g of Z-Asp(OBut)-OH.H$_2$O and 15.9 g of Val-OBzl.TosOH in 250 ml of DMF. After stirring for 2 hours the reaction mixture was evaporated in a vacuum and the residue was partitioned between ethyl acetate and water. The organic phase was washed with 5% KHSO$_4$/10% K$_2$SO$_4$ solution, water, saturated NaHCO$_3$ solution, water and saturated NaCl solution, dried over Na$_2$SO$_4$, filtered and evaporated. The residue was crystallized from diethyl ether/hexane and there were obtained 17.5 g of Z-Asp(OBut)-Val-OBzl of m.p. 99°; $[a]_D^{20}$ −27.7° (c=1, MeOH).

b) A solution of 10.25 g of Z-Asp(OBut)-Val-OBzl in 150 ml methanol was hydrogenated in the presence of 10% Pd-C. The catalyst was filtered off and the filtrate was evaporated. The residue was taken up in 30 ml of DMF, whereupon 6.12 g of Z-Gly-OSu were added and the pH was adjusted to 8.5 with N-methylmorpholine. The reaction mixture was stirred at 20° for 18 hours and worked up analogously to that described in paragraph a). The oil obtained was dissolved in methanol/water and hydrogenated over 10% Pd-C, whereupon the catalyst was filtered off. The filtrate was evaporated and the residue was crystallized from methanol/dimethyl ether, whereby. 5.52 g of Gly-Asp (OBut)-Val were obtained; MS 346 MH$^+$.

c) The pH of a suspension of 3 g of Gly-Asp(OBut)-Val and 5.86 g of Z$_3$-Arg-OSu in 50 ml of DMF was adjusted to 8.5 with N-methylmorpholine. The mixture was stirred at 20° for 20 hours and then poured into dil. KHSO$_4$/K$_2$SO$_4$ solution. The precipitated product was filtered off and recrystallized from ethyl acetate, whereby 5.3 g of Z$_3$-Arg-Gly-Asp(OBut)-Val-OH were obtained; MS: 904 MH$^+$.

d) A solution of 130 mg of benzyl [3,7-diethoxy-10-ethyl-6-[((1-tert-butoxyformamido)methyl)-10H-dibenz[b,e][1,4] oxazin-4-yl]acetate in 3 ml of trifluoroacetic acid was left to stand at 20° for 15 minutes and then concentrated in a vacuum. The residue was dissolved in 3 ml of DMF, whereupon the pH was adjusted to 8.5 with diisopropylethylamine and 207.9 mg of Z$_3$-Arg-Gly-Asp(OBut)-Val-OH, 34 mg of 1-hydroxybenzotriazole.H$_2$O and 74.3 mg of O-(1,2-dihydro-2-oxo-1-pyridyl)-N,N,N',N'-tetramethyluronium tetrafluoroborate were added at 0°. The pH was adjusted to 8.5 with diisopropylethylamine, whereupon the reaction mixture was stirred at 20° for 2 hours and subsequently added dropwise to dil. NaHCO$_3$ solution. The precipitated solid was filtered off under suction and crystallized from ethanol, whereby 207 mg of benzyl [6-((N$^\alpha$N$^G$N$^E$-tribenzyloxycarbonyl)-L-arginyl-glycyl-4-O-tert-butyl-L-aspartyl-L-valyl)aminomethyl)-3,7-diethoxy-10-ethyl-10H-dibenz[b,e][1,4]oxazin-4-yl]acetate were obtained; MS: 1362.5 MH$^+$.

e) 190.5 mg of the product obtained were dissolved in 25 ml of trifluoroethanol and hydrogenated in the presence of 10% Pd-C. The catalyst was filtered off and the filtrate was concentrated in a vacuum. The residue was dissolved in 20 ml of DMF and treated with 18.9 mg of 1-hydroxybenzotriazole .H$_2$O. The solution obtained was added dropwise while stirring over 20 minutes to a solution of 208 mg of O-(1,2-dihydro-2-oxo-1-pyridyl)-N,N,N',N',-tetramethyluronium tetrafluoroborate and 0.12 ml of diisopropylethylamine in 50 ml of DMF, whereupon the reaction mixture was stirred at 20° for 1 hour and then added dropwise to dil. NaHCO$_3$ solution. The precipitated solid was filtered off, washed with water and dissolved in 10 ml of trifluoroacetic. acid. After 1 hour the solution was evaporated in a vacuum and the residue was lyophilized from acetic acid. The lyophilizate was purified by HPLC. as described in Example 2.2.1. and isolated as the lyophilizate, whereby 99 mg of 4,6-cyclo-[acetyl-L-arginyl-glycyl-L-aspartyl-L-valyl-aminomethyl]-3,7-diethoxy-10-ethyl-10H-dibenz[b,e][1,4]oxazine trifluoroacetate(4,6-cyclo-[acetyl-SEQ ID NO:2-aminomethyl]-3,7-diethoxy-10-ethyl-10H-dibenz[b,e][1,4]oxazine trifluoroacetate) were obtained; MS 796 MH$^+$.

EXAMPLE 4.1.1.a

A mixture of 40.0 g (0.174 mol) of 4,4'-dimethoxy-diphenylamine and 11.0 g (0.341 mol) of sulphur was finely powdered and treated with 0.2 g (0.78 mmol) of iodine in a flask equipped with a mechanical stirrer. The solid residue was heated to 185° while stirring and the resulting melt was stirred for 1 hour, heated to 195° for 5 minutes after completion of the evolution of gas and then cooled. The solidified melt was taken up in 600 ml of acetonitrile on a steam bath. Then, the mixture was filtered while hot, whereupon the filtrate was left to stand at 0° until crystallization was complete. The precipitate was filtered off and dried, whereby 35.2g (78%) of 3,7-dimethoxy-phenothiazine were obtained as light brownish crystals of m.p. 193°–194°.

EXAMPLE 4.1.1.b

A suspension of 21.75 g (83.9 mmol) of 3,7-dimethoxy-phenothiazine, 43.36 g (0.34 mmol) of dried, powdered potassium carbonate, 25.22 g (0.20 mol) of dimethyl sulphate and 1.35 g (4.19 mmol) of tris-[2-(2-ethoxyethoxy) ethyl]amine in 300 ml of toluene was stirred at 110° for 1 hour, then cooled and poured into 11 of ice-water. The mixture was acidified slightly with 2N hydrochloric acid solution and extracted with ethyl acetate. The combined organic phases were extracted with saturated sodium chloride solution, dried over magnesium sulphate and evaporated. The residue was crystallized from ethanol/acetone, whereupon, after drying, 18.4 g (80.2%) of 3,7-dimethoxy-10-methylphehothiazine were obtained as a white solid of m.p. 166°–167°.

EXAMPLE 4.1.1.c 16.25 ml of n-butyllithium solution (1.6M in hexane) were added dropwise at −78° under argon to a solution of 5.46 g (10.0 mmol) of 3,7-dimethoxy-10-methylphenothiazine in 100 ml of diethyl ether/ tetrahydrofuran (4:1). The reaction mixture was stirred at −70° for 15 minutes, brought slowly to 0°, stirred for 2 hours and then treated at 0° with 3.39 g (30.0 mmol) of N-formylpiperidine. After stirring at 0° for 2 hours the mixture was poured into 500 ml of ice-water, whereupon it was acidified slightly with 0.5N hydrochloric acid solution and extracted with ethyl acetate. The combined organic phases were extracted with saturated sodium chloride solution, dried over magnesium sulphate and evaporated. The residue was crystallized from acetone, whereupon, after drying, 5.42 g (90%) of 3,7-dimethoxy-10-methyl-phenothiazine-4-carbaldehyde were obtained as a red solid of m.p. 150°.

EXAMPLE 4.1.1.da 20.0 ml of lithium borohydride solution (1M in tetrahydrofuran) were slowly added dropwise under argon and while cooling with ice to a solution of 5.42 g (18.0 mmol) of 3,7-dimethoxy-10-methyl-phenothiazine-4-carbaldehyde in 90 ml of tetrahydrofuran. The reaction mixture was stirred at 0° for 15 minutes, brought slowly to room temperature, stirred for 1 hour and then poured into ice-water. The mixture was acidified to pH 4 with 0.5N HCl and extracted three times with ethyl acetate. The combined organic phases were washed with saturated sodium chloride solution, dried over magnesium sulphate and evaporated. The residue was dried in a high vacuum.

The resulting crude 3,7-dimethoxy-10-methyl-phenothiazine-4-methanol was dissolved in 100 ml N,N-dimethylformamide and the solution was treated while cooling with ice with 2.45 g (36.0 mmol) of imidazole and a solution of 3.26 g (21.6 mmol) of tert.-butyidimethylchlorosilane in 10 ml of N,N-dimethylformamide. The reaction mixture was brought to room temperature, stirred for 4 hours and poured into ice-water, whereupon the mixture was extracted three times with ethyl acetate. The combined organic phases were extracted with water and saturated sodium chloride solution, dried over magnesium sulphate and evaporated. The residue was dried in a high vacuum. After recrystallization from hexane 5.0 g (66.2%) of 4-(tert.-butyl-dimethyl-silanyloxymethyl)-3,7-dimethoxy-10-methyl-phenothiazine were obtained as reddish crystals of m.p. 110°–111°.

EXAMPLE 4.1.1.db

A solution of 1.90 g (6.32 mmol) of 3,7-dimethoxy-10-methyl-phenothiazine-4-carbaldehyde in 30 ml of tetrahydrofuran was reduced with 7.6 ml of lithium borohydride solution (1M in tetrahydrofuran) analogously to that described in Example 4.1.1.da. The resulting 3,7-dimethoxy-10-methyl-phenothiazine-4-methanol was dissolved in 20 ml of tetrahydrofuran, whereupon 4.36 ml of n-butyllithium solution (1.6M in hexane) were added at −78°. The reaction mixture was brought slowly to 0°, then treated with 1.02 g (8.19 mmol) of 2-methoxy-ethoxymethyl chloride, stirred at room temperature for 2 hours and finally poured into ice-water/saturated sodium hydrogen carbonate solution. After three-fold extraction with diethyl ether the combined organic phases were washed with sodium chloride solution, dried over magnesium sulphate and evaporated. The residue was chromatographed on silica gel with diethyl ether/hexane (3:2), whereupon 2.09 g (84.6%) of 3,7-dimethoxy-4-(2-methoxy-ethoxymethoxymethyl)-10-methyl-phenothiazine were obtained as a colourless oil.

MS: 391 (M$^+$, 100), 376 (40), 288 (12), 272 (17), 256 (13), 242 (13), 128 (10).

EXAMPLE 4.1.1.ea

A solution of 4.56 g (10.9 mmol) of 4-(tert.-butyl-dimethyl-silanyloxymethyl)-3,7-dimethoxy-10-methyl-phenothiazine in 50 ml of diethyl ether/tetrahydrofuran (4:1) was reacted with 7.5 ml of n-butyllithium solution (1.6M in hexane) and 1.89 g (16.84 mmol) of N-formylpiperidine analogously to that described in Example 4.1.1c. The resulting 3,7-dimethoxy-4-(tert.butyldimethyl-silanyloxymethyl)-10-methyl-phenothiazine-4-carbaldehyde was dissolved in 50 ml of tetrahydrofuran and reduced with 12.0 ml of lithium borohydride solution (1M in tetrahydrofuran) analogously to that described in Example 4.1.8.b. The reaction mixture was poured into ice/1M sodium dihydrogen phosphate solution, whereupon the mixture was extracted three times with ethyl acetate. The combined organic phases were washed with saturated sodium chloride solution, dried over magnesium sulphate and concentrated. The residue was chromatographed on silica gel with ethyl acetate/hexane (1:1), whereupon, after recrystallization from ethyl acetate/hexane and drying, 3.30 g (67.6%) of [6-(tert.-butyl-dimethyl-silanyloxymethyl)-3,7-dimethoxy-10-methyl-phenothiazine-4-yl]methanol were obtained as a white solid of m.p. 46°–47°.

EXAMPLE 4.1.1.ea

A solution of 8.31 g (21.73 mmol) of 3,7-dimethoxy-4-(2-methoxy-ethoxymethoxymethyl)-10-methyl-phenothiazine in 100 ml of diethyl ether/tetrahydrofuran (4:1) was reacted with 17.6 ml of n-butyllithium solution (1.6M in hexane) and 3.68 g (32.6 mmol) of N-formylpiperidine analogously to that described in Example 4.1.1.c. The resulting 3,7-dimethoxy-6-(2-methoxy-ethoxymethoxymethyl)-10-methyl-phenothiazine-4-carbaldehyde was dissolved in 100 ml of tetrahydrofuran and reduced with 22 ml of lithium borohydride solution (1M in tetrahydrofuran) analogously to that described in Example 4.1.8.b. The crude product was chromatographed on silica gel with ethyl acetate/hexane (1:1), whereupon, after drying in a high vacuum, 6.44 g (70.3%) of [3,7-dimethoxy-6-(2-methoxy-ethoxymethoxymethyl)-10-methyl-phenothiazin-4-yl]-methanol were obtained as light yellowish oil.

MS: 421 (M$^+$, 100), 406 (24), 316 (10).

EXAMPLE 4.1.1.fa

A solution of 1.44 g (3.21 mmol) of [6-(tert.-butyl-dimethyl-silanyloxymethyl)-3,7-dimethoxy-10-methyl-phenothiazin-4-yl]-methanol, 0.70 g (4.75 mmol) of phthalimide and 0.92 g (3.5 mmol) of triphenylphosphine in 15 ml of tetrahydrofuran was reacted with a solution of 0.67 g (3.84 mmol) of dimethyl azodicarboxylate in 3 ml of tetrahydrofuran analogously to that described in Example 4.1.1.fb. Working up and chromatography was also effected analogously to that described in Example 4.1.1.fb. After recrystallization from ethanol/toluene 0.60 g (32.3%) of 2-[6-(tert.-butyl-dimethyl-silanyl-oxymethyl)-3,7-dimethoxy-10-methyl-phenothiazin-4-ylmethyl]-2,3-dihydro-1H-isoindole-1,3-dione was obtained as a white solid.

MS: 576 (M$^+$, 100), 561 (12), 505 (19), 504 (57), 489 (19), 444 (9), 298 (14), 160 (9), 75 (13).

EXAMPLE 4.1.1.fb

A solution of 3.19 g (18.32 mmol) of dimethyl azodicarboxylate in 10 ml of tetrahydrofuran was added within 4 hours under argon and while cooling with ice to a solution of 6.44 g (15.24 mmol) of [3,7-dimethoxy-6-(2-methoxy-ethoxymethoxymethyl)-10-methyl-phenothiazin-4-yl]-methanol, 2.68 g (18.11 mmol) of phthalimide and 4.40 g (16.77 mmol) of triphenylphosphine in 75 ml of tetrahydrofuran. The reaction mixture was stirred at 0° for a further 2 hours, brought slowly to room temperature and then poured into ice-water and ethyl acetate. The mixture was treated with hexane and ethanol, whereupon it was shaken vigorously. The organic phase was separated, washed with saturated sodium hydrogen carbonate solution and saturated sodium chloride solution, dried over magnesium sulphate and evaporated, and the residue was chromatographed on silica gel with ethyl acetate/hexane (1:1). After recrystallization from methanol 6.83 g (81.2%) of 2-[3,7-dimethoxy-6-(2-methoxy-ethoxymethoxymethyl)-10-methyl-phenothiazin-4-ylmethyl]-2,3-dihydro-1H-isoindole-1,3-dione were obtained as a white solid of m.p. 135°–137°.

EXAMPLE 4.1.1.ga

Analogously to that described in Example 4.1.8.f, a solution of 500 mg (0.77 mmol) of 2-[6-(tert.-butyl-dimethyl-silanyloxymethyl)-3,7-dimethoxy-10-methyl-phenothiazin-4-ylmethyl]-2,3-dihydro-1H-isoindole-1,3-dione in methylene chloride was reacted with boron tribromide solution (1M in methylene chloride) and the product obtained was reacted with sodium cyanide in N,N-dimethylformamide, whereupon 317 mg (92%) of [6-(1,3-dioxo-2,3-dihydro-1H-isoindol-2-ylmethyl)-3,7-dimethoxy-10-methyl-phenothiazin-4-yl]-acetonitrile were obtained as a yellow solid; m.p. 159°–160°.

EXAMPLE 4.1.1.gb 12.5 ml of hydrobromic acid (33 percent in glacial acetic acid) were slowly added dropwise under argon and while cooling with ice to a solution of 6.81 g (12.36 mmol) of 2-[3,7-dimethoxy-6-(2-methoxy-ethoxymethoxymethyl)-10-methyl-phenothiazin-4-ylmethyl]-2,3-dihydro-1H-isoindol-1,3-dione in 80 ml of methylene chloride. The reaction mixture was brought slowly to room temperature, stirred for 1 hour, treated with 6 ml of hydrobromic acid (33 percent in glacial acetic acid), stirred for a further 1 hour and poured into 300 ml of ice-cold saturated sodium bicarbonate solution. The mixture was extracted three times with methylene chloride. The combined organic phases were washed with saturated sodium chloride solution, dried over magnesium sulphate and concentrated. The residue was dried in a high vacuum for 1 hour and then dissolved in 80 ml of N,N-dimethylformamide, whereupon 5.8 g (120 mmol) of sodium cyanide were added. The reaction mixture was stirred at 60° for 30 minutes, cooled and poured into 350 ml of ice-water. The precipitated product was filtered off, washed with water, dried over phosphorus pentoxide and recrystallized from methanol/acetone. After drying 4.92 g (84.5%) of [6-(1,3-dioxo-2,3-dihydro-1H-isoindol-2-ylmethyl)-3,7-dimethoxy-10-methyl-phenothiazin-4-yl]-acetonitrile were obtained as a yellow solid of m.p. 159°–160°.

EXAMPLE 4.1.1.h 8.0 ml of hydrazine hydrate solution (1M in ethanol) were added at room temperature to a solution of 1.0 g (2.12 mmol) of [6-(1,3-dioxo-2,3-dihydro-1H-isoindol-2-ylmethyl)-3,7-dimethoxy-10-methyl-phenothiazin-4-yl]-acetonitrile in 10 ml of dioxan. The reaction mixture was stirred at 80° for 3 hours, cooled, treated with 200 ml of 10% sodium carbonate solution and stirred well. The mixture was extracted three times with methylene chloride and the combined organic phases were dried over magnesium sulphate and concentrated. The residue was dried in a high vacuum and dissolved in 30 ml of dioxan, whereupon 30 ml of concentrated hydrochloric acid were added. The reaction mixture was heated to 100° in a bomb tube for 2 hours, cooled and evaporated to dryness, whereupon the residue was dried in a high vacuum and dissolved in 10 ml of dioxan/water (2:1). The solution was brought to pH 8 by the dropwise addition of 1N aqueous sodium hydroxide solution, treated with a solution of 600 mg (2.74 mmol) of di-tert.-butyldicarbonate in 5 ml of dioxan while cooling with ice, stirred at room temperature for 1 hour and then poured into ice-water. The mixture was acidified slightly with 0.5N hydrochloric acid and extracted three times with methylene chloride. The combined organic phases were washed with sodium chloride solution, dried over magnesium sulphate and concentrated. The residue was chromatographed on silica gel with methanol/chloroform (9:1), whereupon, after drying, 580 mg (59.5%) of (6-tert.-butoxycarbonyl-aminomethyl-3,7-dimethoxy-10-methyl-phenothiazin-4-yl)-acetic acid were obtained as an amorphous solid.

MS: 460 ($M^+$, 65), 404 (36), 386 (100), 341 (68), 360 (17), 284 (32), 269 (12), 256 (20), 149 (12), 59 (42), 57 (30), 41 (50).

EXAMPLE 4.1.2

A solution of 510 mg (1.081 mmol) of [6-(1,3-dioxo-2,3-dihydro-1H-isoindol-2-ylmethyl)-3,7-dimethoxy-10-methyl-phenothiazin-4-yl]-acetonitrile in 20 ml of dioxan and 20 ml of fuming hydrochloric acid was heated to 100° in a bomb tube for 1 hour. The reaction mixture was cooled and poured into 250 ml of ice-water. The solid was filtered off, washed with water and dried over phosphorus pentoxide, whereby 400 mg (75.4%) of [6-(1,3-dioxo-2,3-dihydro-1H-isoindol-2-ylmethyl)-3,7-dimethoxy-10-methyl-phenothiazin-4-yl]-acetic acid were obtained as beige solid.

IR (KBr): 3357w (br.), 3092w, 2938w, 2834w, 1772w, 1715s, 1584w, 1463s, 1436m, 1391s, 1346m, 1259s, 1181w, 1048m, 801w, 719m.

EXAMPLE 4.1.3

A solution of 158 mg (0.77 mmol) of N,N-dicyclohexylcarbodiimide in methylene chloride was added dropwise to an ice-cooled solution of 3.20 mg (0.695 mmol) of (6-tert.-butoxycarbonyl-aminomethyl-3,7-dimethoxy-10-methyl-phenothiazin-4-yl)-acetic acid, 90.2 mg (0.84 mmol) of benzyl alcohol and 20 mg of N,N-dimethylaminopyridine in 2.5 ml of methylene chloride. The reaction mixture was stirred at room temperature overnight and filtered. The filter residue was washed with methylene chloride. The combined filtrates were washed with saturated sodium bicarbonate solution, dried over magnesium sulphate and concentrated. The residue was chromatographed on silica gel with ethyl acetate/hexane (1:4), whereupon, after recrystallization from ethanol and drying, 280 mg (73.3%) of benzyl (6-tert.-butoxycarbonyl-aminomethyl-3,7-dimethoxy-10-methyl-phenothiazin-4-yl)-acetate were obtained as white crystals of m.p. 131°–132°.

EXAMPLE 4.1.4

4 ml of trifluoroacetic acid were added while cooling with ice to a solution of 275 mg (0.5 mmol) of benzyl (6-tert.-butoxycarbonyl-aminomethyl-3,7-dimethoxy-10-methyl-phenothiazin-4-yl)-acetate in 1.5 ml of methylene chloride. The reaction mixture was stirred at 0° for 30 minutes and then evaporated to dryness, the residue was suspended in diethyl ether/hexane, the suspension was filtered and the filter residue was dried in a high vacuum, whereupon 260 mg (92%) of benzyl (6-aminomethyl-3,7-dimethoxy-10-methyl-phenothiazin-4-yl)-acetate trifluoroacetate (1:1) were obtained as a white solid of m.p. 196°.

MS: 450 ($M^+$-$CF_3COOH$, 100) 435 (50), 91 (24).

EXAMPLE 4.1.5.a

A suspension of 15.0 g (57.8 mmol) of 3,7-dimethoxy-phenothiazine, 31.9 g (0.231 mmol) of powdered potassium carbonate, 61.29 g (0.289 mol) of 1-iodohexane and 1.6 g (5.0 mmol) of tris-[2-(2-methoxymethoxy)ethyl]amine was heated to 110° for 64 hours. The working up was effected analogously to that described in Example 4.1.1.b. After chromatography on silica gel with ethyl acetate/hexane (1:4) 18.33 g (91.8%) of 10-hexyl-3,7-dimethoxy-phenothiazine were obtained as a brownish oil.

MS: 371 ($M^+$, 39), 300 (11), 286 (100), 243 (7).

EXAMPLE 4.1.5.b

A solution of 3.42 g (10.0 mmol) of 10-hexyl-3,7-dimethoxy-phenothiazine in 50 ml of diethyl ether/tetrahydrofuran (4:1) was reacted with 8.12 ml of n-butyllithium solution (1.6M in hexane) and 3.35 g (29.6 mmol) of N-formylpiperidine analogously to that described in Example 4.1.1.c. The product was chromatographed on silica gel with ethyl acetate/hexane (1:4), whereupon 2.39 g (64.4%) of 10-hexyl-3,7-dimethoxy-phenothiazine-4-carbaldehyde were obtained as a red oil.

MS: 371 ($M^+$, 39), 300 (11), 286 (100), 243 (7).

EXAMPLE 4.1.5.c

A solution of 2.39 g (6.43 mmol) of 10-hexyl-3,7-dimethoxy-phenothiazine-4-carbaldehyde in 30 ml of tetrahydrofuran was reduced with 7.0 ml of lithium borohydride solution (1M in tetrahydrofuran) analogously to that described in Example 4.1.1.da. The resulting 10-hexyl-3,7-dimethoxy-phenothiazine-4-methanol was reacted with 4.0 ml of n-butyllithium solution (1.6M in hexane) and 1.0 g (8.0 mmol) of 2-methoxyethoxymethyl chloride analogously to that described in Example 4.1.1.db. After chromatography on silica gel with diethyl ether/hexane (3:2) 2.33 g (78.5%) of 10-hexyl-3,7-dimethoxy-4-(2-methoxy-ethoxymethoxymethyl)-phenothiazine were obtained as a light yellowish oil.

MS: 461 ($M^+$, 83) 376 (100), 356 (16), 256 (23), 242 (27), 241 (13), 228 (9), 59 (15), 45 (17), 43 (26).

EXAMPLE 4.1.5.d

A solution of 8.0 g (17.33 mmol) of 10-hexyl-3,7-dimethoxy-4-(2-methoxy-ethoxymethoxymethyl)-phenothiazine in 100 ml of diethyl ether/tetrahydrofuran (4:1) was reacted with 12.0 ml of n-butyllithium solution (1.6M in hexane) and 2.94 g (26.0 mmol) of N-formylpiperidine analogously to that described in Example 4.1.1.c. The resulting 3,7-dimethoxy-10-hexyl-6-(2-methoxyethoxymethoxymethyl)phenothiazine-4-carbaldehyde was dissolved in 100 ml of tetrahydrofuran and reduced with 22 ml of lithium borohydride solution (1M in tetrahydrofuran) analogously to that described in Example 4.1.8.b. The product was chromatographed on silica gel with ethyl acetate/hexane (1:1), whereupon, after drying in a high vacuum, 4.41 g (51.7%) of [10-hexyl-3,7-dimethoxy-6-(2-methoxyethoxymethoxymethyl)-phenothiazin-4-yl]-methanol were obtained as a light yellowish oil.

MS: 491 ($M^+$, 100), 407 (24), 406 (90), 386 (9).

EXAMPLE 4.1.5.e

A solution of 11.38 g (24.65 mmol) of [10-hexyl-3,7-dimethoxy-6-(2-methoxy-ethoxymethoxymethyl)-phenothiazin-4-yl]-methanol, 5.44 g (37.0 mmol) of phthalimide and 7.11 g (27.1 mmol) of triphenylphosphine in 100 ml of tetrahydrofuran was reacted with a solution of 5.15 g (29.6 mmol) of dimethyl azodicarboxylate in 15 ml of tetrahydrofuran analogously to that described in Example 4.1.1.fb. Working up and chromatography were likewise effected analogously to that described in Example 4.1.1.fb. After recrystallization from ethanol 14.13 g (92.3%) of 2-[10-hexyl-3,7-dimethoxy-6-(2-methoxyethoxymethoxymethyl)-phenothiazin-4-ylmethyl]-2,3-dihydro-1H-isoindole-1,3-dione were obtained as white solid of m.p. 86°–87°.

EXAMPLE 4.1.5.f

Analogously to that described in Example 4.1.1.gb, a solution of 13.32 g (21.24 mmol) of 2-[10-hexyl-3,7-dimethoxy-6-(2-methoxyethoxymethoxymethyl)-phenothiazin-4-ylmethyl]-2,3-dihydro-1H-isoindole-1,3-dione in 70 ml of methylene chloride was treated with a total of 30 ml of hydrobromic acid (33 percent in glacial acetic acid) and the product was reacted with 10.4 g (0.212 mol) of sodium cyanide in 70 ml of N,N-dimethylformamide. After recrystallization from ethanol/tert.-butyl methyl ether 9.45 g (81.3%) of [6-(1,3-dioxo-2,3-dihydro-1H-isoindol-2-ylmethyl)-10-hexyl-3,7-dimethoxy-phenothiazin-4-yl]-acetonitrile were obtained as a yellow solid of m.p. 186°–187°.

EXAMPLE 4.1.5.g

Analogously to that described in Example 4.1.1.h, starting from a solution of 2.16 g (4.0 mmol) of [6-(1,3-dioxo-2,3-dihydro-1H-isoindol-2-ylmethyl)-10-hexyl-3,7-dimethoxy-phenothiazin-4-yl]-acetonitrile in 20 ml of dioxan using 8.0 ml of hydrazine hydrate solution (1M in ethanol), 40 ml of concentrated hydrochloric acid and a solution of 1.09 g (5.0 mmol) of di-tert.-butyl dicarbonate in dioxan, 1.25 g (58.9%) of (6-tert.-butoxycarbonyl-aminomethyl-10-hexyl-3,7-dimethoxy-phenothiazin-4-yl)-acetic acid were obtained as an amorphous solid.
MS: 531 ($M^+$+1, 38), 530 ($M^+$, 100), 475 (10), 474 (10), 429 (15), 414 (55), 389 (75), 345 (12).

EXAMPLE 4.1.6

A solution of 610 mg (1.15 mmol) of (6-tert.-butoxycarbonyl-aminomethyl-10-hexyl-3,7-dimethoxy-phenothiazin-4-yl)-acetic acid, 150 mg (1.38 mmol) of benzyl alcohol and 30 mg of N,N-dimethylaminopyridine in 5 ml of methylene chloride was reacted with a solution of 261 mg (1.26 mmol) of N,N-dicyclohexylcarbodiimide in methylene chloride analogously to that described in Example 4.1.3. Working up and chromatography were effected analogously to that described in Example 4.1.3. After recrystallization from ethanol and drying 370 mg (51.8%) of benzyl (6-tert.-butoxycarbonyl-aminomethyl-10-hexyl-3,7-dimethoxy-phenothiazin-4-yl)-acetate were obtained as a white solid.
MS: (FAB): 620 ($M^+$, 100), 564 (16), 521 (12), 479 (22).

EXAMPLE 4.1.7

Benzyl (6-tert.-butoxycarbonyl-aminomethyl-10-hexyl-3,7-dimethoxy-phenothiazin-4-yl)-acetate was converted into benzyl (6-aminomethyl-3,7-dimethoxy-10-hexyl-phenothiazin-4-yl)-acetate trifluoroacetate (1:1) analogously to that described in Example 4.1.4

EXAMPLE 4.1.8.a

A suspension of 10.0 g (38.56 mmol) of 3,7-dimethoxy-phenothiazine, 21.3 g (0.154 mol) of powdered potassium carbonate, 33.0 g (0.193 mol) of benzyl bromide and 1.3 g (4.0 mmol) of tris-[2-(2-methoxyethoxy)ethyl]-amine was heated to 110° for 2 hours. The working up was effected analogously to that described in Example 4.1.1b. After chromatography on silica gel with ethyl acetate/hexane (1:4) and recrystallization from ethanol/water (9:1) 12.06 g (89.5%) of 10-benzyl-3,7-dimethoxy-phenothiazine were obtained as white crystals of m.p. 110°.

EXAMPLE 4.1.8.b

A solution of 10.0 g (28.6 mmol) of 1-benzyl-3,7-dimethoxy-phenothiazine in 150 ml of diethyl ether/tetrahydrofuran (4:1) was reacted with 21.5 ml of n-butyllithium solution (1.6N in hexane) and 4.9 g (42.9 mmol) of N-formylpiperidine analogously to that described in Example 4.1.1.c.

The crude 10-benzyl-3,7-dimethoxy-phenothiazine-4-carbaldehyde obtained was dissolved in 150 ml of absolute tetrahydrofuran, whereupon the solution was treated at 0° with 31.5 ml of lithium borohydride solution (1M in tetrahydrofuran). The reaction mixture was brought slowly to room temperature, stirred for 1 hour and then poured into ice-water, and the pH was adjusted to 3–4 with 0.5N hydrochloric acid solution. The mixture was extracted with ethyl acetate. The combined organic phases were washed with saturated sodium chloride solution, dried over magnesium sulphate and evaporated. After chromatography on silica gel with ethyl acetate/hexane (1:2) 8.0 g (73.7%) of (10-benzyl-3,7-dimethoxy-phenothiazin-4-yl)-methanol were obtained as a white amorphous solid.
MS: 379 ($M^+$, 8), 289 (19), 288 (100), 91 (27), 65 (11).

EXAMPLE 4.1.8.c

A solution of 21.9 g (57.7 mmol) of (10-benzyl-3,7-dimethoxy-phenothiazin-4-yl)-methanol and 8.57 g (0.126 mol) of imidazole in 300 ml of N,N-dimethylformamide was reacted with a solution of 10.47 g (69.4 mmol) of tert.-butyidimethylchlorosilane in 25 ml of N,N-dimethylformamide analogously to that described in Example 4.1.1.da. After recrystallization from hexane/tert.-butyl methyl ether 22.2 g (77.9%) of 10-benzyl-4-(tert.-butyl-dimethyl-silanyloxymethyl)-3,7-dimethoxy-phenothiazine were obtained as a white solid of m.p. 55°.

EXAMPLE 4.1.8.d

A solution of 4.93 g (10.0 mmol) of 10-benzyl-4-(tert.-butyl-dimethyl-silanyloxymethyl)-3,7-dimethoxy-phenothiazine in 50 ml of diethyl ether/tetrahydrofuran (4:1) was reacted with 7.5 ml of n-butyllithium solution (1.6M in hexane) and 1.47 g (13.0 mmol) of N-formylpiperidine analogously to that described in Example 4.1.1.c. The 10-benzyl-3,7-dimethoxy-6-(tert.-butyl-dimethyl-silanyloxymethyl)phenothiazine-4-carbaldehyde obtained was dissolved in 50 ml of tetrahydrofuran and reduced with 10.0 ml of lithium borohydride solution (1M in tetrahydrofuran) analogously to that described in Example 4.1.8.b. The reaction mixture was worked up and chromatographed analogously to that described in 4.1.1.ea. After drying in a high vacuum 3.72 g (71.9%) of 10-benzyl-6-(tert.-butyl-dimethyl-silanyloxymethyl)-3,7-dimethoxy-phenothiazin-4-yl-methanol were obtained as an amorphous white solid. MS:
523 ($M^+$, 8), 434 (14), 433 (33), 432 (100), 360 (11), 91 (22), 75 (7).

EXAMPLE 4.1.8.e

A solution of 3.19 g (6.09 mmol) of 10-benzyl-6-(tert.-butyl-dimethyl-silanyloxymethyl)-3,7-dimethoxyphenothiazin-4-yl-methanol, 1.34 g (9.10 mmol) of phthalimide and 1.75 g (6.67 mmol) of triphenylphosphine in 30 ml of tetrahydrofuran was reacted with a solution of 1.27 g (7.29 mmol) of dimethyl azodicarboxylate analogously to that described in Example 4.1.1.fb. Working up and chromatography were likewise effected analogously to that described in Example 4.1.1.fb. After recrystallization from ethanol 3.27 g (82.2%) of 2-[10-benzyl-6-(tert.-butyl-dimethyl-silanyloxymethyl)-3,7-dimethoxy-phenothiazin-4-ylmethyl]-2,3-dihydro-1H-isoindole-1,3-dione were obtained as a light yellowish solid.

MS: 652 (M$^+$, 8), 563 (26), 562 (56), 561 (100), 490 (18), 489 (10), 91 (16).

EXAMPLE 4.1.8.f 5.0 ml of boron tribromide solution (1M in methylene chloride) were slowly added dropwise while cooling with ice and under argon to a solution of 3.25g (4.97mmol) of 2-[10-benzyl-6-(tert.-butyl-dimethyl-silanyloxymethyl)-3,7-dimethoxy-phenothiazin-4-ylmethyl]-2,3-dihydro-1H-isoindole-1,3-dione in 25 ml of methylene chloride. The reaction mixture was stirred at 0° for 15 minutes and at room temperature for 2 hours. Working up and reaction of the product with 3.25 g (50.0 mmol) of sodium cyanide were effected analogously to that described in Example 4.1.1.gb. After crystallization from ethyl acetate 2.71 g (99%) of [10-benzyl-6-(1,3-dioxo-2,3-dihydro-1H-isoindol-2-ylmethyl)-3,7-dimethoxy-phenothiazin-4-yl]acetonitrile were obtained as a yellow solid of m.p. 230°.

EXAMPLE 4.1.8.g

A solution of 1.09 g (2.0 mmol) of [10-benzyl-6-(1,3-dioxo-2,3-dihydro-1H-isoindol-2-ylmethyl)-3,7-dimethoxy-phenothiazin-4-yl]acetonitrile in 10 ml of dioxan was reacted with 10.0 ml of hydrazine hydrate solution (1M in ethanol) analogously to that described in Example 4.1.1.h. The product obtained was dissolved in 20 ml of ethanol and treated with 20 ml of 6N aqueous sodium hydroxide solution, whereupon the mixture was stirred at 110° for 2 hours and then evaporated to dryness. The residue was neutralized with 2N aqueous hydrochloric acid and the solution was concentrated. The residue was dried in a high vacuum and subsequently reacted with 654 mg (3.0 mmol) of di-tert.butyl dicarbonate in dioxan analogously to that described in Example 4.1.1.h. Working up and chromatography were effected analogously to that described in Example 4.1.1.h. After drying 650 mg (60.5%) of (10-benzyl-6-tert.-butoxycarbonyl-aminomethyl-3,7-dimethoxy-phenothiazin-4-yl)-acetic acid were obtained as an amorphous solid.

MS: 536 (M$^+$, 5), 445 (27), 389 (42), 371 (33), 345 (71), 97 (29), 83 (34), 71 (45), 69 (65), 57 (82), 41 (100).

EXAMPLE 4.1.9

A suspension of 776 mg (1.44 mmol) of (10-benzyl-6-tert.-butoxycarbonyl-aminomethyl-3,7-dimethoxy-phenothiazin-4-yl)-acetic acid and 100 mg of palladium-on-charcoal in 10 ml of methanol was treated with 0.5 ml of acetic acid and hydrogenated over the weekend under 1.5 bar of hydrogen. The mixture was filtered, the filtrate was concentrated and the residue was dried in a high vacuum. After chromatography on silica gel with chloroform/methanol (9:1) and drying 585 mg (91%) of [6-(1-tert.-butoxycarbonyl-aminomethyl)-3,7-dimethoxyphenothiazin-4-yl]-acetic acid were obtained as light brownish amorphous foam. FAB (MS): 446 (M$^+$, 20).

To a solution of 585 mg (1.31 mmol) of the compound obtained in 10 ml of N,N-dimethylformamide were added dropwise while cooling with ice and under argon 0.34 g (1.97 mmol) of benzyl bromide and within 1 hour 0.50 ml (1.97 mmol) of diazabicycloundecane (DMU). The reaction mixture was stirred at 0° for 30 minutes, brought slowly to room temperature, stirred for a further 2 hours and poured into water, whereupon the mixture was extracted with ethyl acetate. The organic phase was extracted twice with water and with 0.5N aqueous hydrochloric acid, dried over magnesium sulphate and evaporated. The residue was chromatographed on silica gel with ethyl acetate/hexane (1:1), whereupon 532 mg (75%) of benzyl(6-tert.-butoxycarbonyl-aminomethyl-3,7-dimethoxy-phenothiazin-4-yl)-acetate were obtained as a beige solid. FAB (MS): 536 (M$^+$, 100), 480 (70), 390 (65).

EXAMPLE 4.1.10

A mixture of 360 mg (0.67 mmol) of benzyl (6-tert.-butoxycarbonyl-aminomethyl-3,7-dimethoxy-phenothiazin-4-yl)-acetate, 91.7 mg (0.80 mmol) of glutaric anhydride and 63.7 mg (0.80 mmol) of pyridine in 5 ml of toluene was treated with 10 mg of N,N-dimethylaminopyridine. The mixture was heated to 110° under argon for 48 hours and then poured into ice-water, whereupon the mixture was acidified with 1N hydrochloric acid and exhaustively extracted with methylene chloride. The organic phase was dried over magnesium sulphate and concentrated. The residue was chromatographed on silica gel with chloroform/methanol (9:1), whereupon 310 mg (71%) of 5-(4-benzyloxycarbonylmethyl-6-tert.-butoxycarbonyl-aminomethyl-3,7-dimethoxy-phenothiazin-10yl)-5-oxo-pentanoic acid were obtained as a white solid of m.p. 65°–68°.

MS (FAB): 651 (M$^+$+H, 20), 595 (20), 536 (20), 389 (25), 217 (80), 91 (100).

EXAMPLE 4.2.1

A solution of 364 mg (0.74 mmol) of [6-(1,3-dioxo-2,3-dihydro-1H-isoindol-2-ylmethyl)-3,7-dimethoxy-10-methyl-phenothiazin-4-yl]-acetic acid, 309 mg (0.815 mmol) of 1-benzotriazo-1-yl-N,N,N',N'-tetramethyluronium hexafluorophosphate (HBTU) and 253.2 mg (0.815 mmol) of Gly-Gly-Ala-Gly (SEQ ID NO:4) methyl ester hydrochloride in 3 ml of N,N-dimethylformamide was treated with 187.3 mg (1.85 mmol) of N-methylmorpholine while cooling with ice. The reaction mixture was stirred at room temperature for 30 minutes, then treated with water and finally filtered. The residue was washed with water, dried over phosphorus pentoxide and boiled briefly in methanol. The solid was filtered off and dried, whereupon 450 mg (81.5%) of [3,7-dimethoxy-10-methyl-6-(1,3-dioxo-2,3-dihydro-1H-isoindol-2-ylmethyl)-phenothiazin-4-yl]-acetyl-glycyl-glycyl-L-alanyl-glycine methyl ester were obtained as a light greenish solid. M.p. >210°. MS (FAB): 747 (M$^+$, 10), 367 (19), 318 (10), 223 (20), 185 (45), 156 (60), 119 (100).

EXAMPLE 4.2.2

1 ml of hydrazine hydrate was added to a solution of 390 mg (0.522 mmol) of the product of Example 4.2.1. in 10 ml of methanol. The reaction mixture was stirred at 50° for 6 hours, then cooled and filtered. The filter residue was washed with methanol, dried and dissolved in 5 ml of N,N-dimethylformamide. The solution was cooled to 0°, whereupon 1 ml of fuming hydrochloric acid was added dropwise and then 0.5 ml of 14 percent sodium nitrite solution was added. The mixture was stirred at −10° for 45 minutes and then treated dropwise with 1 ml of N-methylmorpholine. The reaction mixture was stirred for 1 hour and then evaporated to dryness. The residue was chromatographed on silica gel with chloroform/methanol (4:1), whereupon 75 mg (24.6%) of 3,7-dimethoxy-10-methyl-4,6-cyclo-[acetyl-glycyl-glycyl-L-alanyl-glycyl-aminomethyl]phenothiazine(3,7-dimethoxy-10-methyl-4,6-cyclo-[acetyl-SEQ ID NO:4-aminomethyl]phenothiazine) were obtained as a white solid. M.p. >260°. MS (FAB): 585 (M$^+$+H, 60), 318 (10), 253 (10), 200 (10), 136 (25), 110 (25), 87 (100).

EXAMPLE 4.3.1

25 mg of dried sodium hydrogen carbonate and then at 0° 238.2 mg (0.35 mmol) of tri-carbobenzoxy-arginine hydroxy-succinimide ester were added to a solution of 150 mg (0.265 mmol) of benzyl (6-aminomethyl-3,7-dimethoxy-10-methyl-phenothiazin-4-yl)-acetate trifluoroacetate (1:1) in 30 ml of acetonitrile. The reaction mixture was stirred at 0° for 30 minutes and at room temperature overnight and then poured into ice-water and methylene chloride, whereupon the organic phase was washed with sodium chloride solution, dried over magnesium sulphate and concentrated. The residue was dried in a high vacuum, taken up in 20 ml of 2,2,2-trifluoroethanol and hydrogenated with 150 mg of palladium-on-charcoal (10%) for 2 hours under normal pressure. The catalyst was filtered off and the filtrate was concentrated. The residue was precipitated from diethyl ether, filtered off, dried in a high vacuum and taken up in 5 ml of N,N-dimethylformamide. The mixture was treated with 136.4 mg (0.36 mmol) of 1-benzotriazol-1-yl-N,N,N',N'-tetra-methyluronium hexafluorophosphate (HBTU) and then at 0° with 91.0 mg (0.9 mmol) of N-methylmorpholine. The reaction mixture was stirred at room temperature overnight, whereupon the solvent was distilled off. The residue was suspended in water and chloroform, filtered off and dried in a high vacuum, whereupon 80 mg (50%) of (S)-4,12-dimethoxy-8-(3-guanidinopropyl)-17-methyl-1, 15-imino-6,7,8,9,10,11-hexahydro-5H-dibenzo[b,k][1,5,8] thiadiazacyclododecine-7,10-dione trifluoroacetate (1:1) were obtained as a grey solid.

MS (FAB): 499 (M$^+$(free base)$_+$H, 35), 431 (10), 239 (20), 217 (100), 131 (65), 126 (50), 109 (95).

EXAMPLE 4.3.2

From 112 mg of benzyl (6-aminomethyl-3,7-dimethoxy-10-methyl-phenothiazin-4-yl)-acetate trifluoroacetate and 270 mg Z-Arg(Pmc)-Gly-Asp(OBut)-Val-OH there were obtained, analogously to that described in Example 2.2.2., 24 mg of 3,7-dimethoxy-10-methyl-4,6-cyclo-[acetyl-L-arginyl-glycyl-L-aspartyl-L-valyl-aminomethyl] phenothiazine trifluoroacetate(3,7-dimethoxy-10-methyl-4, 6-cyclo-[acetyl-SEQ ID NO:2-aminomethyl]phenothiazine trifluoroacetate) (1:1). MS: 770 MH$^+$.

EXAMPLE 4.4.1

82.5 mg (0.82 mmol) of 4-methylmorpholine were added at 0° to a solution of 150 mg (0.33 mmol) of (6-tert.-butoxycarbonyl-aminomethyl-3,7-dimethytoxy-10-methyl-phenothiazin-4-yl)-acetic acid, 65.02 mg (0.36 mmol) of L-alanine tert.-butyl ester hydrochloride and 135.8 mg (0.36 mmol) of 1-benzotriazol-1-yl-N,N ,N',N'-tetramethyluronium hexafluorophosphate (HBTU) in 5 ml of N,N-dimethylformamide. The reaction mixture was brought slowly to room temperature, stirred for 1 hour and poured into ice-water. The separated precipitate was filtered off, washed with water, dried over phosphorus pentoxide and stirred at 0° for 1 hour in 5 ml of cold trifluoroacetic acid, whereupon the mixture was evaporated to dryness in a high vacuum. The amorphous residue was dried in a high vacuum and dissolved in 10 ml of N,N-dimethylformamide. The solution was added while cooling with ice to a suspension of 152 mg of sodium hydrogen carbonate (powdered and dried) and 142.8 mg (0.537 mmol) of diphenylphosphoryl azide (DPPA). The reaction mixture was stirred at 0° for 1 hour and then evaporated to dryness. The residue was taken up in water and chloroform, the organic phase was separated and the aqueous phase was extracted with chloroform. The combined organic phases were dried over magnesium sulphate and evaporated. The residue was crystallized from methanollhexafluoroisopropanol and dried, whereupon 110 mg (74.6%) of (S)-4,12-dimethoxy-8,17-dimethyl-1,15-imino-6,7,8,9,10,11-hexahydro-5H-dibenzo[b,k][1,5,8] thiadiazacyclododecine-7,10-dione were obtained as a white solid.

MS (FAB): 414 (M$^+$+H, 33), 413 (M$^+$, 20), 325 (33), 217 (100), 126 (75), 109 (90).

EXAMPLE 4.4.2 a) 184 mg of (6-tert.-butoxycarbonyl-aminomethyl-3,7-dimethoxy-10-methyl-phenothiazin-4-yl)-acetic acid in 3 ml of DMF were treated in succession with 236.7 mg of Gly-Gly-OBzl.ToSoH, 379 mg of HBTU and 0.34 ml of DIPEA. The reaction mixture was poured into dilute NaHCO$_3$ solution and the separated precipitate was filtered off, washed on the filter with KHSO$_4$/K$_2$SO$_4$ solution and water and dissolved in 10 ml of 1N HCl/acetic acid. Ether was added after 10 minutes, whereby a product separated and was removed and dissolved in 5 ml of DMF. The solution was treated with 175 mg of Boc-Gly-OH, 379 mg HBTU and 0.34 ml of DIPEA, whereupon the reaction mixture was poured into dilute NaHCO$_3$ solution. The separated precipitate was filtered off and crystallized from ethanol, whereby 195 mg of [6-((tert.-butoxycarbonylglycyl)aminomethyl)-3,7-dimethoxy-10-methyl-phenothiazin-4-yl]-acetyl-glycyl-glycine benzyl ester were obtained; MS: 722 MH$^+$.

b) The product obtained was dissolved in 10 ml of 1N HCl/acetic acid, whereupon ether was added after 10 minutes. The separated precipitate was filtered off and dissolved in 10 ml of DMF, whereupon the solution was treated with 210 mg of Z-Asp(OBut)-OSu and 0.17 ml of DIPEA. After stirring 18 hours the reaction solution was poured into dilute NaHCO$_3$ solution. The separated precipitate was filtered off, washed with KHSO$_4$/K$_2$SO$_4$ solution and water and dried in a vacuum, whereby 202 mg of [6-((N-benzyloxycarbonyl-O-tert.-butyl-L-aspartyl)-glycyl-aminomethyl)-3,7-dimethoxy-10-methyl-phenothiazin-4-yl]-acetyl-glycyl-glycine benzyl ester were obtained; MS: 927 MH$^+$.

c) 190 mg of this compound were hydrogenated and cyclized analogously to that described in Example 2.2.1. The protecting group was cleaved off from the cyclization product using 1N HCl/acetic acid and the product obtained was lyophilized from acetic acid, whereby 78 mg of 3,7-dimethoxy-10-methyl-4,6-cyclo-[acetyl-glycyl-L-aspartyl-glycyl-glycyl-aminomethyl]phenothiazine(3,7-dimethoxy-10-methyl-4,6-cyclo-[acetyl-SEQ ID NO:3-aminomethyl] phenothiazine) were obtained; MS: 629 MH$^+$.

EXAMPLE 4.5.1

A solution of 150 mg of (6-tert.-butoxycarbonyl-aminomethyl-10-hexyl-3,7-dimethoxy-phenothiazin-4-yl)- acetic acid in 5 ml of trifluoroacetic acid was left to stand at 20° for 1 hour and then evaporated in a vacuum. The residue was dissolved in 5 ml of DMF, whereupon the pH was adjusted to 8.5 with DIPEA and 269 mg of $Z_3$-Arg-OSu were added at 0°. The reaction mixture was stirred at 20° for 1 hour and then poured into $KHSO_4$/10% $K_2SO_4$ solution. The precipitated solid was filtered off and crystallized from ethanol. The crystals were dissolved in 20 ml of trifluoroethanol and hydrogenated in the presence of 10% Pd-C. The further processing was effected analogously to that described in Example 2.2.1. and 91 mg of (S)-8-(3-guanidinopropyl)-17-hexyl-4,12-dimethoxy-1,15-imino-6,7,8,9,10,11-hexahydro-5H-dibenzo[b,k][1,5,8]thiadiazacyclododecine-7,10-dione trifluoroacetate (1:1) were obtained. MS: 569 $MH^+$.

EXAMPLE 4.5.2 a) A solution of 700 mg (1.31 mmol) of (6-tert.-butoxycarbonyl-aminomethyl-10-hexyl-3,7-dimethoxy-phenothiazin-4-yl)-acetic acid, 547 mg (1.44 mmol) of 1-benzotriazol-1-yl-N,N,N',N'-tetramethylnonium hexafluorophosphate (HBTU) and 488.1 mg (1.44 mmol) of Gly-Gly-Ala-Gly (SEQ ID NO:4)methyl ester hydrochloride in 5 ml of DMF was processed analogously to that described in Example 4.8.3., whereupon, after chromatography on silica gel with chloroform/methanol (9:1), 800 mg (77.6%) of (6-tert.-butoxycarbonyl-aminomethyl-10-hexyl-3,7-dimethoxy-phenothiazin-4-yl)-acetyl-glycyl-glycyl-L-alanyl-glycine methyl ester were obtained as an amorphous foam.

MS (FAB): 786 ($M^+$, 85), 687 (100). IR (KBr): 3298m, 2932w, 1740w, 1700s, 1656s, 1634s, 1518s, 1462s, 1365m, 1256s, 1166m, 1049m.

b) A solution of 58.5 mg (0.074 mmol) of the above compound was treated with 2 ml of aqueous 2N sodium hydroxide solution and subsequently with 27.5 mg (0.1 mmol) of diphenylphosphoryl azide and 31 mg (0.37mmol) of sodium hydrogen carbonate in 5 ml of N,N-dimethylformamide analogously to that described in Example 4.8.3. The residue was purified by preparative high pressure liquid chromatography (RP 18, acetonitrile/water/0.04% trifluoroacetic acid), whereupon, after lyophilization, 20 mg (41.2%) of 10-hexyl-3,7-dimethoxy-4,6-cyclo-[acetyl-glycyl-glycyl-L-alanyl-glycyl-aminomethyl]phenothiazine(10-hexyl-3,7-dimethoxy-4,6-cyclo-[acetyl-SEQ ID NO:4-aminomethyl]phenothiazine) were obtained as an amorphous foam.

MS (FAB): 655 ($M^+$+H, 100), 654 ($M^+$, 69).

EXAMPLE 4.6.1 a) Z-Gly-Arg(Pmc)-Gly-OH was prepared by solid phase synthesis analogously to that described in Example 2.2.2.; MS: 689 $MH^+$.

b) A solution of 217 mg of benzyl(6-tert.-butoxycarbonyl-aminomethyl-10-hexyl-3,7-dimethoxy-phenothiazin-4-yl)-acetate in 10 ml of trifluoroacetic acid was left to stand at 20° for 1 hour and then concentrated in a vacuum. The residue was further processed using 276 mg of Z-Gly-Arg(Pmc)-Gly-OH analogously to that described in Example 2.2.1. 40 mg of 10-hexyl-3,7-dimethoxy-4,6-cyclo-[acetyl-glycyl-L-arginyl-glycyl-aminomethyl]phenothiazine trifluoroacetate (1:1) were obtained; MS: 683 $MH^+$.

EXAMPLE 4.7.1 a) 285.7 mg of benzyl(6-aminomethyl-3,7-dimethoxy-10-hexyl-phenothiazin-4-yl)-acetate trifluoroacetate and 298 mg of Fmoc-Arg(Pmc)-OH in 5 ml of DMF were treated at 0° with 160.6 mg of TBTU and 0.17 ml of DIPEA. The reaction mixture was stirred at 20° for 30 minutes and then poured into dilute $NaHCO_2$ solution. The precipitated solid was filtered off, washed with $KHSO_4$/$K_2SO_4$ solution and water and dried in a vacuum. 460 mg of benzyl [6-(((N$^\alpha$(9H-fluoren-9-ylmethoxy-carbonyl)-(N$^6$-(2,2,5,7,8-pentamethylchroman-6-sulphonyl)-L-arginyl)-aminomethyl)-10-hexyl-3,7-dimethoxy-phenothiazin-4-yl]-acetate were obtained; MS: 1165 $MH^\oplus$.

b) A solution of 232 mg of the compound obtained in a) above in 2 ml of piperidine and 8 ml of DMF was left to stand at 20° for 1 hour and subsequently evaporated in a vacuum. The residue was digested with hexane, dissolved in 5 ml of DMF and treated with 95.5 mg of Z-Glu(OBut)-OSu. The reaction mixture was stirred for 2 hours and then evaporated in a vacuum, whereupon the residue was crystallized from ethyl acetate/hexane. 165 mg of benzyl [6-(((N$^\alpha$-benzyloxycarbonyl-O-tert.-butyl-L-glutamyl)-(N$^6$-(2,2,5,7,8-pentamethylchroman-6-sulphonyl)-L-arginyl)-aminomethyl)-10-hexyl-3,7-dimethoxy-phenothiazin-4-yl]-acetate were obtained; MS: 1262.5 $MH^+$.

c) 139 mg of the compound obtained in b) above were further processed as described in Example 2.2.1., except that the chromatographic purification was effected with trifluoroacetic acid/water. 2.5 mg of 3,7-dimethoxy-10-hexyl-4,6-cyclo-[acetyl-L-α-glutamyl-L-arginyl-aminomethyl] phenothiazine trifluoroacetate (1:1) were obtained; MS: 698.3 $MH^+$.

EXAMPLE 4.7.2 a) 280 mg of benzyl[6-((N$^{\alpha-(}$9H-fluoren-9-ylmethoxycarbonyl)-N$^6$-(2,2,5,7,8-pentamethylchroman-6-sulphonyl)-L-arginyl)-aminomethyl)-10-hexyl-3,7-dimethoxy-phenothiazin-4-yl]-acetate were dissolved in 2 ml of piperidine and 8 ml of DMF. The solution was left to stand at 20° for 1 hour and then concentrated in a vacuum. The residue was digested with hexane and dissolved in 5 ml of DMF, whereupon it was processed using 157 mg of Z-Gln(Trt)-OH, 97 mg of TBTU and 0.1 ml of DIPEA analogously to that described in Example 4.7.1. paragraph b). 280 mg of benzyl[6-(((N$^\alpha$-benzyloxycarbonyl-N$^6$-triphenylmethyl)-L-glutamyl)-(N$^6$-(2,2,5,7,8-pentamethylchroman-6-sulphonyl)-L-arginyl)-aminomethyl)-10-hexyl-3,7-dimethoxy-phenothiazin-4-yl]-acetate were obtained; MS: 1447.6 MH.

b) 275 mg of the compound obtained in a) above were further processed as in Example 2.2.1., except that the chromatographic purification was effected with trifluoroacetic acid/water. 46 mg of 10-hexyl-3,7-dimethoxy-4,6-cyclo-[acetyl-L-glutaminyl-L-arginyl-aminomethyl]phenothiazine trifluoroacetate (1:1) were obtained: MS: 697.2 MH.

EXAMPLE 4.7.3 a) The protected tetrapeptide Z-Val-Arg(Pmc)-Lys(Boc)-Lys(Boc)-OH was prepared by solid phase synthesis analogously to that described in Example 2.2.2. MS: 1130.6 $MH^+$.

b) 260 mg of benzyl(6-aminomethyl-3,7-dimethoxy-10-hexyl-phenothiazin-4-yl)-acetate and 572 mg of Z-Val-Arg(Pmc)-Lys(Boc)-OH were treated with TBTU analogously to that described in Example 2.2.2. 735 mg of benzyl[6-((((N-benzyloxycarbonyl-L-valyl)-(N$^6$-(2,2,5,7,8-pentamethylchroman-6-sulphonyl)-L-arginyl)-(N$^6$-(tert.-butoxycarbonyl)-L-lysyl)-(N$^6$(tert.-butoxycarbonyl)-L-lysyl)-aminomethyl)-10-hexyl-3,7-dimethoxy-phenothiazin-4-yl]-acetate were obtained; MS: 1334 $MH^+$.

c) 650 mg of the compound obtained in b) above were further processed analogously to that described in Example 2.2.1. The product was de-salted in a Dowex 44 column in the acetate form. 20 mg of 10-hexyl-3,7-dimethoxy-4,6-cyclo-[acetyl-L-valyl-L-arginyl-L-lysyl-L-lysyl-aminomethyl]phenothiazine acetate (10-hexyl-3,7-dimethoxy-4,6-cyclo-[acetyl-SEQ ID NO:5-aminomethyl]phenothiazine acetate) (1:3) were obtained; MS: 924.8 MH$^+$.

EXAMPLE 4.7.4

From 222 mg of benzyl (6-aminomethyl-3,7-dimethoxy-10-hexyl-phenothiazin-4-yl)-acetate and 362 mg of Z$_3$-Arg-Gly-Asp(OBut)-Val-OH there were obtained, analogously to that described in Example 2.2.2., 28 mg of 10-hexyl-3,7-dimethoxy-4,6-cyclo-[acetyl-L-arginyl-glycyl-L-aspartyl-L-valyl-aminomethyl]phenothiazine trifluoroacetate(10-hexyl-3,7-dimethoxy-4,6-cyclo-[acetyl-SEQ ID NO:2-aminomethyl]phenothiazine trifluoroacetate) (1:1); MS: 840 MH$^+$.

EXAMPLE 4.7.5 a) 280 mg of benzyl[6-(Fmoc-Arg(Pmc)-aminomethyl)-3,7-dimethoxy-10-hexylphenothiazin-4-yl]acetate were treated with piperidine analogously to that described in Example 4.7.1. paragraph b), whereupon further processing was carried out using 89 mg of Z-Ser(But)-OH, 97 mg TBTU and 0.1 ml of DIPEA analogously to that described in Example 4.7.1. paragraph b). 240 mg of benzyl[6-(((N-tert.-butoxycarbonyl-O-tert.-butyl)-L-seryl)-(N$^6$-(2,2,5,7,8-pentamethylchroman-6-sulphonyl)-L-arginyl)-aminomethyl)-10-hexyl-3,7-dimethoxy-phenothiazin-4-yl]-acetate were obtained; MS: 1220.6, MH$^+$.

b) 220 mg of the compound obtained in a) above were further processed analogously to that described in Example 2.2.1., whereby 57 mg of 10-hexyl-3,7-dimethoxy-4,6-cyclo-[acetyl-L-seryl-L-arginyl-aminomethyl] phenothiazine trifluoroacetate (1:1) were obtained; MS: 656.6, MH$^+$.

Example 4.7.6 a) 250 mg of benzyl(6-aminomethyl-3,7-dimethoxy-10-hexyl-phenothiazin-4-yl)-acetate trifluoroacetate (1:1) were reacted with 153 mg of Fmoc-Ser(But)-OH, 141 mg of TBTU and 0.15 ml of DIPEA analogously to that described in Example 4.7.1. 20 mg of benzyl[6-((N-(9H-fluoren-9-ylmethoxycarbonyl)-O-tert.-butyl-L-seryl)-aminomethyl)-10-hexyl-3,7-dimethoxy-phenothiazin-4-yl]-acetate were obtained; MS: 886.6 MH$^\oplus$.

b) 195 mg of the compound obtained in a) above were treated with piperidine and reacted with 126 mg of Z-Arg (Pmc)-OH, 80 mg of TBTU and 0.087 ml of DIPEA analogously to that described in Example 4.7.1. 167 mg of 10-hexyl-3,7-dimethoxy-4,6-cyclo-[acetyl-L-arginyl-L-seryl-aminomethyl]phenothiazine trifluoroacetate (1:1) were obtained; MS: 1220.5 MH$^+$.

EXAMPLE 4.7.7

250 mg of benzyl(6-aminomethyl-3,7-dimethoxy-10-hexylphenothiazin-4-yl)-acetate trifluoroacetate were reacted with 244 mg of Fmoc-Gln(Trt)-OH, 141 mg of TBTU and 0.152 ml of DIPEA analogously to that described in Example 4.7.1. The resulting benzyl[6-((N$^\alpha$(9H-fluoren-9-ylmethoxycarbonyl)-N$^5$-triphenylmethyl-L-glutamyl)-aminomethyl)-10-hexyl-3,7-dimethoxy-phenothiazin-4-yl]-acetate was treated with piperidine and reacted with 184 mg of Z-Arg(Pmc)-OH, 113 mg of TBTU and 0.121 ml of DIPEA analogously to that described in Example 4.7.1, whereby 22 mg of 10-hexyl-3,7-dimethoxy-4,6-cyclo-[acetyl-L-arginyl-L-g lutamyl-aminomethyl]phenothiazine trifluoroacetate (1:1) were obtained; MS: 697.2 MH$^\oplus$.

EXAMPLE 4.7.8

72.8 mg of benzyl(6-aminomethyl-3,7-dimethoxy-10-hexylphenothiazin-4-yl)-acetate trifluoroacetate were reacted with 39.7 mg of Boc-Phe-OH analogously to that described in Example 4.7.1. The crystalline benzyl[6-((N-tert.-butoxycarbonyl-L-phenylalanyl)-aminomethyl)-10-hexyl-3,7-dimethoxy-phenothiazin-4-yl]-acetate obtained was dissolved in trifluoroacetic acid, whereupon the solution was left to stand at 20° for 10 minutes and concentrated in a vacuum. The residue was dissolved in 3 ml of DMF, whereupon 84.3 mg of Z-Tyr(Bzl)-ONp were added and the pH value was adjusted to 8.5 with DIPEA. After 3 hours the reaction mixture was worked up as described Example 4.7.1. The crystalline benzyl[6-(((N,O-bis-benzyloxycarbonyl-L-tyrosyl)-L-phenylalanyl)-aminomethyl)-10-hexyl-3,7-dimethoxy-phenothiazin-4-yl]-acetate obtained was further processed analogously to that described in Example 2.2.1., whereby the crude product was crystallized from ethanol. 21.3 mg of 10-hexyl-3,7-dimethoxy-4,6-cyclo-[acetyl-L-tyrosyl-L-phenylalanyl-aminomethyl]phenothiazine were obtained; MS: 723.5 MH$^+$.

EXAMPLE 4.8.1

170.6 mg (0.45 mmol) of 1-benzotriazol-1-yl-N,N,N',N'-tetramethyluronium hexafluorophosphate (HBTU) and 103.4 mg (1.02 mmol) of N-methylmorpholine were added while cooling with ice to a solution of 220 mg (0.409 mmol) of (10-benzyl-6-tert.-butoxycarbonyl-aminomethyl-3,7-dimethoxy-phenothiazin-4-yl)-acetic acid and 94.5 g (0.45 mmol) of alanyl-alanine methyl ester hydrochloride in 10 ml of N,N-dimethylformamide. The reaction mixture was stirred at room temperature for 1 hour and then poured into ice-water and methylene chloride. The organic phase was separated, extracted with saturated sodium chloride solution, dried over magnesium sulphate and concentrated. The residue was dried in a high vacuum and dissolved in 10 ml of tetrahydrofuran/methanol/water (3:1:1), whereupon the solution was treated at 0° with 50 mg of lithium hydroxide and stirred at room temperature for 1 hour. The mixture was poured into ice-water, whereupon it was acidified with aqueous hydrochloric acid and extracted with methylene chloride. The organic phase was washed with saturated sodium chloride solution, dried over magnesium sulphate and concentrated. The residue was dried in a high vacuum and dissolved in 2 ml of methylene chloride, whereupon the solution was treated at 0° with 2 ml of cold trifluoroacetic acid, stirred for 30 minutes and evaporated to dryness. The residue was dried and dissolved in 20 ml of N,N-dimethylformamide, whereupon the solution was treated at 0° with 132.5 mg (0.48 mmol) of diphenylphosphoryl azide (DPPA) and 134.4 mg (1.60 mmol) of sodium hydrogen carbonate. The reaction mixture was stirred at 0° for 1 hour and, after distilling off the solvent, poured into water and chloroform. The organic phase was separated, dried over magnesium sulphate and concentrated. The residue was chromatographed on silica gel with chloroform/methanol (9:1), whereupon 180 mg (78%) of 10-benzyl-3,7-dimethoxy-4,6-cyclo[acetyl-L-alanyl-L-alanyl-aminomethyl]phenothiazine were obtained as a colourless solid.

MS (FAB): 561 (M$^+$+H, 20), 560 (M$^+$, 8), 469 (30), 327 (30), 276 (30), 365 (30), 250 (100), 221 (20), 197 (20), 181 (20), 149 (20).

EXAMPLE 4.8.2

The peptide resin derivative of H-Leu-DTrp-DAsp(OBzl) was prepared on a 4-(4-hydroxymethyl-3-methoxyphenoxy)-butyryl-aminobenzyl-polystyrene resin analogously to that described in Example 2.2.2. 250 mg of this peptide resin were coupled with 80 mg of (10-benzyl-6-tert.-butoxycarbonyl-aminomethyl-3,7-dimethoxyphenothiazin-4-yl)-acetic acid in the presence of 96 mg of TBTU and 0.1 ml of DIPEA. The modified resin obtained was suspended in 8 ml of acetic acid/2 ml of H$_2$O, whereupon the suspension was left to stand at 60° for 3 hours and then filtered. The filtrate was lyophilized and the resulting product (49 mg) was dissolved in 5 ml of trifluoroacetic acid/0.5 ml of H$_2$O, whereupon the solution was left to stand at 20° for 15 minutes and then evaporated. The residue was cyclized with HBTU and DIPEA in N,N-dimethylformamide analogously to that described in Example 2.2.1. The product was dissolved in 4 ml of tetrahydrofuran/methanol (1:1); the solution was treated with 0.4 ml of 1N LiOH for the purpose of saponification, then acidified with dil. H$_2$SO$_4$ and finally extracted with ethyl acetate. The organic phases were evaporated and the residue was purified by HPLC. 8 mg of 10-benzyl-3,7-dimethoxy-4,6-cyclo-[acetyl-L-leucyl-D-tryptophyl-D-aspartyl-aminomethyl]phenothiazine were obtained;

MS: 833.2 MH$^+$.

EXAMPLE 4.8.3 a) 306 mg (3.02 mmol) of 4-methylmorpholine were added at 0° to a solution of 650 mg (1.21 mmol) of (10-benzyl-6-tert.-butoxycarbonyl-aminomethyl-3,7-dimethoxy-phenothiazin-4-yl)-acetic acid, 413.5 mg (1.37 mmol) of Gly-Gly-Ala-Gly-methyl ester hydrochloride and 504.5 mg (1.33 mmol) of 1-benzotriazo-1-yl-N,N,N',N'-tetramethyluronium hexyfluorophosphate (HBTU) in 12 ml of N,N-dimethylformamide. The reaction mixture was stirred at room temperature for 1 hour, whereupon the solvent was distilled off in a vacuum and the residue was taken up in methylene chloride and saturated sodium hydrogen carbonate solution. The aqueous phase was extracted twice with methylene chloride; the combined organic phases were dried over magnesium sulphate and evaporated. The residue was chromatographed on silica gel with chloroform/methanol (9:1), whereupon, after drying, 790 mg (82.9%) of (10-benzyl-6-tert.-butoxycarbonyl-aminomethyl-3,7-dimethoxy-phenothiazin-4-yl)-acetyl-glycyl-glycyl-L-alanyl-glycine methyl ester (10-benzyl-6-tert.-butoxycarbonylaminomethyl-3,7-dimethoxy-phenothiazine-4-yl)-acetyl-SEQ ID NO:4 methyl ester) were obtained as an amorphous foam.

MS (FAB): 792 (M$^+$+H, 20), 791 (M$^+$, 20), 701 (25), 692 (100). IR (KBr): 3294m, 3086w, 3084w, 2975w, 1742w, 1698m, 1664s, 1632s, 1519s, 1463s, 1366m, 1259s, 1166m, 1049m, 801w.

b) 20 ml of 2N aqueous sodium hydroxide solution were added dropwise while cooling with ice to a solution of 710 mg (0.895 mmol) of the above compound in 20 ml of methanol. The reaction mixture was stirred at room temperature for 1 hour and then poured into ice-water, whereupon the mixture was acidified to pH 3 with aqueous hydrochloric acid and exhaustively extracted with methylene chloride. The combined organic phases were dried over magnesium sulphate and evaporated. The residue was dried in a high vacuum and dissolved in 8 ml of cold trifluoroacetic acid, whereupon the solution was stirred at 0° for 30 minutes and then concentrated in a high vacuum. The residue was suspended in diethyl ether, the suspension was filtered and the residue was dried and dissolved in 100 ml of N,N-dimethylformamide. The solution was treated with 295 mg (3.5 mmol) of dried, powdered sodium hydrogen carbonate and then at 0° with 212 mg (0.77 mmol) of diphenylphosphoryl azide (DPPA). The reaction mixture was stirred at 0° overnight, the N,N-dimethylformamide was distilled off, the residue was taken up in 25 ml of methanol and the product was precipitated by the addition of 150 ml of water. The precipitate was filtered off and dried, whereby 380 mg (81.4%) of 10-benzyl-3,7-dimethoxy-4,6-cyclo [acetyl-glycyl-glycyl-L-alanyl-glycyl-aminomethyl] phenothiazine (10-benzyl-3,7-dimethoxy-4,6-cyclo-[acetyl-SEQ ID NO:4-aminomethyl]phenothiazine) were obtained as a beige solid.

MS (FAB): 661 (M$^+$+H, 12), 569 (20), 251 (45), 197 (90), 181 (70), 165 (55), 147 (70), 105 (100).

EXAMPLE 4.9.1 a) 103 mg (0.726 mmol) of methyl iodide and 110 mg (0.726 mmol) of 1,8-diazabicyclo[5.4.0]undec-7-ene were added while cooling with ice to a solution of 430 mg (0.66 mmol) of 5-(4-benzyloxycarbonylmethyl-6-tert.-butoxycarbonyl-aminomethyl-3,7-dimethoxy-phenothiazin-10-yl)-5-oxo-pentanoic acid in 15 ml of N,N-dimethylformamide. The reaction mixture was stirred firstly at room temperature and then at 40°, then cooled and finally poured into water and ethyl acetate. The organic phase was extracted twice with water, dried over magnesium sulphate and concentrated. The residue was chromatographed on silica gel with ethyl acetate/hexane (1:1), whereupon, after drying, 390 mg (88%) of methyl 5-(4-benzyloxycarbonylmethyl-6-tert.-butoxycarbonyl-aminomethyl-3,7-dimethoxy-phenothiazin-10-yl)-5-oxo-pentanoate were obtained as a white amorphous foam. MS (FAB): 664 (M$^+$).

b) 310 mg (0.466 mmol) of the compound obtained in a) above were dissolved in 5 ml of methylene chloride. The solution was treated at 0° with 5 ml of trifluoroacetic acid and stirred for 30 minutes, whereupon the solvent was distilled off. The residue was dried in a high vacuum and dissolved in 10 ml of N,N-dimethylformamide, whereupon the solution was treated with 256.1 mg (0.699 mmol) of N-α-benzyloxycarbonyl-N-δ-tert.-butoxycarbonyl-L-ornithine, 125.9 mg (0.932 mmol) of N-hydroxybenzotriazole and 185 mg (0.652 mmol) of N-dimethylaminopropyl-N'-ethylcarbodiimide hydrochloride. The reaction mixture was treated with 0.36 g (1.78 mmol) of N-ethyidiisopropylamine while cooling with ice and stirred at 0° for 18 hours, whereupon the N,N-dimethylformamide was distilled off in a high vacuum and the residue was taken up in methylene chloride and water. The organic phase was separated, dried over magnesium sulphate and evaporated. The residue was dried in a high vacuum and dissolved in 15 ml of trifluoroethanol, whereupon 200 mg of palladium-on-charcoal (10%) were added and the mixture was hydrogenated for 3 hours at 1.8 bar of hydrogen. The suspension was filtered over Celite and the filtrate was evaporated. The residue was dried and dissolved in 180 ml of N,N-dimethylformamide. The solution was treated at 0° under argon with 353 mg (0.932 mmol) of 1-benzotriazol-1-yl-N,N,N',N'-tetramethyluronium hexafluorophosphate and 196 ml (2.33 mmol) of sodium hydrogen carbonate (dried and powdered). The reaction mixture was stirred at room temperature for 2.5 hours, whereupon the N,N-dimethylformamide was distilled off in a vacuum and the residue was taken up in water/methylene chloride. The organic phase was separated, dried over magnesium sulphate and evaporated. The residue was chromatographed on silica gel with chloroform/methanol (18:1), whereupon 234 mg (75%) of methyl 5-[(S)-8-(3-tert.-butoxycarbonylaminopropyl)-4,12-dimethoxy-7,10-dioxo-1,15-imino-6,7,8,9,10,11-hexahydro-5H-dibenzo[b,e][1,5,8]thiadiazacyclodecin-17-yl]-5-oxo-pentanoate were obtained as an amorphous foam. MS (FAB): 671 ($M^+$+H, 70), 571 (100).

---

We claim:

1. A compound of the formula

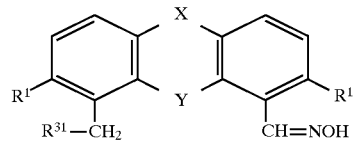
II

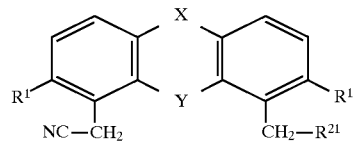
III

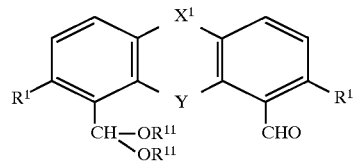
VII

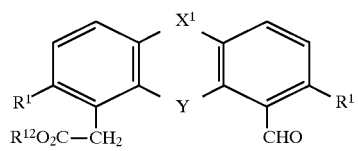
VIII

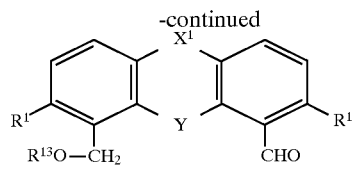
XI

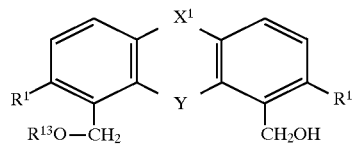
XII

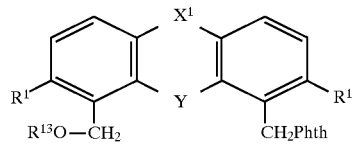
XIII wherein X signifies a group of the formula

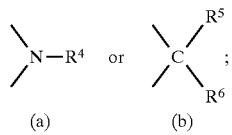

Y signifies oxygen or sulphur;
$R^1$ signifies lower alkoxy;

$X^1$ signifies a residue of formula (a) in which $R^4$ signifies lower alkyl, aryl or aryl-lower alkyl or $X^1$ signifies a residue of formula (b) in which $R^5$ and $R^6$ each signify lower alkyl, aryl or aryl-lower alkyl; the two symbols $R^{11}$ each signify lower alkyl or together signify lower alkylene; $R^{12}$ signifies lower alkyl, aryl or aryl-lower alkyl; $R^{13}$ signifies a protecting group; Phth signifies the phthalimido group; $R^{21}$ signifies protected amino or amino; and $R^{31}$ signifies carboxyl or functionally modified carboxyl.

2. The compound according to claim 1, wherein $R^{13}$ signifies tert.-butyldimethylsilyl, tert.-butyldiphenylsilyl or 2-methoxyethoxymethyl.

* * * * *